US012588861B2

(12) United States Patent
Dagum et al.

(10) Patent No.: US 12,588,861 B2
(45) **Date of Patent: \*Mar. 31, 2026**

(54) WEARABLE DEVICE AND METHOD FOR NON-INVASIVE ASSESSMENT OF GLYMPHATIC FLOW

(71) Applicant: Applied Cognition, Inc., Los Altos Hills, CA (US)

(72) Inventors: Paul Dagum, Los Altos Hills, CA (US); Laurent B. Giovangrandi, Palo Alto, CA (US)

(73) Assignee: Applied Cognition, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/654,877

(22) Filed: May 3, 2024

(65) Prior Publication Data

US 2024/0285224 A1 Aug. 29, 2024

Related U.S. Application Data

(63) Continuation of application No. 18/185,365, filed on Mar. 16, 2023, now Pat. No. 12,004,874.

(Continued)

(51) Int. Cl.
A61B 5/00 (2006.01)
A61B 5/0536 (2021.01)
(Continued)

(52) U.S. Cl.
CPC .......... A61B 5/4064 (2013.01); A61B 5/0536 (2013.01); A61B 5/256 (2021.01);
(Continued)

(58) Field of Classification Search
CPC ..... A61B 5/4064; A61B 5/0536; A61B 5/256; A61B 5/4088; A61B 5/6814;
(Continued)

(56) References Cited

U.S. PATENT DOCUMENTS 4,601,294 A * 7/1986 Danby ..................... A61B 5/12
600/379
4,706,682 A * 11/1987 Stypulkowski ........ A61B 5/283
607/116
(Continued)

FOREIGN PATENT DOCUMENTS

SE 543899 C2 * 9/2021 ........... A61N 1/0404
WO 2019169142 9/2019
(Continued)

OTHER PUBLICATIONS

Goverdovsky et al, "In-Ear EEG From Viscoelastic Generic Earpieces: Robust and Unobtrusive 24/7 Monitoring", IEEE Sensors Journal, Jan. 1, 2016, pp. 271-277, vol. 16, No. 1.
(Continued)

*Primary Examiner* — Rene T Towa
(74) *Attorney, Agent, or Firm* — King & Spalding LLP

(57) ABSTRACT

A computer-implemented method and system includes a head-mounted wearable device with two current electrodes that provide input alternating currents over a range of frequencies to a subject during at least one intervention. The head-mounted wearable device includes at least two sense electrodes that collect voltage difference measurements in response to the input alternating currents. A measurement validation module applies a Hilbert transform or a Kramer-Kronig test to the voltage difference measurements to generate validated time-series impedance spectra. A cranial fluid dynamics module fits the validated time-series impedance spectra to an electrical circuit model to determine a glymphatic flow response to the at least one intervention.

20 Claims, 47 Drawing Sheets

Related U.S. Application Data

(60) Provisional application No. 63/380,726, filed on Oct. 24, 2022.

(51) Int. Cl.

| | |
|---|---|
| *A61B 5/256* | (2021.01) |
| *A61M 21/02* | (2006.01) |
| *A61N 1/05* | (2006.01) |

(52) U.S. Cl.
CPC .......... *A61B 5/4088* (2013.01); *A61B 5/6814* (2013.01); *A61B 5/6817* (2013.01); *A61M 21/02* (2013.01); *A61N 1/0541* (2013.01)

(58) Field of Classification Search
CPC ... A61B 5/6817; A61B 5/4809; A61B 5/0205; A61B 5/024; A61B 5/02405; A61B 5/0295; A61B 5/4812; A61B 5/6803; A61B 5/7264; A61B 5/14507; A61B 5/372; A61B 5/398; A61B 5/291; A61M 21/02; A61N 1/0541
See application file for complete search history.

(56) References Cited

U.S. PATENT DOCUMENTS

| | | | |
|---|---|---|---|
| 6,640,121 | B1 | 10/2003 | Telischi et al. |
| 7,209,775 | B2 | 4/2007 | Bae et al. |
| 8,277,385 | B2 | 10/2012 | Berka |
| 8,884,767 | B2 | 11/2014 | Kidmose |
| 8,926,542 | B2 | 1/2015 | Gerber |
| 9,025,800 | B2 | 5/2015 | Kidmose et al. |
| 9,210,517 | B2 | 12/2015 | Pontoppidan et al. |
| 9,408,552 | B2 | 8/2016 | Kidmose et al. |
| 9,918,650 | B2 | 3/2018 | Kilsgaard et al. |
| 9,949,045 | B2 | 4/2018 | Kure et al. |
| 10,052,065 | B2 | 8/2018 | Boesen |
| 10,194,228 | B2 | 1/2019 | Hirsch |
| 10,275,027 | B2 | 4/2019 | Segal |
| 10,433,788 | B2 | 10/2019 | Boesen |
| 10,542,904 | B2 | 1/2020 | Durand |
| 10,575,777 | B2 | 3/2020 | Ayers et al. |
| 10,606,354 | B2 | 3/2020 | Segal |
| 10,617,297 | B2 | 4/2020 | Turner |
| 10,728,642 | B2 | 7/2020 | Solum et al. |
| 10,743,121 | B2 | 8/2020 | Pontoppidan et al. |
| 10,765,337 | B2 | 9/2020 | Andersen |
| 10,798,487 | B2 | 10/2020 | Hviid |
| 10,835,145 | B1 | 11/2020 | Prevoir et al. |
| 10,841,682 | B2 | 11/2020 | Masaki et al. |
| 10,856,063 | B1 | 12/2020 | Hviid |
| 10,856,071 | B2 | 12/2020 | Verdooner et al. |
| 11,298,542 | B2 | 4/2022 | Aur |
| 11,478,184 | B1 | 10/2022 | Dagum |
| 11,759,142 | B2 | 9/2023 | Dagum |
| 2005/0059876 | A1* | 3/2005 | Krishnan ............. G06T 7/0012 600/407 |
| 2007/0112277 | A1 | 5/2007 | Fischer et al. |
| 2007/0267699 | A1* | 11/2007 | Hoffman ............. H10D 30/751 257/E27.114 |
| 2008/0275352 | A1 | 11/2008 | Shapira |
| 2009/0264776 | A1 | 10/2009 | Vardy |
| 2010/0130884 | A1* | 5/2010 | Linninger ............. A61B 5/053 600/561 |
| 2011/0251503 | A1 | 10/2011 | Ben-Ari |
| 2012/0165695 | A1 | 6/2012 | Kidmose et al. |
| 2012/0302858 | A1 | 11/2012 | Kidmose et al. |
| 2013/0085356 | A1 | 4/2013 | Schlottau |
| 2014/0018649 | A1 | 1/2014 | Jespersen |
| 2014/0371545 | A1 | 12/2014 | Ben-Ari |
| 2015/0011898 | A1* | 1/2015 | Romesburg .......... A61B 5/6801 600/479 |
| 2016/0022195 | A1 | 1/2016 | Vardy |
| 2016/0310028 | A1 | 10/2016 | Kidmose et al. |

| | | | |
|---|---|---|---|
| 2016/0317085 | A1 | 11/2016 | Razavi |
| 2017/0224949 | A1 | 8/2017 | Action |
| 2017/0251950 | A1 | 9/2017 | Piron et al. |
| 2017/0311870 | A1 | 11/2017 | Bardakjian et al. |
| 2017/0311881 | A1 | 11/2017 | Jensen et al. |
| 2018/0014741 | A1 | 1/2018 | Chou |
| 2018/0055398 | A1 | 3/2018 | Westermann et al. |
| 2018/0177421 | A1 | 6/2018 | Kilsgaard et al. |
| 2018/0193633 | A1* | 7/2018 | Gross ................. A61N 1/36025 |
| 2018/0220903 | A1 | 8/2018 | LeBoeuf et al. |
| 2018/0228381 | A1 | 8/2018 | LeBoeuf et al. |
| 2018/0235540 | A1 | 8/2018 | Kirszenblat et al. |
| 2018/0271428 | A1 | 9/2018 | Takagi et al. |
| 2018/0277238 | A1 | 9/2018 | Boesen |
| 2018/0277245 | A1 | 9/2018 | Boesen |
| 2018/0353095 | A1 | 12/2018 | Boesen |
| 2018/0368718 | A1 | 12/2018 | Koziol |
| 2019/0174238 | A1 | 6/2019 | Lunner et al. |
| 2019/0201684 | A1* | 7/2019 | Williams ........... A61N 1/36132 |
| 2019/0209038 | A1 | 7/2019 | Saab et al. |
| 2019/0223747 | A1 | 7/2019 | Chou |
| 2019/0253793 | A1 | 8/2019 | Pedersen et al. |
| 2019/0269336 | A1 | 9/2019 | Perkins et al. |
| 2019/0282119 | A1 | 9/2019 | Andersen et al. |
| 2019/0380597 | A1 | 12/2019 | Howard |
| 2019/0380648 | A1 | 12/2019 | Kirszenblat |
| 2020/0085331 | A1 | 3/2020 | Chou |
| 2020/0225750 | A1 | 7/2020 | Segal |
| 2020/0268265 | A1 | 8/2020 | Walsh et al. |
| 2020/0288253 | A1 | 9/2020 | De Haan et al. |
| 2020/0306493 | A1 | 10/2020 | Lee |
| 2021/0241909 | A1 | 8/2021 | Bulut |
| 2021/0275097 | A1 | 9/2021 | Pushpala |
| 2021/0282698 | A1 | 9/2021 | Garcia Molina |
| 2022/0000421 | A1 | 1/2022 | Ippolito |

FOREIGN PATENT DOCUMENTS

| | | |
|---|---|---|
| WO | 2020035852 | 2/2020 |
| WO | 2020061209 | 3/2020 |
| WO | 2020127940 | 6/2020 |
| WO | 2020210813 | 10/2020 |
| WO | 2022180306 | 9/2022 |

OTHER PUBLICATIONS

Goverdovsky et al. "Hearables: Multimodal physiological in-ear sensing", Scientific Reports, Jul. 31, 2017, pp. 1-10, 7: 6948 | DOI:10.1038/s41598-017-06925-2.

R. Kusche et al., "An in-ear pulse wave velocity measurement system using heart sounds as time reference", Current Directions in Biomedical Engineering 2015; 1:366-370, De Gruyter.

Kwon, Shinjae, Hojoong Kim, and Woon-Hong Yeo; "Recent Advances In Wearable Sensors and Portable Electronics For Sleep Monitoring"; iScience 24.5 (2021): 102461 (Year: 2021).

Hablitz, Lauren M., et al.; "Increased Glymphatic Influx Is Correlated With Hight EEG Delta Power and Low Heart Rate In Mice Under Anesthesia"; Science Advances 5.2 (2019); eaav5447; (Year: 2019).

Tanabe, Sean, et al. "Cohort Study of Electroencephalography Markers of Amyloid-Tau-Neurodegeneration Pathology."; Brain Communications 2.2 (2020): fcaa099. (Year:2020).

International Search Report and Written Opinion issued in PCT Application No. PCT/US2022/023409, mailed Jul. 25, 2022, 9 pages, Korean Intellectual Property Office.

Meghdadi, et al., "Transcranial Impedance Changes During Sleep: A Rheoencephalography Study," IEEE Journal of Translational Engineering in Health and Medicine, vol. 7, 2019.

Guermandi, Marco, et al., "Active Electrode IC for EEG and Electrical Impedance Tomography With Continuous Monitoring of Contact Impedance," IEEE Transactions On Biomedical Circuits and Systems, vol. 9, No. 1, Feb. 2015.

International Search Report and Written Opinion for PCT Patent Application No. PCT/US2023/077566 dated Feb. 19, 2024.

(56)  References Cited

OTHER PUBLICATIONS

International Search Report and Written Opinion for PCT Patent
Application No. PCT/US2023/077562 dated Feb. 19, 2024.
Taoka, Taoshiaki; Neurofluid Dynamics and the Glymphatic Sys-
tem: A Neuroimaging Perspective; Korean J. of Radiology; 2020;
21(11):1199-1209.
Dagum, Paul, et al.; "The Use Of Continuous Brain Parenchymal
Impedance Dispersion To Measure Glymphatic Function In Humans";
MedRxiv; Jan. 9, 2024; https://www.medrxiv.org/.
Moskalenko, Yu, et al.; "Multifrequency REG: Fundamental Back-
ground, Information Meaning and Ways of Data Analysis and
Automation," American Journal of Biomedical Engineering, vol. 2,
No. 4, 2012, pp. 163-174.
European Patent Office Search Report For EP App. No. 22870452.4,
dated Jun. 10, 2025, 13 pages.

* cited by examiner

682

| MEASURE | Value (%) |
|---|---|
| Sensitivity for Wake | 69 |
| Sensitivity for Light Sleep (N1 or N2) | 80 |
| Sensitivity for SWS (N3) | 88 |
| Sensitivity for REM | 99 |
| Overall agreement | 81 |

684

| MEASURE | EEG | Device |
|---|---|---|
| Total Sleep Time (min) | 270 | 282 |
| Sleep Onset Latency (min) | 23 | 23 |
| Wake After Sleep Onset (min) | 65 | 62 |
| Sleep Efficiency (%) | 75 | 79 |
| Number of Awakenings | 22 | 18 |

FIG. 6F 1210                    1220

1230 wearable device 1250

Center band (controller) 1255

Left band 1251

Left earpiece 1253 wearable device 1250

Center band (controller) 1255 electrodes 1275

Right band 1256 inner surface

Left band 1251

Right earbud 1259

Left earbud 1254

Right earpiece 1258

Left earpiece 1253 wearable
device 1260

Center band
(controller)
1265

Left rear band
1262

Left front band
1261

Left earpiece
1263 wearable
device 1260

Center band
(controller)
1265 electrodes
1276

Left rear band
1262

Right front
band 1266 inner
surface

Left front band
1261

Right rear
band 1267

Right earbud
1269

Left earbud
1264

Left earpiece
1263

Right earpiece
1268

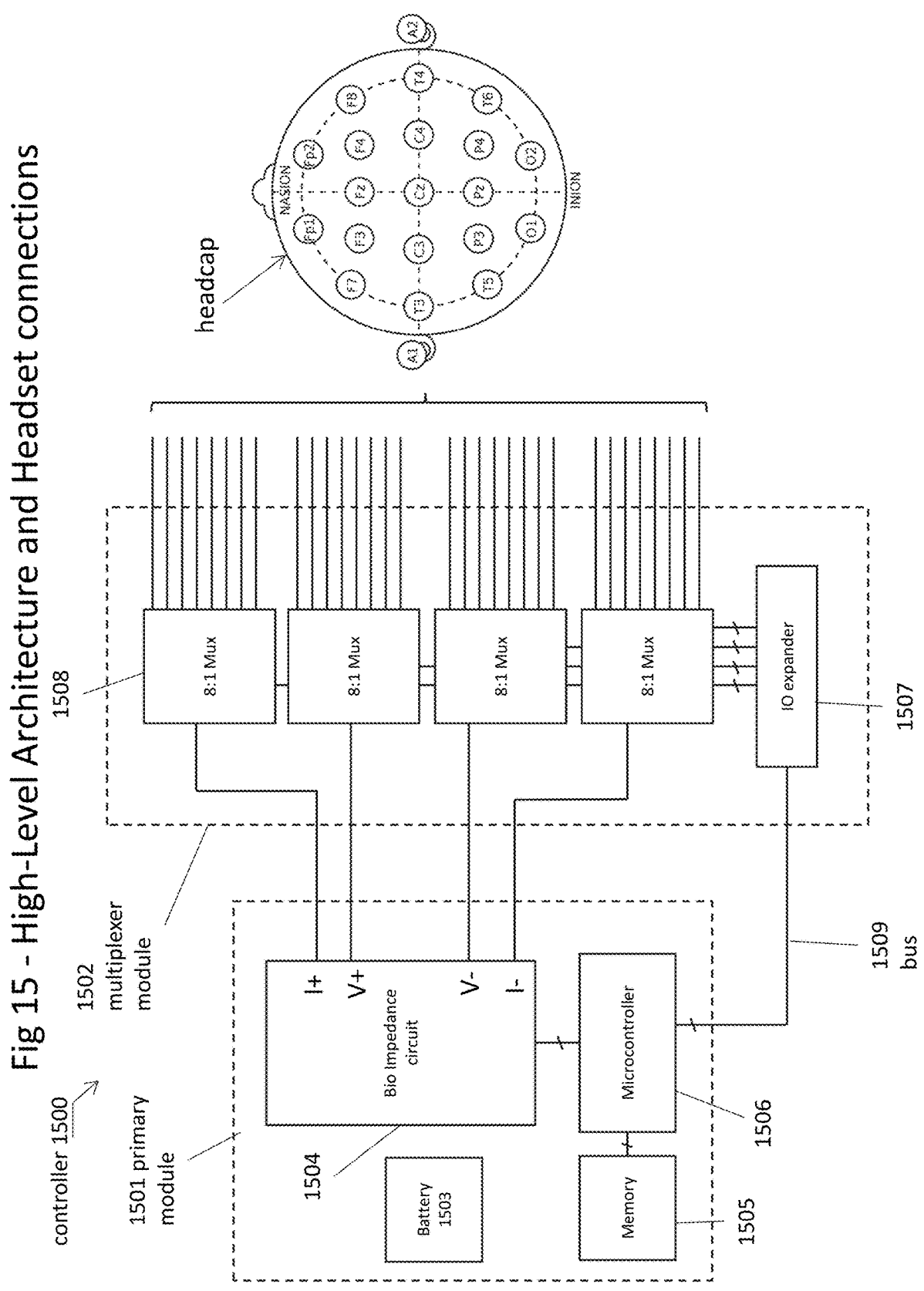
Fig 15 - High-Level Architecture and Headset connections

Fig 16 – Current Drive

Fig 17 - Voltage Sense
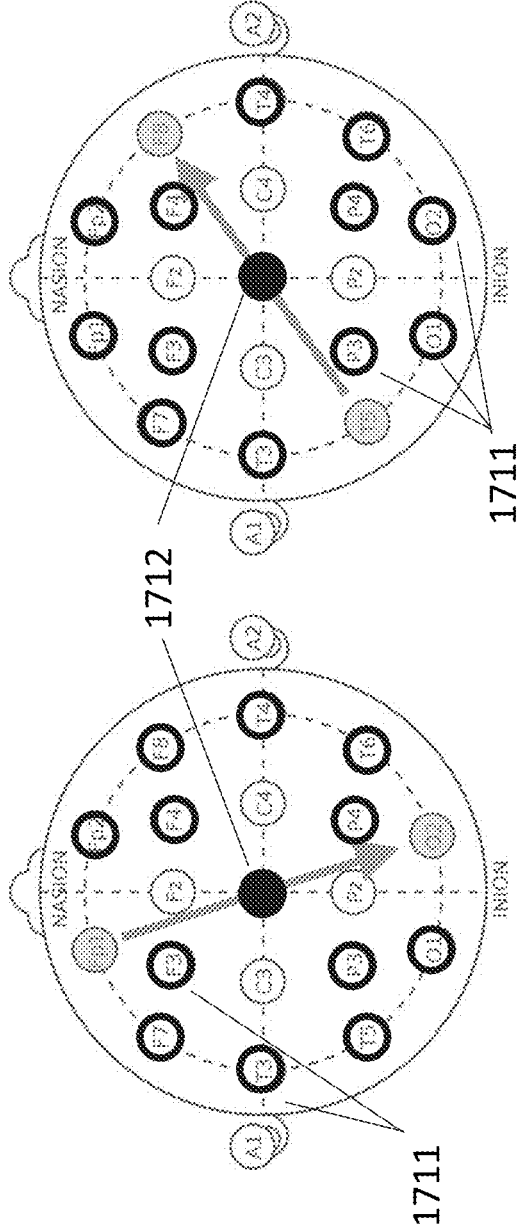
*Figure showing potential sense electrodes for two current injection configurations only.*

| Pin | Electrode | MUX I+ | MUX V+ | MUX V- | MUX I- |
|---|---|---|---|---|---|
| 1 | Fp1 | S1 | S1 | | |
| 2 | F7 | S2 | S2 | | |
| 3 | T3 | S3 | S3 | | |
| 4 | T5 | S4 | S4 | | |
| 5 | O1 | S5 | S5 | | |
| 6 | F3 | | S6 | | |
| 7 | P3 | | S7 | | |
| 8 | GND | | S8 | S8 | |
| 9 | Fp2 | | | S1 | |
| 10 | F8 | | | S2 | S1 |
| 11 | T4 | | | S3 | S2 |
| 12 | T6 | | | S4 | S3 |
| 13 | O2 | | | S5 | S4 |
| 14 | F4 | | | S6 | S5 |
| 15 | P4 | | | S7 | |
| 16 | , | | | | |
| TMUX1108 MUX Pin | Control bit |
|---|---|
| A0 | 0/4 |
| A1 | 1/5 |
| A2 | 2/6 |
| Enable | 3/7 |
| TMUX1108 MUX | MCP23018 Control Nibble |
|---|---|
| V- | GPA0-3 |
| I- | GPA4-7 |
| V+ | GPB4-7 |
| I+ | GPB0-3 |
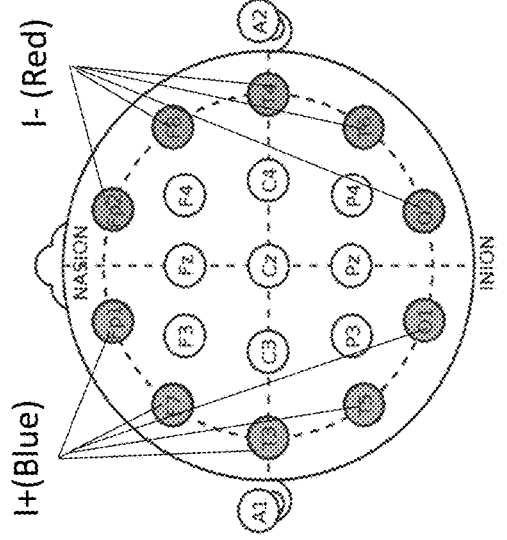
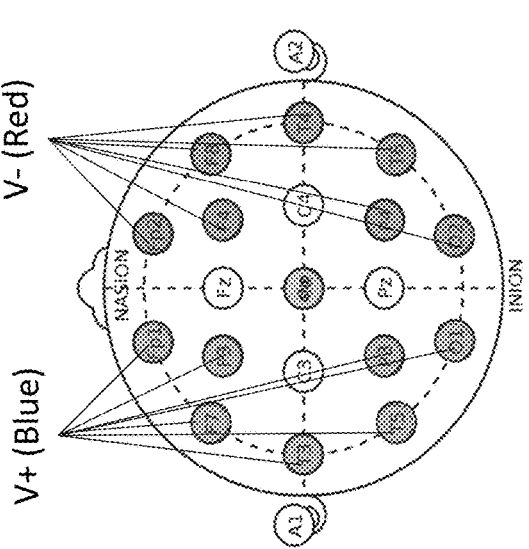
FIG 18. Logic Schema FIG 19. MUX State Machine

| State # | Electrodes | | | |
|---|---|---|---|---|
| | I+ | I- | V+ | V- |
| 1 | Fp1 | O2 | F7 | GND |
| 2 | Fp1 | O2 | T3 | GND |
| 3 | Fp1 | O2 | T5 | GND |
| 4 | Fp1 | O2 | O1 | GND |
| 5 | Fp1 | O2 | F3 | GND |
| 6 | Fp1 | O2 | P3 | GND |
| 7 | Fp1 | O2 | GND | Fp2 |
| 8 | Fp1 | O2 | GND | F8 |
| 9 | Fp1 | O2 | GND | T4 |
| 10 | Fp1 | O2 | GND | T6 |
| 11 | Fp1 | O2 | GND | F4 |
| 12 | Fp1 | O2 | GND | P4 |
| 13 | F7 | T6 | Fp1 | GND |
| 14 | F7 | T6 | T3 | GND |
| 15 | F7 | T6 | T5 | GND |
| 16 | F7 | T6 | O1 | GND |
| 17 | F7 | T6 | F3 | GND |
| 18 | F7 | T6 | P3 | GND |
| 19 | F7 | T6 | GND | Fp2 |
| 20 | F7 | T6 | GND | F8 |
| 21 | F7 | T6 | GND | T4 |
| 22 | F7 | T6 | GND | O2 |
| 23 | F7 | T6 | GND | F4 |
| 24 | F7 | T6 | GND | P4 |
| 25 | T3 | T4 | Fp1 | GND |
| 26 | T3 | T4 | F7 | GND |
| 27 | T3 | T4 | T5 | GND |
| 28 | T3 | T4 | O1 | GND |
| 29 | T3 | T4 | F3 | GND |
| 30 | T3 | T4 | P3 | GND |

| State # | Electrodes | | | |
|---|---|---|---|---|
| | I+ | I- | V+ | V- |
| 31 | T3 | T4 | GND | Fp2 |
| 32 | T3 | T4 | GND | F8 |
| 33 | T3 | T4 | GND | T6 |
| 34 | T3 | T4 | GND | O2 |
| 35 | T3 | T4 | GND | F4 |
| 36 | T3 | T4 | GND | P4 |
| 37 | T5 | F8 | Fp1 | GND |
| 38 | T5 | F8 | F7 | GND |
| 39 | T5 | F8 | T3 | GND |
| 40 | T5 | F8 | O1 | GND |
| 41 | T5 | F8 | F3 | GND |
| 42 | T5 | F8 | P3 | GND |
| 43 | T5 | F8 | GND | Fp2 |
| 44 | T5 | F8 | GND | T4 |
| 45 | T5 | F8 | GND | T6 |
| 46 | T5 | F8 | GND | O2 |
| 47 | T5 | F8 | GND | F4 |
| 48 | T5 | F8 | GND | P4 |
| 49 | O1 | Fp2 | Fp1 | GND |
| 50 | O1 | Fp2 | F7 | GND |
| 51 | O1 | Fp2 | T3 | GND |
| 52 | O1 | Fp2 | T5 | GND |
| 53 | O1 | Fp2 | F3 | GND |
| 54 | O1 | Fp2 | P3 | GND |
| 55 | O1 | Fp2 | GND | F8 |
| 56 | O1 | Fp2 | GND | T4 |
| 57 | O1 | Fp2 | GND | T6 |
| 58 | O1 | Fp2 | GND | O2 |
| 59 | O1 | Fp2 | GND | F4 |
| 60 | O1 | Fp2 | GND | P4 |

WEARABLE DEVICE AND METHOD FOR NON-INVASIVE ASSESSMENT OF GLYMPHATIC FLOW

CROSS-REFERENCE TO RELATED APPLICATIONS

The present application is a continuation application of and claims priority to U.S. patent application Ser. No. 18/185,365 filed Mar. 16, 2023, which application claims the benefit of U.S. Provisional Patent Application No. 63/380, 726 filed Oct. 24, 2022. The present application also is related to U.S. patent application Ser. No. 17/937,952 filed Oct. 4, 2022, which is a continuation application of and claims priority to U.S. patent application Ser. No. 17/713, 329 filed Apr. 5, 2022, which claims the benefit of U.S. Provisional Patent Application No. 63/244,080 filed Sep. 14, 2021. The entire content of the foregoing applications is incorporated herein by reference.

FIELD OF THE INVENTION

The invention relates generally to the collection of and processing of brain impedance spectroscopy data from a wearable device for use in measuring glymphatic flow and glymphatic flow response to an intervention.

BACKGROUND

Interest in brain fluid transport systems has risen rapidly in recent years with the discovery of the glymphatic system and its role in brain protein clearance involved in neurodegeneration such as amyloid-β. Inhibition of glymphatic flow accelerates protein accumulation and cognitive decline in animal models of Alzheimer's disease, traumatic brain injury and Parkinson's disease. The glymphatic flow is primarily active during sleep and driven by cerebrovascular arterial pulsations, thus, sleep, cerebrovascular integrity and neurovascular coupling are required for clearance of waste products that build up in the awake brain. A reduction in glymphatic flow results in accumulation of protein in the brain that leads to neurodegeneration (known as brain proteinopathy) and which can be detected with neuroimaging or molecular analyses of cerebrospinal fluid or blood plasma. Accordingly, non-invasive techniques for monitoring and analyzing information associated with glymphatic flow and its clearance of protein, with a focus on monitoring the mechanism of glymphatic flow that causes the protein accumulation rather than just reporting the accumulation of protein in the brain as done by neuroimaging or molecular analysis, can be useful in diagnosing and treating neurological degeneration.

SUMMARY

The present disclosure is generally directed to collecting neurophysiology and neurovascular data for use in identifying, predicting, and treating neurodegeneration. In one example embodiment, the disclosure is directed to a method, implemented with one or more computer processors, comprising: (a) accessing, by the one or more computer processors, neurophysiological data and neurovascular data recorded during sleep; (b) executing, by the one or more computer processors, a function mapping from said neurophysiological data and neurovascular data to a target that is a marker of glymphatic flow; and (c) outputting, by the one or more computer processors, a target prediction model based on the function mapping.

In another example embodiment, the disclosure is directed to a system comprising: (a) one or more computer processors; (b) a neurophysiological data acquisition module configured to measure neurophysiological data; (c) a neurovascular data acquisition module configured to measure neurovascular data; and (d) a transmission module configured to transmit the electroencephalogram data and the neurovascular data to a second computing device.

In another example embodiment, the disclosure is directed to a system for measuring glymphatic flow, wherein the system comprises: (a) a head-mounted wearable device comprising two current electrodes that provide input alternating currents over a range of frequencies to a subject during at least one intervention and at least two sense electrodes that collect voltage difference measurements in response to the input alternating currents; (b) a measurement validation module that applies a Hilbert transform or a Kramer-Kronig test to the voltage difference measurements to generate validated time-series impedance spectra; and (c) a cranial fluid dynamics module that determines a model fit of the validated time-series impedance spectra to an electrical circuit model, wherein the model fit indicates a glymphatic flow response to the at least one intervention.

The foregoing system can comprise one or more of the following features. In the foregoing example system, the at least one intervention is one of sleep, sleep deprivation, drug infusion, electrostimulation, and physiological stimulation. The system can further comprise an intervention module that controls one of the drug infusion, the electrostimulation, or the physiological stimulation. In the foregoing system, the glymphatic flow response can indicate a change in volume of the brain interstitial fluid or a change in brain interstitial fluid flow. The cranial fluid dynamics module can use the model fit of the validated time-series impedance spectra to the electric circuit model to calculate a time-series of resistance corresponding to glymphatic flow. The cranial fluid dynamics module can compare the glymphatic flow response to the at least one intervention to glymphatic flow responses gathered from the subject previously and can provide an assessment of disease progression. The cranial fluid dynamics module can compare the glymphatic flow response to the at least one intervention to a population distribution of glymphatic flow responses gathered from other subjects and can provide an assessment of disease progression for the subject. In the foregoing system, the measurement validation module and the cranial fluid dynamics module can reside in a computing device that communicates with the head-mounted wearable device. In the foregoing system, the head-mounted wearable device can further comprise a voltage sensing circuit and a current source or voltage source that generates the input alternating currents.

In another example embodiment, the disclosure is directed to a method for measuring glymphatic flow, wherein the method can comprise: (a) providing a head-mounted wearable device worn by a subject, the head-mounted wearable device comprising two current electrodes and at least two sense electrodes; (b) providing input alternating currents via the two current electrodes over a range of frequencies to a subject during at least one intervention; (c) collecting, with the at least two sense electrodes, voltage difference measurements in response to the input alternating currents; (d) applying, by a measurement validation module, a Hilbert transform or a Kramer-Kronig test to the voltage difference measurements and generating validated time-series impedance spectra; and (e) determining, by a cranial fluid dynamics module, a model fit of the validated time-series impedance spectra to an electrical circuit model and wherein the model fit indicates a glymphatic flow response to the at least one intervention.

The foregoing method can comprise one or more of the following features. In the foregoing example method, the at least one intervention is one of sleep, sleep deprivation, drug infusion, electrostimulation, and physiological stimulation. The method can further comprise controlling, by an inter-vention module, one of the drug infusion, the electrostimu-lation, or the physiological stimulation. In the foregoing method, the glymphatic flow response can indicate a change in volume of the brain interstitial fluid or a change in brain interstitial fluid flow. The cranial fluid dynamics module can use the model fit of the validated time-series impedance spectra to the electric circuit model to calculate a time-series of resistance corresponding to glymphatic flow. The cranial fluid dynamics module can compare the glymphatic flow response to the at least one intervention to glymphatic flow responses gathered from the subject previously and can provide an assessment of disease progression. The cranial fluid dynamics module can compare the glymphatic flow response to the at least one intervention to a population distribution of glymphatic flow responses gathered from other subjects and can provide an assessment of disease progression for the subject. In the foregoing method, the measurement validation module and the cranial fluid dynam-ics module can reside in a computing device that commu-nicates with the head-mounted wearable device. In the foregoing method, the head-mounted wearable device can further comprise a voltage sensing circuit and a current source or voltage source that generates the input alternating currents.

The foregoing embodiments are non-limiting examples and other aspects and embodiments will be described herein. The foregoing summary is provided to introduce various concepts in a simplified form that are further described below in the detailed description. This summary is not intended to identify required or essential features of the claimed subject matter nor is the summary intended to limit the scope of the claimed subject matter.

BRIEF DESCRIPTION OF THE DRAWINGS

The specific features, aspects and advantages of the present invention will become better understood with regard to the following description and accompanying drawings where:

FIGS. 6A-6F illustrate the neurophysiology data acquisi-tion module and example associated data in accordance with one embodiment of the present invention.

FIG. 15 illustrates components of a controller for a headcap embodiment of a wearable device in accordance with the present disclosure.

FIGS. 16, 17, 18, and 19 illustrate a method of using the headcap embodiment of a wearable device in accordance with the present disclosure.

DETAILED DESCRIPTION OF EXAMPLE EMBODIMENTS

Figure 1A:
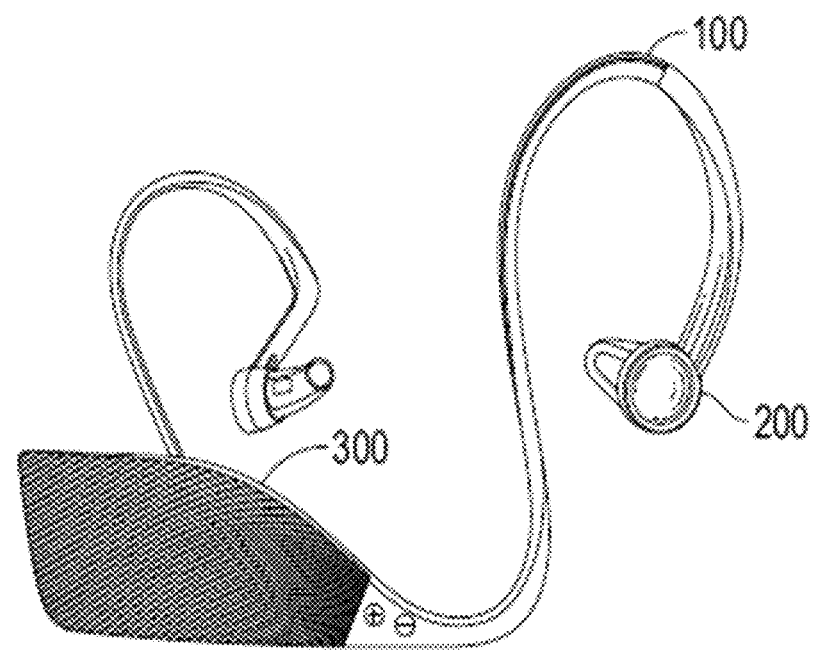
FIGS. 1A and 1B illustrate an embodiment of the system for non-invasive measurement of brain proteinopathy and neurodegeneration that is comparable to molecular analyses or neuroimaging configured in accordance with the present invention.

Referencing the glymphatic flow responsible for the clearance of proteins described above, the perivascular spaces (PVS) of the brain are central to the glymphatic fluid transport system. Fluorescent dye-labeled particles that enable visualization of the perivascular spaces reveals that the system comprises periarterial, pericapillary, and perivenular spaces all interconnected into a single network. The glymphatic flow system clears brain interstitial fluid (ISF) waste products such as the proteinopathy proteins through the periarteriolar and perivenular spaces to meningeal lymphatics. The PVS is a site of great importance that is affected by disease processes such as cerebral amyloid angiopathy characterized by perivascular amyloid beta deposits and present in over 90% of Alzheimer's disease brains. PVS accumulation of p-tau is also observed in Alzheimer's disease and has been demonstrated to be present in arteries, arterioles and veins in the brain. In the glymphatic flow system, cerebrospinal fluid (CSF) enters the periarterial spaces, running in the direction of the blood flow and propelled by arterial wall pulsations. CSF mixes with ISF facilitated by aquaporin-4 (AQP4) water channels that are present at the vascular astrocytic endfeet forming the outer wall of the perivascular spaces. During sleep, arterial pulsations drive CSF bulk flow towards the brain. This process has been shown to be highly dependent on the arousal state and AQP4 expression. With modern neuroimaging techniques, it is now possible to visualize CSF flow and its clearance of proteins in the intact CNS by the second-to-second pulsatile movement of CSF through the ventricular system occurring with each cardiac contraction. Respirations further contribute to this rhythm, adding pulsations at a lower frequency. Superimposed on these acute pulsations is a circadian or diurnal rhythm with maximum CSF production occurring at night during sleep and minimum occurring in the afternoon. MRI studies in animal models using CSF tracers reveal that the glymphatic flow from ISF to subarachnoid CSF is enhanced during NREM sleep.

Sleep has profound effects on most aspects of brain physiology, including glymphatic flow and brain blood volume. In animal models, the amplitude of brain blood volume in non-rapid-eye movement (NREM) sleep doubles compared to the awake state and the amount of total blood volume in the brain changes significantly in the transition from wake to sleep and back to wake, showing that brain blood volume dynamics is coupled to arousal state. These changes in blood volume during sleep are linked to variations in neural activity which drive fluctuations in the diameter of arterioles. The strength of this neurovascular coupling changes with arousal state, increasing substantially during sleep compared to wakefulness and explains the increase in brain blood volume during sleep when neural activity is lower than in the wake state.

The concentration of amyloid-β and tau in the interstitial space and CSF follow a diurnal pattern with both protein concentrations reaching their peak during wakefulness and trough during sleep. A single night of sleep deprivation results in a significant increase in soluble amyloid-β in the brain ISF demonstrated with positron emission tomography (PET) using an amyloid-binding radiotracer. The net concentration of amyloid-β, tau and other proteins in the CSF and ISF reflect the combined effects of diurnal- and state-dependent variations in CSF production rate, ISF volume, ISF turnover rate, and glymphatic flow. Sleep slow-wave delta waves are associated with glymphatic flow and the amplitudes of slow delta waves responsible for effective waste removal during sleep. Sleep deprivation results in stalled glymphatic flow and the accumulation of waste solutes including amyloid-β solutes and other proteins in the brain.

During sleep, glymphatic flow is increased by the action of astrocytes using AQP4 channels that are responsible for the modulation of phases between sleep and awake states. Using membrane channel protein AQP4 and water flux through AQP4, astrocytes can shrink the cell volume of brain parenchyma to increase ISF space by 23% during sleep enabling water and solutes to diffuse into adjacent perivascular spaces. During slow-wave sleep, the increase in ISF space, the opening of gap junction of astrocyte end-feet and an increase in cerebral hemodynamics creates an environment for exchange of nutrients and elimination of waste between ISF and CSF.

Damage to molecular and cellular components of the glymphatic flow system, to the brain neurovascular integrity and to its neurovascular coupling that occurs with aging, chronic co-morbidities, neurodegenerative diseases and physical brain trauma is closely linked to an increase of tau and amyloid-β in extracellular fluids. The spread of these aggregated proteins in the brain parenchyma leads to worsening clinical symptoms and decline in cognition. Measuring the functional integrity of this system and the pathological accumulation of proteins in the brain ISF requires invasive procedures such as PET scans with radiotracers that bind to the protein of interest or lumbar puncture for CSF extraction and analysis of protein concentrations. The cost and complexity of these procedures limits their use to screen for brain proteinopathies or to monitor their progression. Without access to these tests, practitioners today use clinical assessment and cognitive evaluations to screen, diagnose and monitor neurodegenerative disorders such as Alzheimer's disease. The opportunity to intervene early in the 10-to-20-year pre-clinical period of these disorders is lost as is the ability to evaluate promising new treatments that could slow or stop disease progression. Another challenge with existing invasive test procedures is that they must be done in a hospital or clinic setting by trained technicians. This poses additional patient burden that further reduces the effectiveness of these expensive and time-consuming invasive procedures for monitoring progression of proteinopathy, adjusting care plans and monitoring response to new treatments.

The glymphatic system of protein waste clearance operates during sleep and is dependent on features measurable with sleep electroencephalogram (EEG) and on features that measure neurovascular blood volume, pulsation and coupling. Short term disruption in sleep causes an increase in CSF and ISF waste proteins and long-term disruption leads to formation of ISF protein aggregates with neurodegeneration. A wearable device that can measure the relevant EEG features, brain blood volume changes and arterial pulsations during sleep, transmitting the data to a method and system that can predict CSF and ISF waste protein levels and ISF protein aggregation as can be measured using an existing invasive clinical procedure, would provide a significant advantage to medical screening and monitoring of neurodegenerative proteinopathy and help select appropriate interventions that slow or stop protein accumulation and neurodegeneration. As used herein and as described further below, a "wearable device" is a device worn by a subject comprising one or more sensors for collecting neurophysiological and/or neurovascular data from the subject, a processor, memory, and storage device for storing the collected data, and at least one wireless transmission module enabling the wearable device to transmit the collected data to another computing device. The wireless communication capability of the wearable device allows the wearable device to be self-contained so that it requires no external wiring to other equipment. The wearable device is configured to be worn by the subject while sleeping.

According to the embodiment(s) of the present disclosure, various views are illustrated in FIGS. 1A-11C and like reference numerals are being used consistently throughout to refer to like and corresponding parts of the example embodiments for all of the various views and figures of the drawing. Also, please note that the first digit(s) of the reference numbers in FIG. 1 and FIG. 4 correspond to the FIG. number in which the item or part is described in further detail.

The following detailed description contains many specifics for the purpose of illustration. Any one of ordinary skill in the art will appreciate that many variations and alterations to the following details are within scope of the disclosure. Accordingly, the following example embodiments are set forth without any loss of generality to, and without imposing limitations upon, the claimed invention.

Example embodiments of the present disclosure comprise a system and method that enables non-invasive measurement of brain proteinopathy and neurodegeneration. Such measurements are typically done in a medical facility using sophisticated equipment and involve a molecular analysis of cerebrospinal fluid or neuroimaging, and include proteinopathy proteins amyloid, tau or alpha-synuclein levels in a blood plasma or CSF assay, brain amyloid or tau load on a PET scan, brain atrophy on a structural brain MRI, repeated diurnal assessments to measure net change in proteinopathy protein CSF assay or soluble proteinopathy protein burden from neuroimaging. Example embodiments of the present disclosure teach a novel system and method that acquires sleep neurophysiology data synchronized with neurovascular data. The neurophysiology data includes electroencephalogram (EEG) data. The neurovascular data includes continuous transcranial impedance plethysmography (IPG), carotid pulse transit time (PTT), heart rate variability (HRV) and resting heart rate (RHR). The example embodiments can further perform the step of acquiring one of said molecular analyses or neuroimaging test of neurodegeneration following sleep and learning a function mapping from the sleep neurophysiology and neurovascular data to a molecular analyses or neuroimaging marker of neurodegeneration. Learning the function mapping includes using a loss function to determine relevant features in the sleep data, identifying a set of optimal weights that produce a minimum of the loss function, and creating a function mapping, also referred to as a brain proteinopathy and neurodegeneration prediction model, using the optimal weights. The example embodiments can further include performing the step of applying the learned function mapping to new sleep neurophysiology and neurovascular data to screen for, or monitor, said molecular analyses or neuroimaging marker of neurodegeneration. The example embodiments can further include delivering a therapeutic intervention that targets an aspect of sleep neurophysiology or neurovascular either preceding sleep or during sleep, measuring target engagement or effect on the sleep neurophysiology and neurovascular, and further performing the step of applying the learned function mapping to predict the therapeutic effect on brain proteinopathy and neurodegeneration.

Another embodiment of the present disclosure comprises a system and method that enables a person to monitor the effect of a cardiovascular intervention or activity on a molecular analysis or neuroimaging marker of neurodegeneration, which embodiment teaches a novel system and method for performing the step of recording a cardiovascular intervention or activity data that precedes sleep, further performing the step of recording neurophysiology and neurovascular data during sleep and applying a learned function mapping to predict the therapeutic effect on brain proteinopathy and neurodegeneration of the cardiovascular intervention or activity.

Another embodiment of the present disclosure comprises a system and method that enables a person to monitor the effect of a pharmaceutical or neuromodulation intervention on a molecular analysis or neuroimaging marker of neurodegeneration, which embodiment teaches a novel system and method for performing the step of recording a pharmaceutical or neuromodulation intervention either preceding sleep or during sleep, further performing the step of recording neurophysiology and neurovascular data during sleep and applying a learned function mapping to predict the therapeutic effect on brain proteinopathy and neurodegeneration of the pharmaceutical or neuromodulation intervention.

Another embodiment of the present disclosure comprises a system and method that enables a person to monitor the effect of a diet intervention on a molecular analysis or neuroimaging marker of neurodegeneration, which embodiment teaches a novel system and method for performing the step of recording a diet intervention that precedes sleep, further performing the step of recording neurophysiology and neurovascular data during sleep and applying a learned function mapping to predict the therapeutic effect on brain proteinopathy and neurodegeneration of the diet intervention.

Another embodiment of the disclosure can be a wearable system comprising a wearable computer with sensors and a wireless communication interface to a mobile computer supporting a wireless network interface which communicates with a second computer including a network interface, each computer further including a processor, a memory unit operable for storing a computer program, an input mechanism operable for inputting data into said computer system, an output mechanism for presenting information to a user, a bus coupling the processor to the memory unit, input mechanism and output mechanism, wherein the wearable system includes various executable program modules stored thereon where when executed are operable to perform functions. The wearable computer with sensors can comprise a neurophysiology data acquisition module with sensors capable of recording EEG, a neurovascular data acquisition module with sensors capable of recording neurovascular data, with the data stored on the wearable computer where when executed records to the memory unit of said wearable computer the neurophysiology and neurovascular sensor acquisition data. A transmission module can comprise a wireless network interface (e.g., a Bluetooth or WiFi radio) as well as instructions stored on said wearable computer where when executed transmit through the wireless network interface the recordings stored in the memory unit to said mobile computer. A second transmission module can also be stored on said wearable computer and comprise a wired network interface as well as instructions where when executed transmit through a bus network interface the recordings stored in the memory unit to a local computer station that further transmits the data to a second computer through a wireless network interface. A learning module can be stored on said second computer where when executed learns a function mapping from said transmitted recording to a molecular analysis or neuroimaging marker of neurodegeneration stored on said second computer, uses a loss function to determine relevant features in said recording, identifies a set of optimal weights that produce a minimum for said loss function, and creates said function mapping using said optimal weights. A brain proteinopathy and neurodegeneration prediction module can also be stored on said second computer where when executed applies the learned function mapping, also referred to as the brain proteinopathy and neurodegeneration prediction model, to a new transmitted recording of sleep neurophysiology and neurovascular sensor data from the wearable computer with sensors, to calculate a predicted value for the molecular analysis or neuroimaging marker of neurodegeneration from the new transmitted recordings. Thus, the brain proteinopathy and neurodegeneration prediction model can determine a predicted brain proteinopathy and neurodegeneration value from the new recording of data without requiring the invasive imaging or assay procedures described previously.

Another embodiment of the disclosure can be a wearable system comprising a wearable computer with sensors and a wireless communication interface to a mobile computer supporting a wireless network interface which communicates with a second computer including a network interface, each computer further including a processor, a memory unit operable for storing a computer program, an input mechanism operable for inputting data into said computer system, an output mechanism for presenting information to a user, a bus coupling the processor to the memory unit, input mechanism and output mechanism, wherein the wearable system includes various executable program modules stored thereon where when executed are operable to perform functions. In one embodiment, the wearable system can comprise a data acquisition module with sensors capable of recording cardiovascular activity data, with said data stored on the wearable computer where when executed records to the memory unit of said computer the acquisition data. In another embodiment, the wearable system can comprise a data input module capable of recording diet and nutrition data, with said data stored on the mobile computer where when executed records to the memory unit of said computer the data. In another embodiment, the wearable system can comprise a data input module capable of recording drug or neurostimulation data, with said data stored on the mobile computer where when executed records to the memory unit of said computer the data. In any of the preceding embodiments, a transmission module can comprise a communication interface and associated instructions stored on said wearable or mobile computer where when executed transmit through the wireless network interface the recordings stored in the memory unit to said second computer. In any of the preceding embodiments, a module can be stored on said second computer where when executed applies a learned function mapping to said transmitted recording of sleep neurophysiology and neurovascular sensor data from the wearable computer with sensors, to calculate a value for a molecular analysis or neuroimaging marker of neurodegeneration from the transmitted recordings.

Figure 1B:
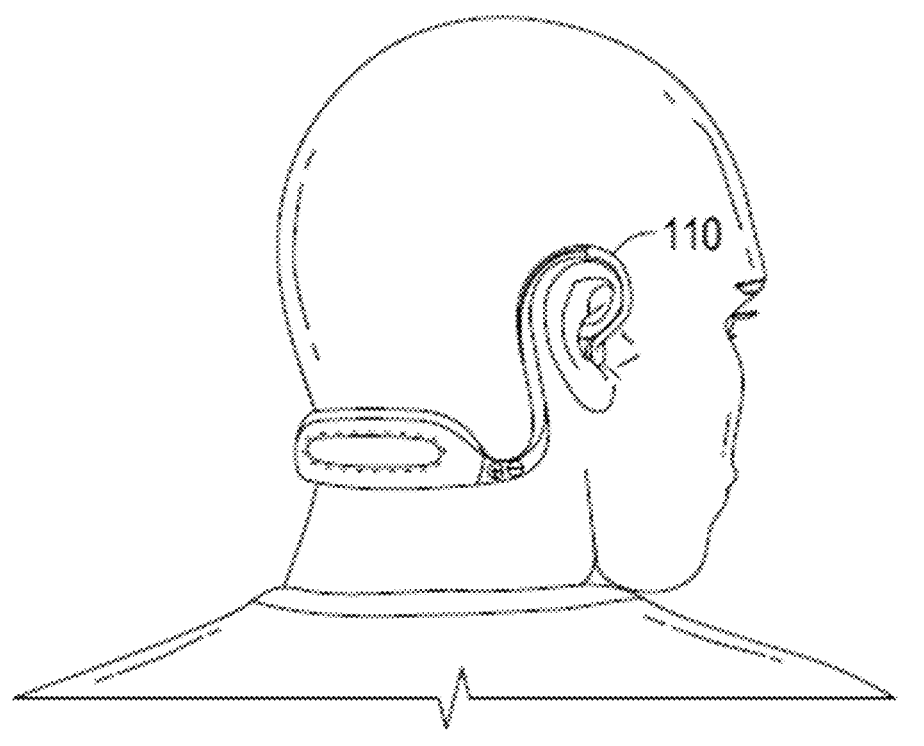

The details of the invention and various embodiments can be better understood by referring to the figures of the drawing. FIGS. 1A and 1B illustrate an embodiment of the functional description of the system configured in accordance with the present invention and is not intended to limit scope as one of ordinary skill would understand on review of this application that other configurations could be utilized without departing from the scope of the claimed invention. Referring to FIG. 1, the system can comprise a wearable device that can be attached to a subject's head. In one example, the wearable device can attach to the subject's ear. The wearable device can comprise the previously described neurophysiology and neurovascular data acquisition sensors 200 for non-invasive measurement. As further illustrated in FIG. 1, the wearable device can comprise a data storage, processing and transmission module 300 that stores the sensor data acquired, transforms the data to preliminary measurements of sensor impedance for determining that the sensors are correctly placed and the bladder is correctly pressurized, and can communicate with a mobile computer and/or a local computer, and/or a remote second computer to transmit the data for further processing into measurements of brain proteinopathy and neurodegeneration that are comparable to molecular analyses or neuroimaging markers. The non-invasive sensors 200 are connected to module 300 through a form-fitting band 100 that houses electrical conduits, electronically isolating digital from analog sensor signals, an air tube that connects an air bladder in sensor 200 with a piezoelectric pump in 300 and inflates the in-ear portion of the ear device 200 to ensure adequate interfacial contact between the surface sensors and the ear and canal epidermis, and a nitinol band designed to ensure secure fitting of the wearable device. An illustration of the attached device is shown in 110. It should be understood that in alternate embodiments the components of the wearable device can have other configurations and can attach to the user with other mechanisms. For example, the air bladder can be replaced by another type of bladder that fills with fluid.

Figure 2B:
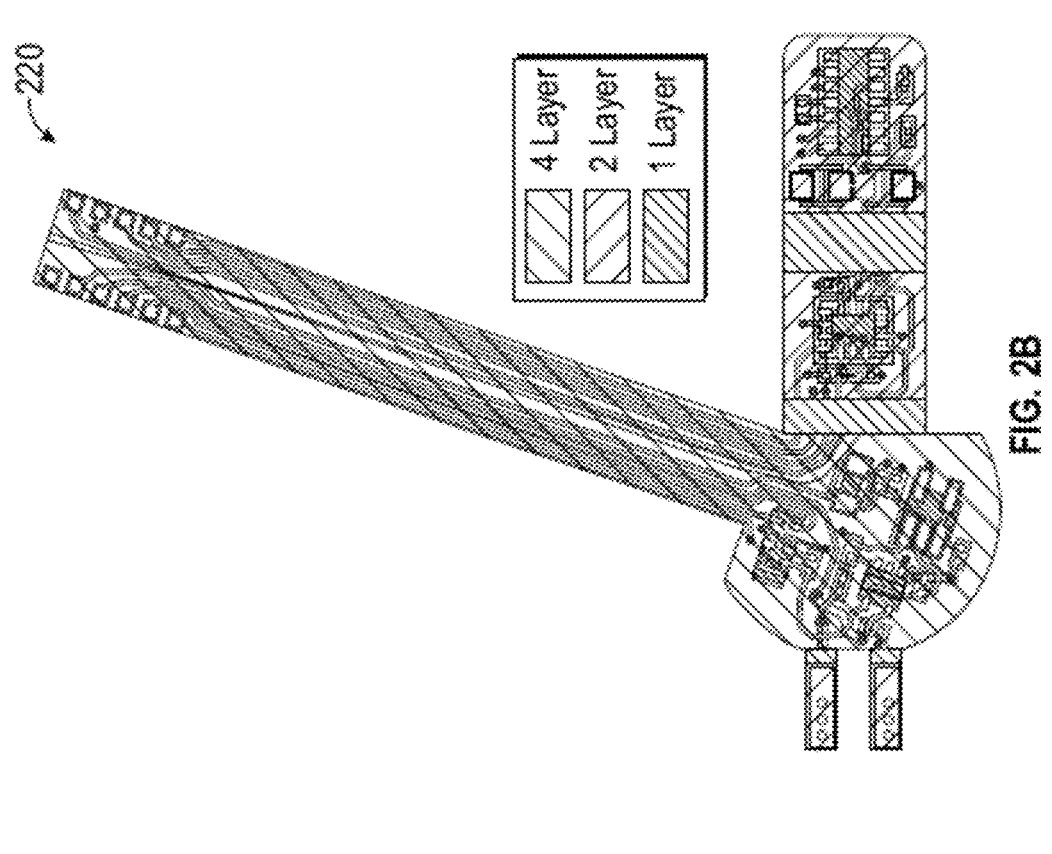
FIGS. 2A-2B illustrate an embodiment of the in-ear sensors of the system for non-invasive measurement of brain proteinopathy and neurodegeneration that is comparable to molecular analyses or neuroimaging configured in accor-dance with the present invention.
Figure 2A:
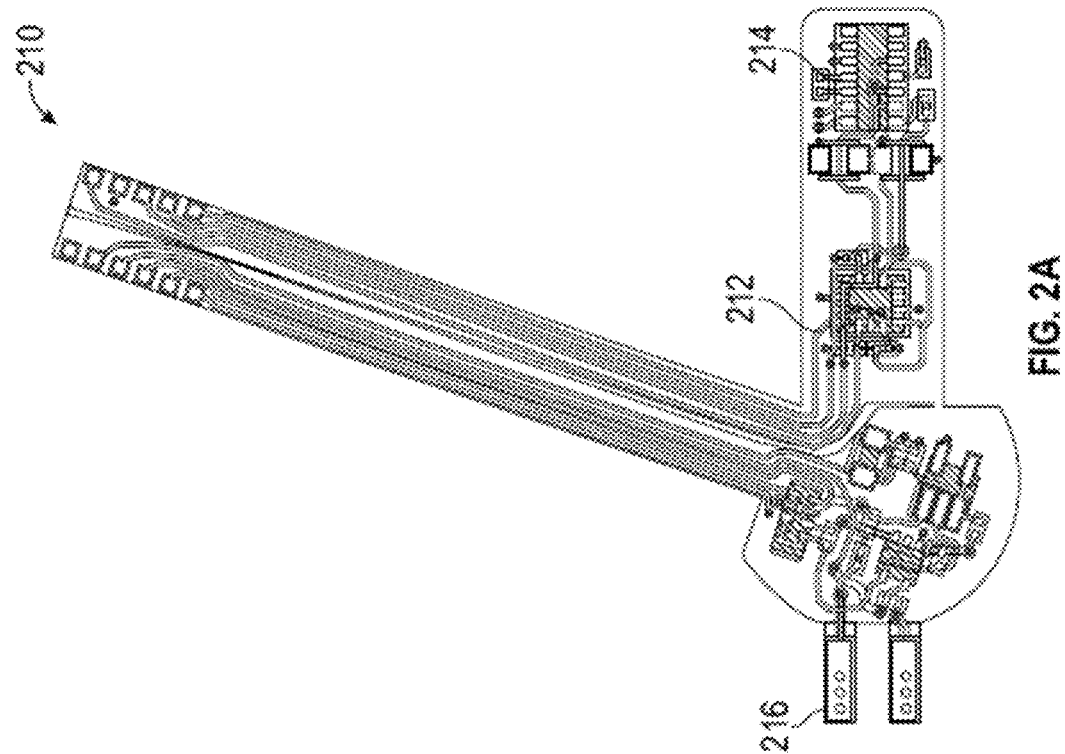
Figure 2C:
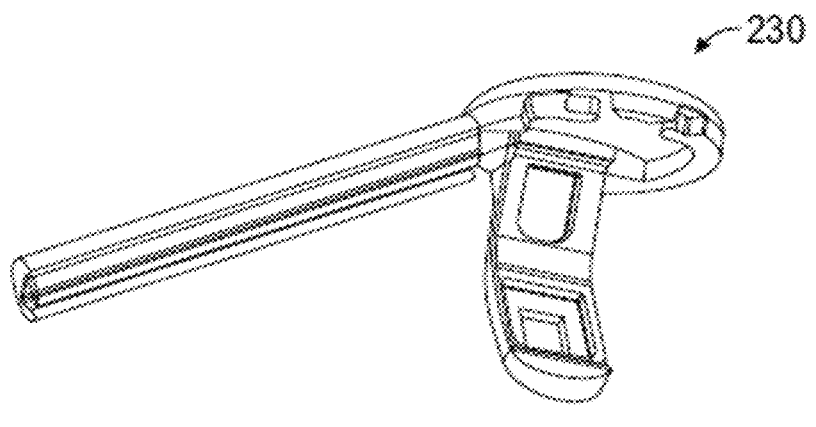
FIGS. 2C-2G illustrate the assembly process of the ear device that includes the flex circuit and manufactured soft-silicone components in accordance with the present inven-tion.
Figure 2D:
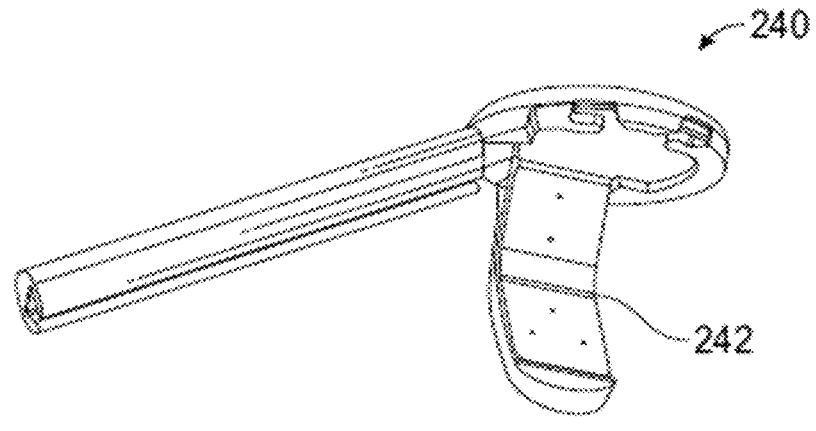
Figure 2E:
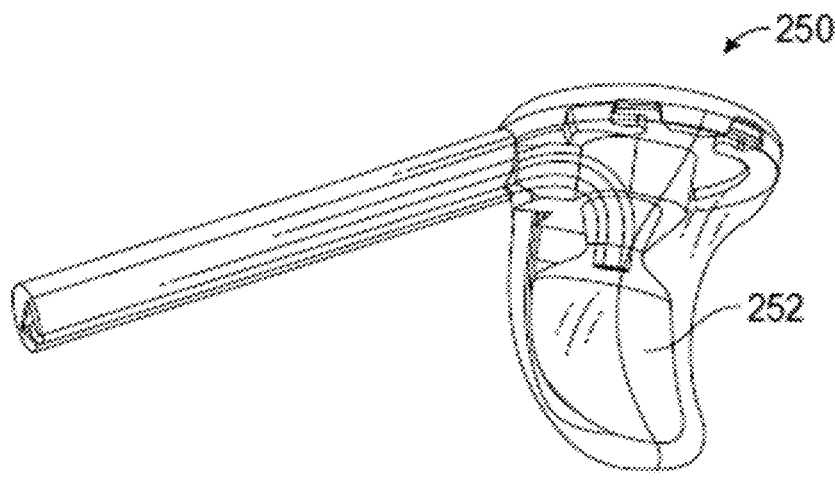

FIGS. 2A-2B illustrate an embodiment of the ear sensors of the system configured in accordance with the present invention and are not intended to limit scope as one of ordinary skill would understand on review of this application that other configurations could be utilized without departing from the scope of the claimed invention. Referring to FIG. 2(a), the flex circuit housed by the ear device 200 is illustrated in 210. Component 212 illustrates positioning of the inertial measurement unit (IMU) that measures milligravitational acceleration capable of perceiving ballistic acceleration in the ear from the blood ejected into the aorta with each cardiac contraction. Component 214 illustrates positioning of the photoplethysmogram (PPG) sensor on the flex circuit so that it is in contact with the ear canal wall. The PPG through measuring the reflection of two wavelengths of infrared light through the ear canal skin is capable of measuring pulsatile changes of ear capillary blood volume with each heart beat and arterial oxygen saturation. Flex circuit leads 216 are terminated on the surface of the ear device 200 to be in contact with two conductive electrodes covering the ear device that can be conductive ink, fabric or other material. Referring to FIG. 2(b) providing illustration 220, the 1-layer sections of the flex circuit are designed to flex naturally to accommodate for differences in user ear anatomy, the second layer of the 2-layer sections of the flex is a stiffener applied to the undersurface of the flex circuit to keep the sections stiff so that the active and passive electronic components do not detach with bending, and the 4-layer section has a grounding plane between analog and digital signals to reduce or eliminate electronic coupling resulting in signal corruption.

Figure 2F:
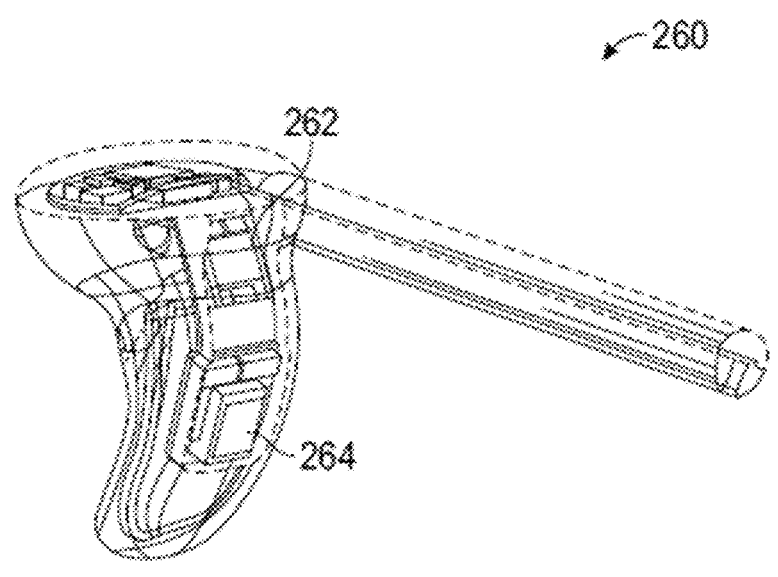

Referring to FIGS. 2C-2G, the illustrations 230, 240, 250, 260 and 270 show the assembly process of the ear device that includes the flex circuit 210 and manufactured soft-silicone components illustrated in 230 and 250. Illustration 240 shows the flex circuit 242 attached to the silicone component 230. Illustration 250 shows the bladder 252 in the second silicone component that is pressurized, with air or fluid, once inside the ear canal. Through inflation, the PPG sensor 264 is brought into tight contact with the ear canal skin for improved signal-to-noise measurement and further ensures good interfacial contact between the conductive electrodes 272 and 273, used to measure the neurophysiology electrical currents from the brain and the transcranial bioimpedances, and the ear canal epidermis. Note the ergonomic bend in the second silicone component 252 that mimics the first bend in the human ear-canal. The positioning of the IMU 262 on the device is illustrated in FIG. 2F.

Figure 3:
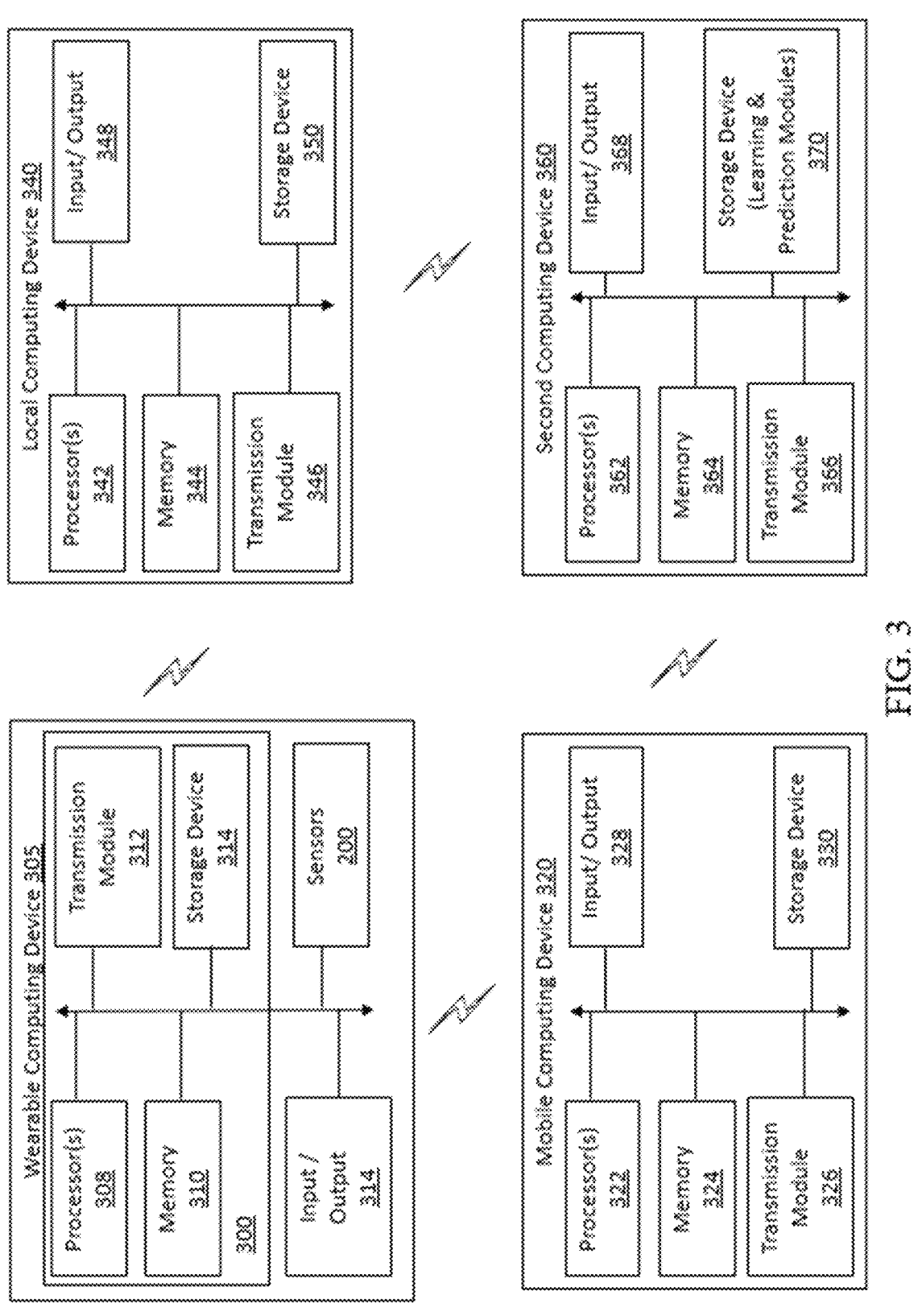
FIG. 3 illustrates an example computing environment of the system for non-invasive measurement of glymphatic flow, brain proteinopathy, and neurodegeneration that is comparable to molecular analyses or neuroimaging config-ured in accordance with the present invention.

FIG. 3 illustrates an embodiment of the previously described wearable device illustrated as wearable computing device 305, comprising the data storage, processing and transmission module 300 configured in accordance with the present invention and is not intended to limit scope as one of ordinary skill would understand on review of this application that other configurations could be utilized without departing from the scope of the claimed invention. Specifically, the data storage, processing, and transmission module 300 comprises one or more processors 308, a memory 310, a storage device 314, and a transmission module 312. The components of the data storage, processing, and transmission module 300 are responsible for storing the ear device sensor data, processing the data into preliminary measures of sensor impedance to determine that the sensors are correctly placed and the bladder is correctly pressurized, and transmitting the data for further off-line processing into measurements of brain proteinopathy and neurodegeneration that are comparable to molecular analyses or neuroimaging markers. The example of the wearable computing device 305 in FIG. 3 also illustrates the previously described sensors 200, such as an IMU and/or PPG, which gather data when positioned in the ears of a patient and which provide the data for storage in the storage device 314, processing by the processor 308, and transmission by the transmission module 312. The input/output device 314 can be a user interface in the form of buttons or a display screen. In other embodiments of the wearable computing device, the input/output device may be omitted.

The example embodiment of FIG. 3 illustrates the wearable computing device 305 capable of wireless communication via wireless links with a mobile computing device 320, such as a smartphone or tablet, and a local computing device 340, such as a desktop computer. It should be understood that it is not a requirement to have both a mobile computing device and a local computing device and in alternate embodiments only one of the mobile computing device 320 and local computing device 340 may communicate with the wearable computing device 305. As illustrated in FIG. 3, the mobile computing device 320 and the local computing device 340 comprise conventional components that are readily understood, including a processor 322/342, memory 324/344, a transmission module 326/346, an input/output interface 328/348, and a storage device 330/350. One or both of the mobile computing device 320 and the local computing device 340 can transmit the data collected by the wearable computing device 305 to a second computing device 360. The second computing device is typically located remotely and accessed via a wide area network such as the Internet. The second computing device can comprise computing components, such as a processor 362, memory 364, transmission module 366, input/output interface 368, and storage device 370. The storage device 370 can store various program modules that are executable by the processor 362. Specifically, the storage device 370 can comprise a learning software module and a prediction software module. For example, the learning software module can comprise a machine learning algorithm or deep learning algorithm that determines a function mapping from the collected neurophysiological and neurovascular data to a target marker of glymphatic clearance or neurodegeneration. The prediction module can comprise a model based on the function mapping that is used to predict glymphatic clearance or neurodegeneration based on sensor data that is newly collected by the wearable computing device from a patient.

Figure 4:
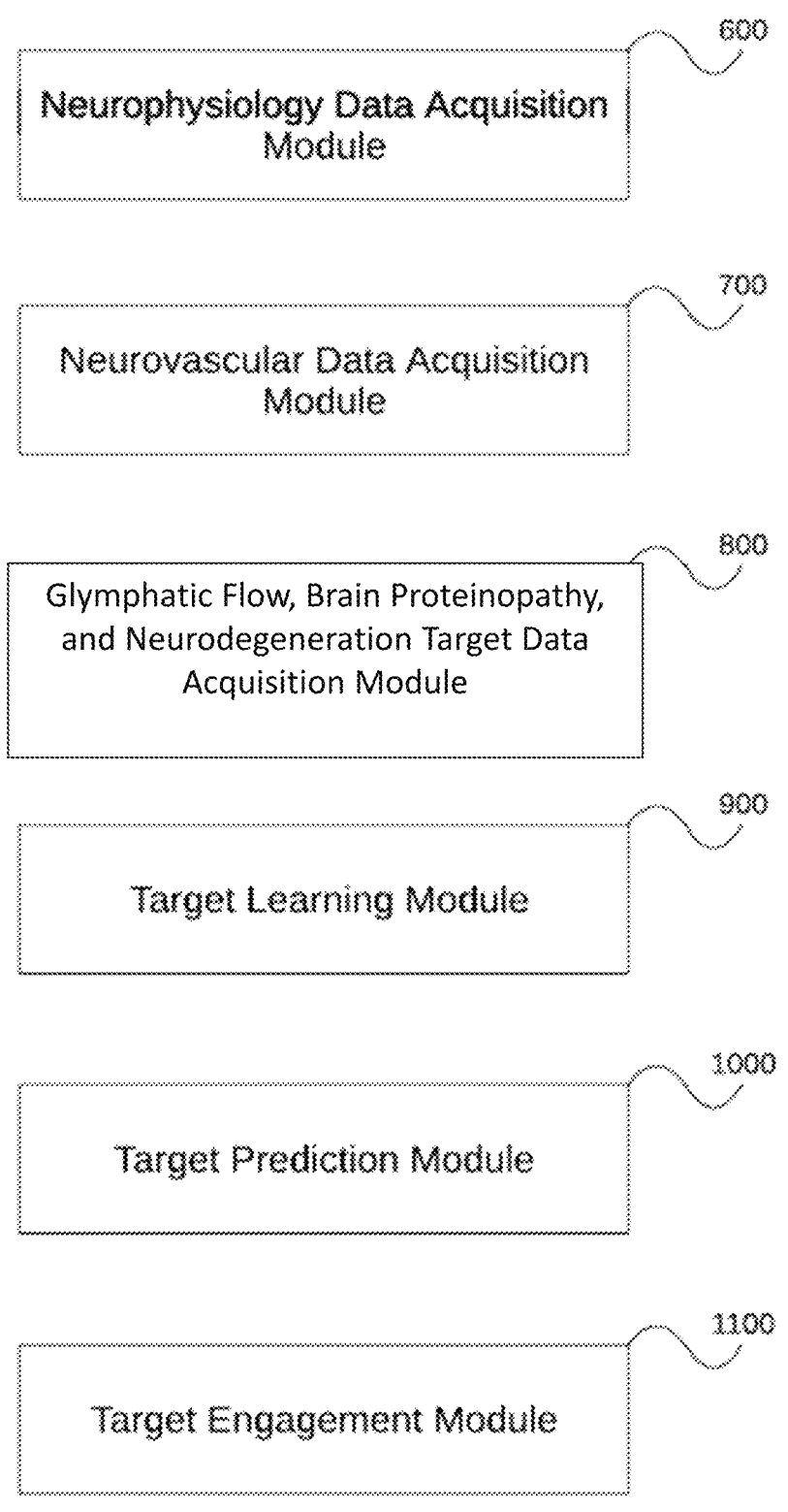
FIG. 4 is a functional description of the system in accor-dance with one embodiment of the present invention.
Figure 5:
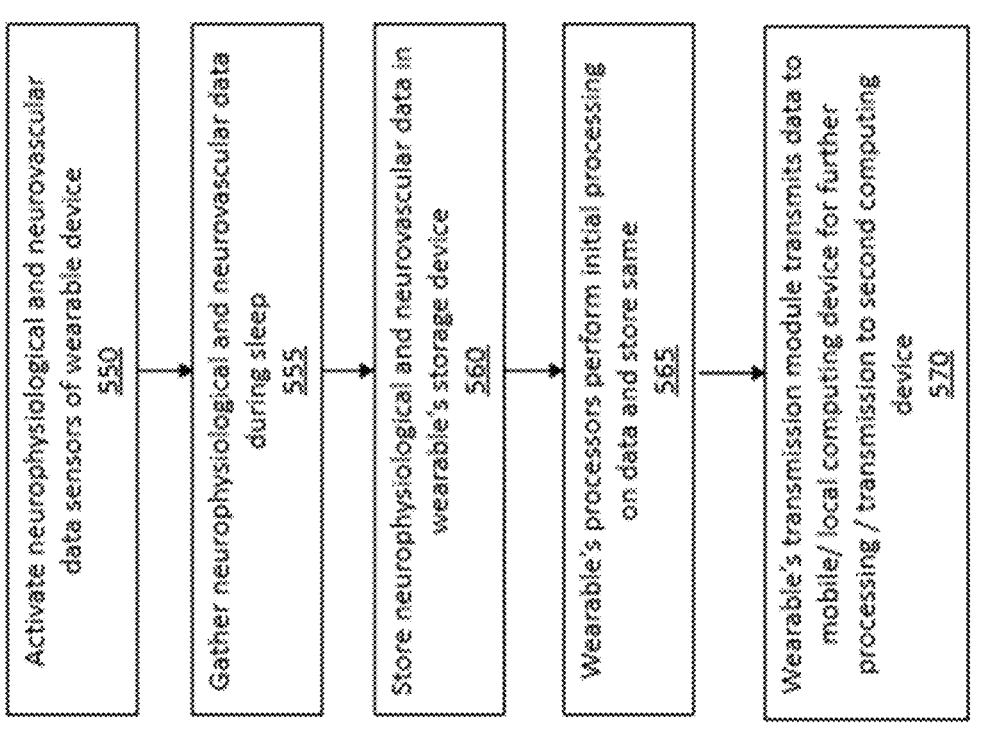
FIGS. 5A and 5B illustrate example methods associated with the collection of neurophysiology and neurovascular data from a wearable device for use in identifying, predict-ing, and treating neurodegeneration in accordance with one embodiment of the present invention.
Figure 5:
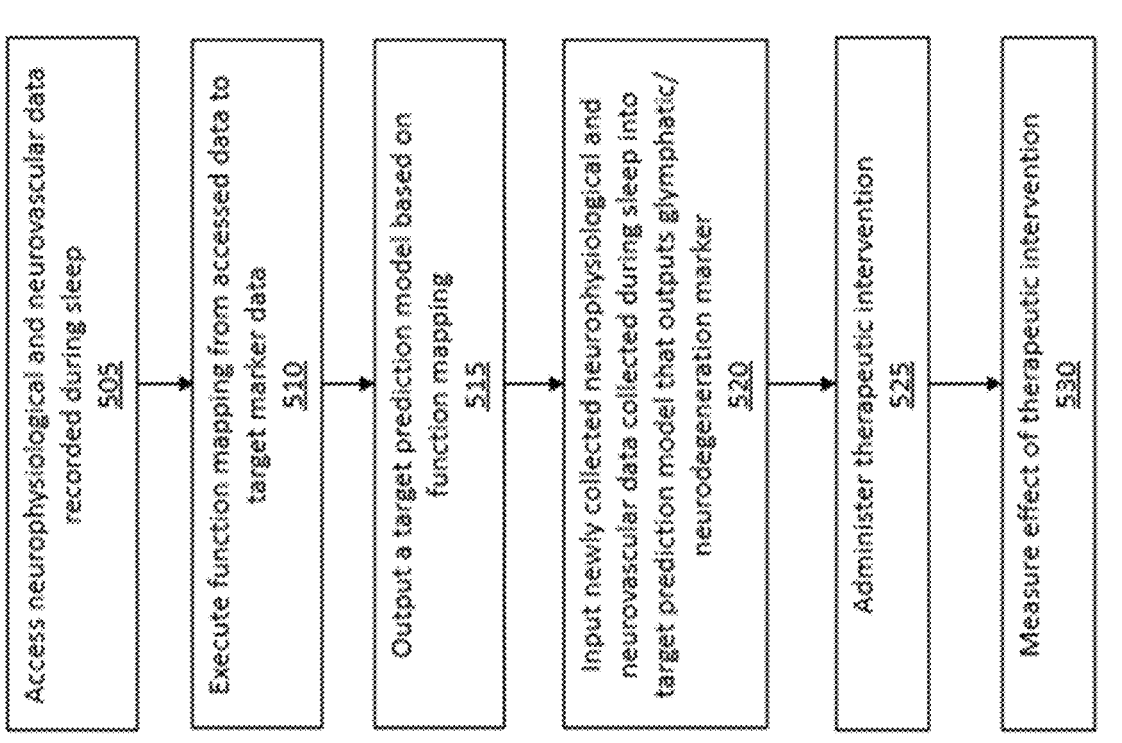

FIG. 4 illustrates an embodiment of the functional description of the system configured in accordance with the present invention and is not intended to limit scope as one of ordinary skill would understand on review of this application that other configurations could be utilized without departing from the scope of the claimed invention. Referring to FIG. 4, a user's sleep neurophysiology data is captured and recorded by the neurophysiology data acquisition module 600 through sensors positioned on the user's head, such as the previously described sensors positioned in the ear. The neurovascular data acquisition module 700 further captures the user's sleep neurovascular data through sensors positioned on the user's head. As explained previously, the neurophysiology data acquisition module 600 and the neurovascular data acquisition module 700 can be implemented in the wearable device.

In contrast, the brain proteinopathy and neurodegeneration target data acquisition module 800 is an invasive module typically implemented using sophisticated equipment at a medical facility and is responsible for acquiring one or more molecular analysis or neuroimaging markers of neurodegeneration. The marker of interest can be a CSF or plasma assay of one of several brain proteinopathy proteins including amyloid beta 42, tau, alpha-synuclein and neurofilament light that are markers of neurodegenerative disorders, a neuroimaging scan such as PET scan with a radiotracer for the protein of interest, an MRI with contrast agent to measure brain atrophy. The CSF assay or PET scan can be taken after sleep to assay an existing level of CSF protein or protein build up in the brain, or taken both before and after sleep to assay the net change in the protein level that occurred during sleep. The marker can also be an MRI with intrathecal contrast agent injected into the CSF prior to sleep and which is cleared via brain interstitial fluid transport into the meningeal lymphatic and cavernous sinus system during sleep, and the uptake and clearance rate measurable using repeat MRI scanning.

The target marker data measured by module 800 is used by the target learning module 900 to create a target prediction module 1000 that maps new neurophysiology data from module 600 and new neurovascular data from module 700 to a predicted molecular or neuroimaging marker of neurodegeneration for longitudinal monitoring without needing to repeat the invasive measurement of module 800. The target learning module 900 and target prediction module 1000 can be implemented as software that uses a machine learning or deep learning algorithm to provide an output. The target learning module 900 and target prediction module 1000 can be implemented as software executed on one or more remote computers such as the second computer described previously. Target prediction module 1000 can also map sleep neurophysiology data from module 600 and sleep neurovascular data from module 700 taken from a new patient to a molecular or neuroimaging marker of neurodegeneration for non-invasive screening that can be used in medical decision making to evaluate the need for the invasive measurement of module 800. The target engagement module 1100 measures the effect that a putative therapeutic intervention has on the sleep neurophysiology or neurovascular data, or degree of target engagement, and how that effect translates into a change in the predicted molecular or neuroimaging marker of neurodegeneration. The intervention can be one of cardiovascular, diet, sleep, pharmacological or neurostimulation.

FIGS. 5A and 5B illustrate embodiments of the present invention in the form of two methods and are not intended to limit scope as one of ordinary skill would understand on review of this application that other methods could be utilized without departing from the scope of the claimed invention. Referring to FIG. 5A, a method of creating and applying a target prediction model is illustrated. Beginning with operation 505, a processor of a computing device accesses neurophysiological and neurovascular data recorded while one or more patients were sleeping. The data can be recorded using the previously described wearable device or using other devices. In operation 510, the processor can use a learning software module to determine a function mapping between the recorded data accessed in operation 505 and target marker data. The learning software module can use a machine learning algorithm to determine the function mapping. The target marker data can be data indicating glymphatic flow within the brain. Alternatively, the target marker data can be one of a molecular analysis marker of neurodegeneration or a neuroimaging marker of neurodegeneration such as those described in association with module 800 of FIG. 4. After completing the function mapping, in operation 515 the learning software module outputs a target prediction module. The example method of FIG. 5A can end after operation 515 because the target prediction module can be used in a variety of ways. However, the example method of FIG. 5A continues with operations 520-530 to illustrate one application of the target prediction module. Specifically, in operation 520, neurophysiological and neurovascular data that is newly collected from a patient using the wearable device can be input into the target prediction model to generate a marker of glymphatic clearance or a marker of neurodegeneration. In operation 525, the marker that is output can be used to determine and administer a therapeutic intervention for the patient. In certain embodiments, information pertaining to the therapeutic intervention can be input into the wearable device. Lastly, after the therapeutic intervention has been administered, the wearable device can be used again in operation 530 to collect new data from the patient to determine the efficacy of the therapeutic intervention.

Referring now to FIG. 5B, an example method for operating a wearable device in accordance with the example embodiments of this disclosure is illustrated. Beginning with operation 550, the neurophysiological and neurovascular data sensors of the wearable device can be activated for gathering data while a patient sleeps with the wearable device attached to the patient's ears. For example, the processor of the wearable device can execute a data acquisition module stored in the wearable device's storage module, wherein the data acquisition module controls the operation of the sensors. In operation 555, the sensors of the wearable device, such as the IMU and/or PPG, gather neurophysiological and neurovascular data while the patient sleeps. In operation 560, the wearable device can store the gathered data in the storage device of the wearable device. In some instances, as indicated in operation 565, the wearable device's processor can perform certain initial signal processing on the data gathered by the sensors and store such processed data in the wearable device's storage device. Lastly, in operation 570, the transmission module of the wearable device can manage the transmission of the gathered and/or processed data from the wearable device via a wired or wireless communication link to one or both of a mobile computing device and a local computing device. The mobile computing device and/or local computing device can relay the data from the wearable device to a second computing device that can execute a learning software module and a prediction software module.

Figure 6A:
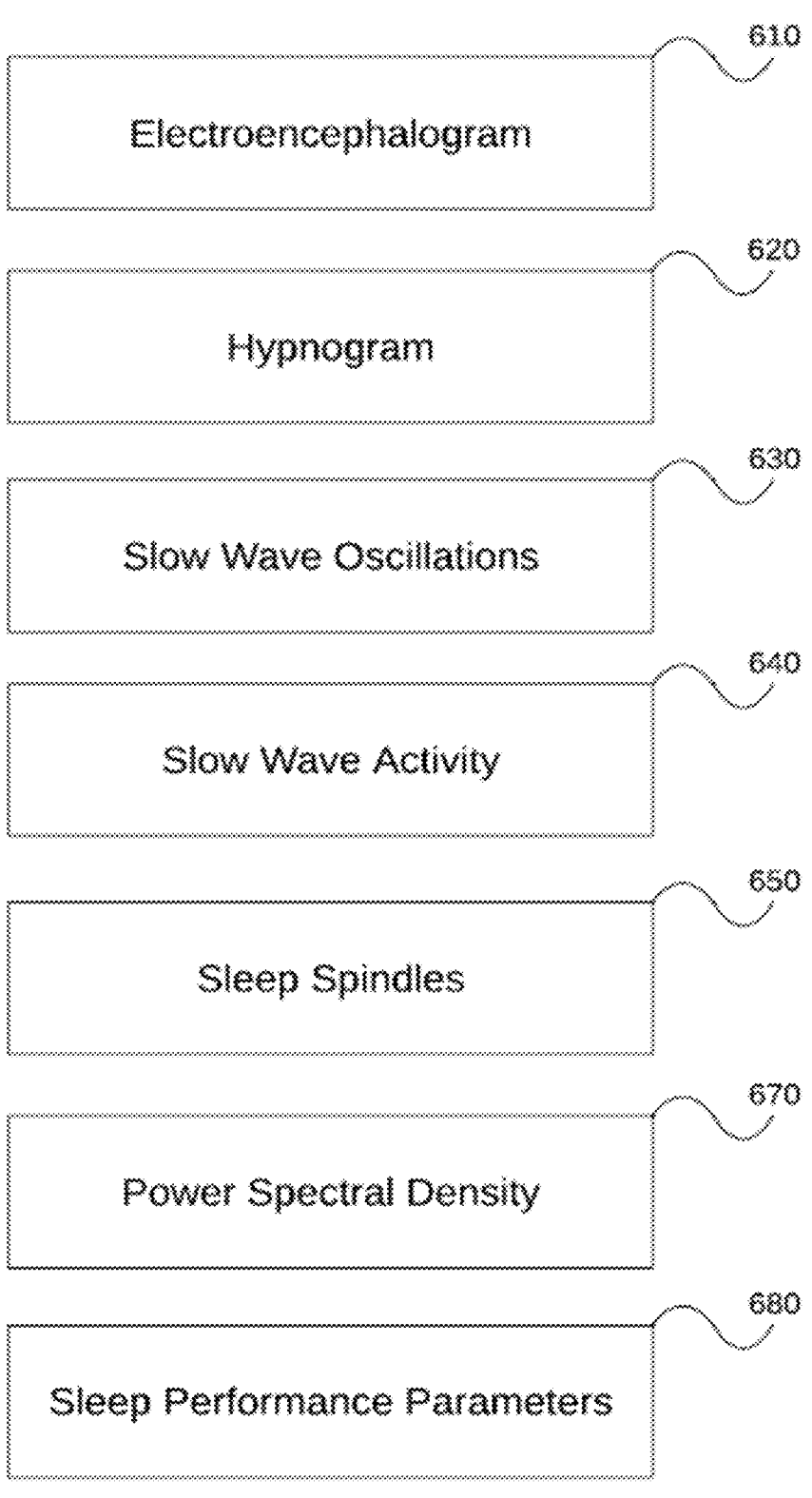

FIGS. 6A-6F illustrate an embodiment of the neurophysiology data acquisition module 600 of the system configured in accordance with the present invention and is not intended to limit scope as one of ordinary skill would understand on review of this application that other configurations could be utilized without departing from the scope of the claimed invention. Referring to FIG. 6A, in 610 raw EEG data is acquired from the user during sleep. The EEG data can be acquired using conventional EEG headcap sensors with a bedside amplifier for recording the signals, or using a wearable device with integrated electronics for amplifying and recording the signal. From the raw EEG signal, various derivations can be analyzed to generate a hypnogram 620 that marks the four stages of sleep, N1, N2, N3 and rapid eye movement (REM) from which additional sleep performance parameters 680 can be derived including total sleep time, sleep onset latency, wake after sleep onset, sleep efficiency and number of awakenings. In 630, slow wave oscillations in the raw EEG signal are detected and the density (number per minute), amplitude and duration of these oscillations are reported in 30 or 60 second epochs during sleep. In 640, slow wave activity defined as the relative or absolute power in the EEG signal in the frequency band between 0.5 Hz and 4.5 Hz is computed for every 30 or 60 second epoch and reported. Options for computing the power spectrum include a fast Fourier transform, Welch's periodogram or the multitaper method. In 650, another sleep EEG element, sleep spindles, are detected in one or more EEG derivations. Sleep spindles occur in two types, fast and slow, depending on the spindle frequency. Spindle density, frequency, duration and amplitude is reported in 30 or 60 second epochs for each type. Both slow wave oscillations or activity, 630 and 640, and sleep spindles 650 are sleep microstructure markers of glymphatic flow. Finally, in 670 the full power spectral density in the EEG signal is computed in 30 or 60 second epochs and reported.

One or more of the EEG data elements illustrated in FIG. 6A can be used in connection with the target prediction model. For example, the EEG data elements illustrated in FIG. 6A can be used to train the target prediction model. As another example, if the EEG data elements are data that is newly collected after the target prediction model is trained, the EEG data elements can be input into the target prediction model to predict new target markers of neurodegeneration.

Figure 6B:
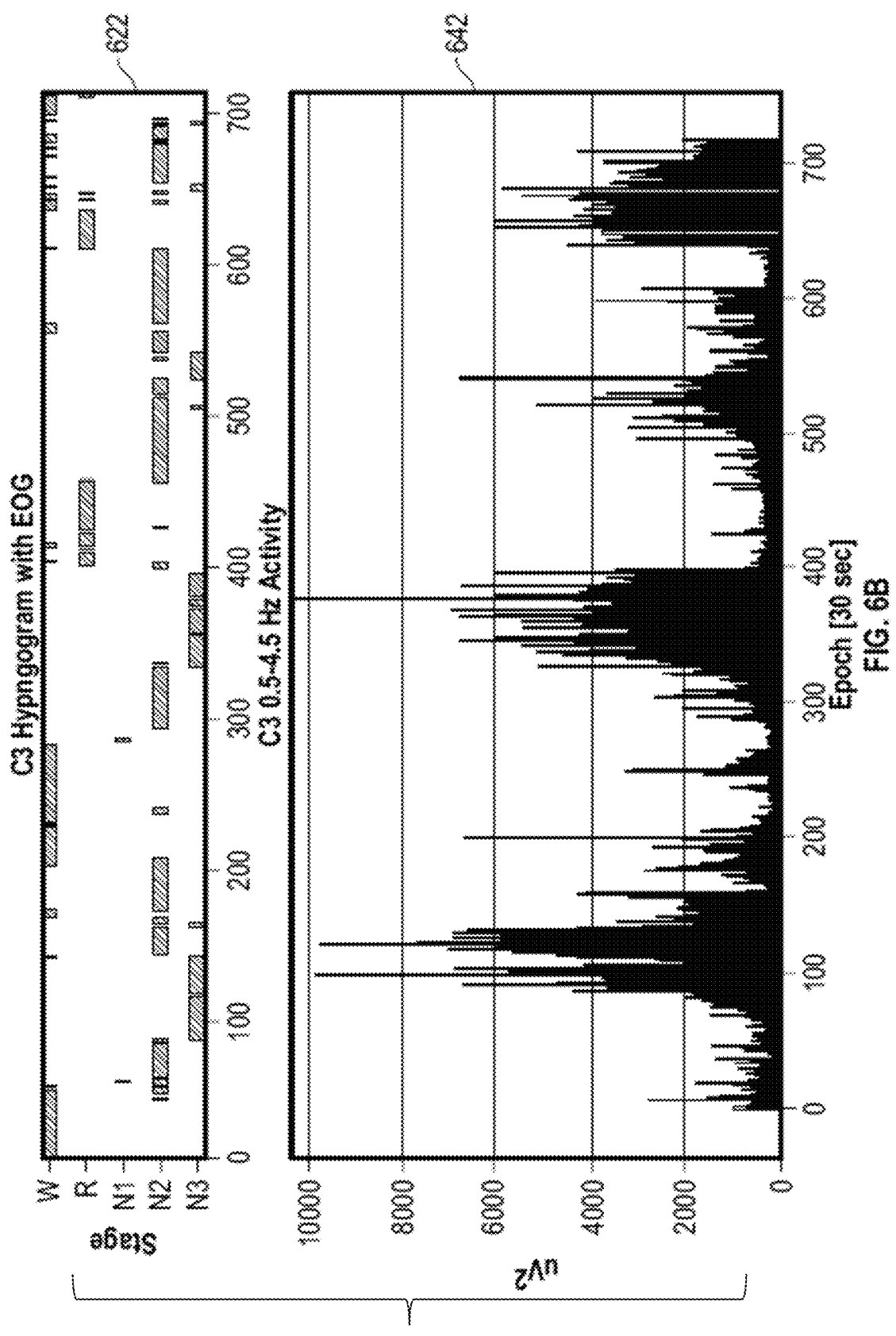

Referring to FIG. 6B, 622 is an example sleep hypnogram from an individual during one night EEG recording using a standard 10-20 scalp wet-sensor montage and the results of a C3 to M1 derivative is shown. The sleep hypnogram shows when the individual was awake (W) and in stage N1, N2, N3 or REM sleep in each 30 second epoch. In 642 is illustrated the slow wave activity in the 0.5 to 4.5 Hz bandwidth using a Welch periodogram in 30 second epochs. The slow wave activity is seen to peak during N3 sleep. Important features of the slow wave activity include duration, power and frequency that can be used in connection with the target prediction model. For example, the features of the slow wave sleep elements illustrated in FIG. 6B can be used to train the target prediction model. If the EEG slow wave sleep elements are data that is newly collected after the target prediction model is trained, the EEG slow wave sleep data elements can be input into the target prediction model to predict new target markers of neurodegeneration.

Figure 6C:
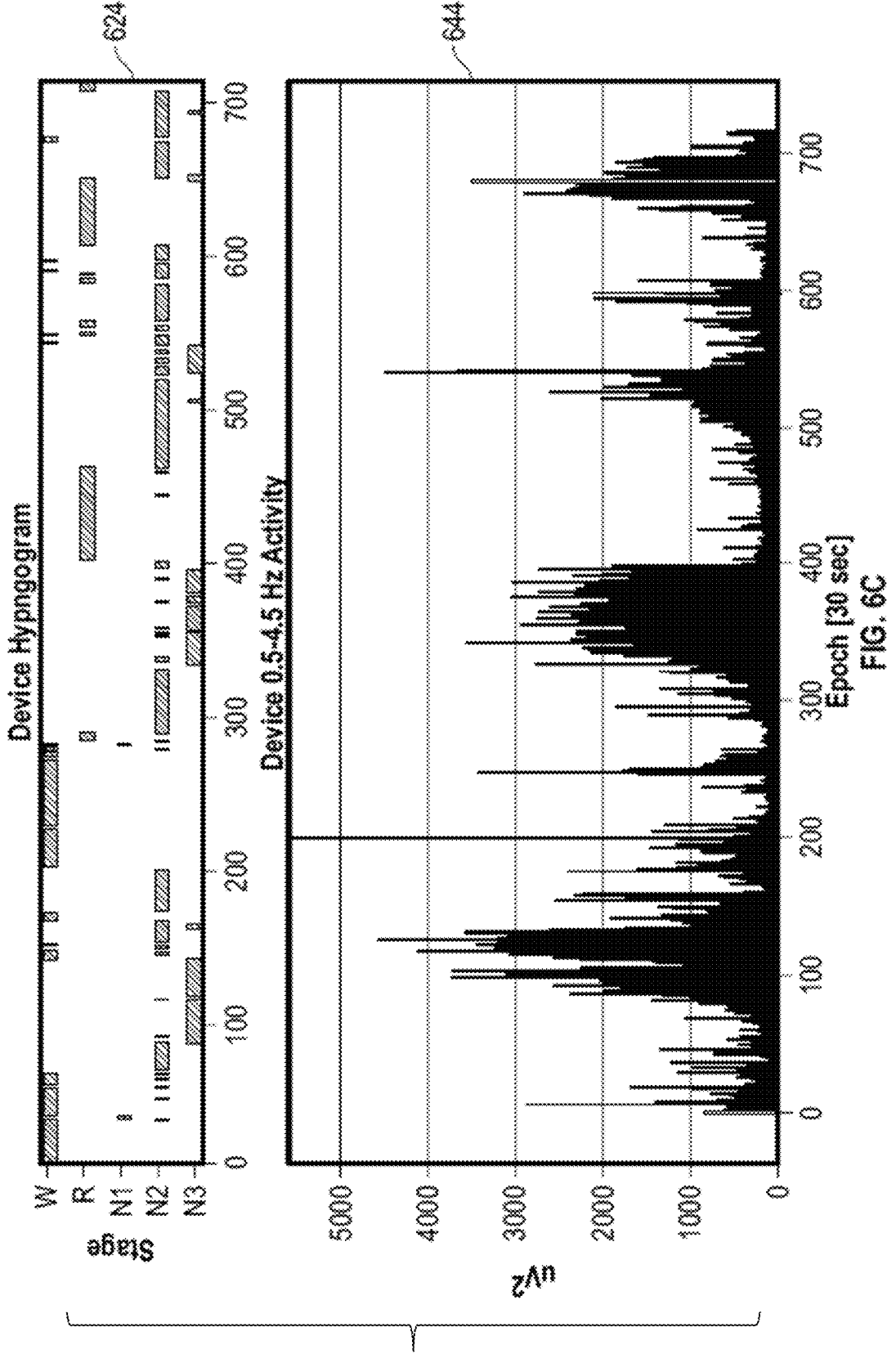

During the same night and for the same individual, simultaneous recordings were made using an ear device comprising modules 100, 200 and 300 illustrated in FIG. 1A. In FIG. 6C, 624 shows the sleep hypnogram recorded by the ear device and 644 shows the slow wave activity in the 0.5 to 4.5 Hz bandwidth using a Welch periodogram and 30 second epochs.

Figure 6D:
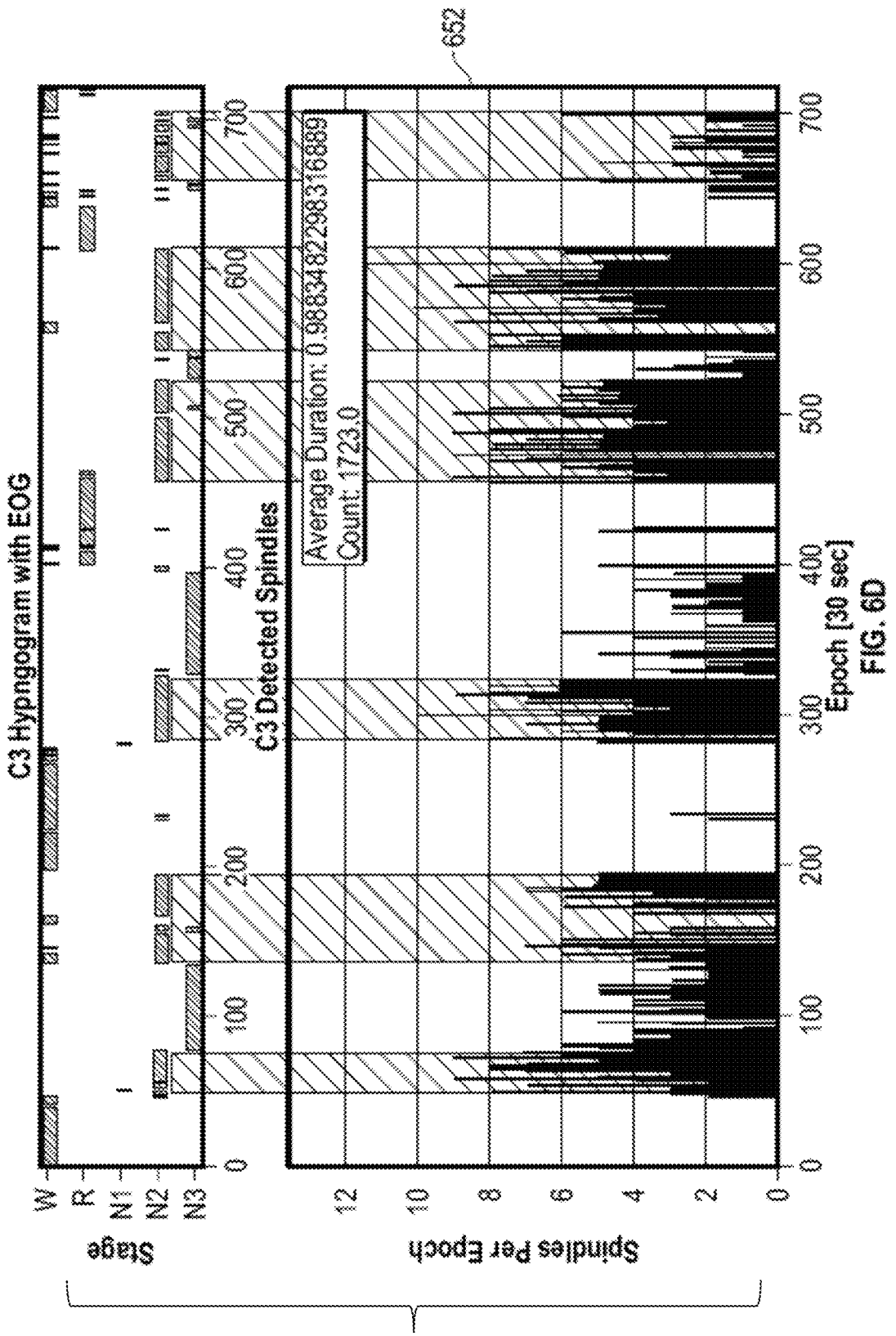

Referring to FIG. 6D, for the same individual during the same night of EEG recording, sleep microstructure spindle activity in the 10 to 16 Hz bandwidth using a Welch periodogram in 30 second epochs are illustrated in 652 from the standard 10-20 scalp wet-sensor montage using a C3 to M1 derivative. In 654 is illustrated the same analysis using the sensors from the ear device comprising of modules 100, 200 and 300 illustrated in FIG. 1A. In both illustrations, peak spindle activity is seen to coincide with stage N2 sleep. Important features of spindle activity include duration, power and frequency. For example, the features of the sleep spindle elements illustrated in FIG. 6D can be used to train the target prediction model. If the EEG sleep spindle elements are data that is newly collected after the target prediction model is trained, the EEG sleep spindle data elements can be input into the target prediction model to predict new target markers of neurodegeneration.

Figure 6E:
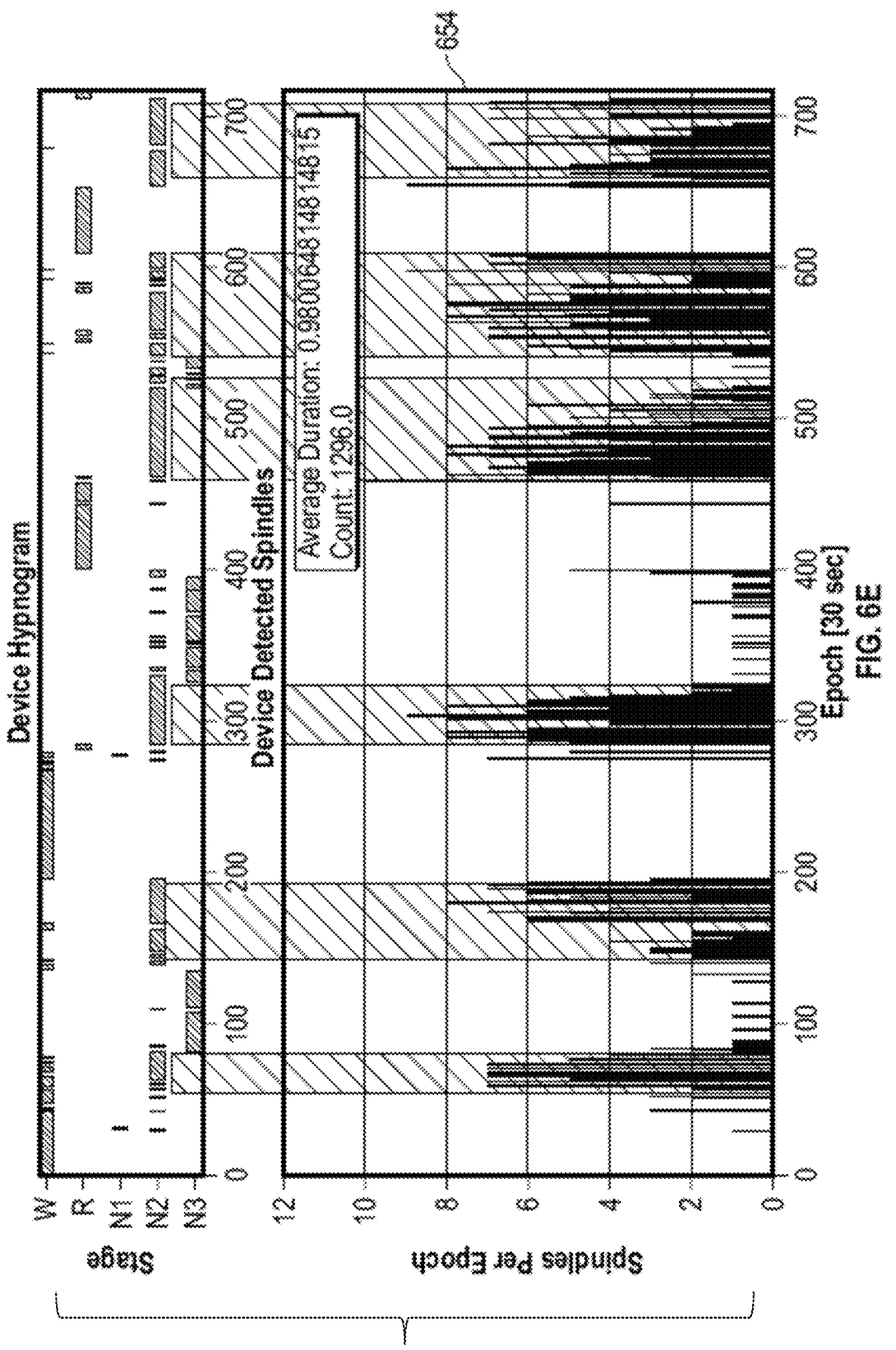

For the same individual during the same night of EEG recording, FIG. 6E illustrates the sensitivity agreement on hypnogram stages and sleep performance parameters between different EEG electrode positions. Illustrated in 682 of FIG. 6F are the sensitivity agreement of hypnogram stages between the C3 to M1 derivative to score the hypnogram and the derivative between the left and right ear electrodes in FIG. 1A illustrated in 200. Illustrated in 684 of FIG. 6F are the agreement in sleep performance parameters derived from the sleep hypnograms between the C3 to M1 derivative to measure the hypnogram and the derivative between the left and right ear electrodes in FIG. 1A illustrated in 200. The differences in sensitivity agreement and performance parameters are due to the anatomical differences in the sensor location for measurement highlighting the importance of consistent anatomical sensor placement between uses and across users to extract sleep EEG features for the training the target prediction model and as new inputs to a trained target prediction model to make predict new target markers of neurodegeneration. In-ear lead placement as done by the wearable ear device illustrated in FIG. 1A using anatomically informed ear fittings shown in FIGS. 2C-2G ensure consistent anatomical placement by a user.

Figure 7A:
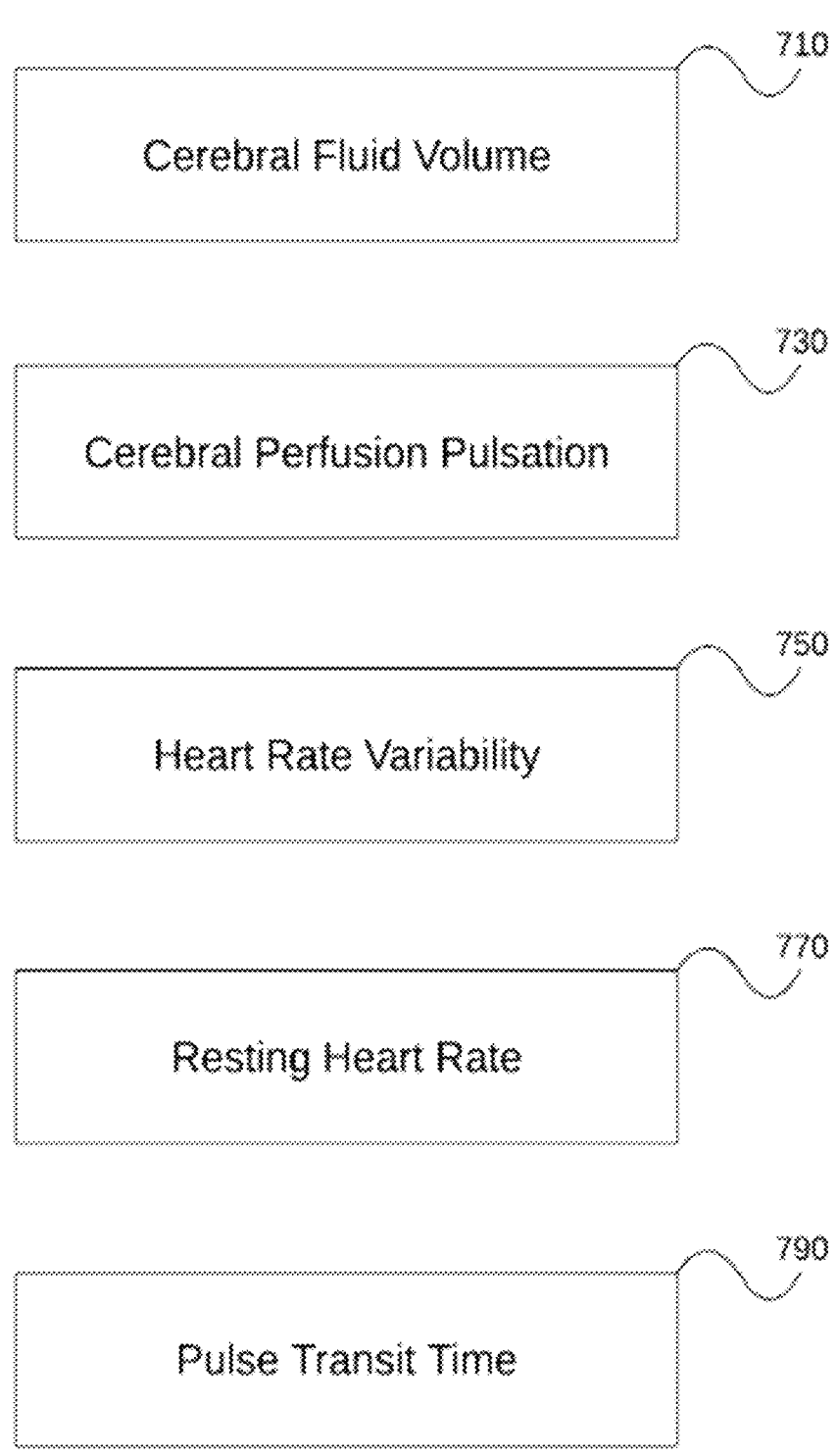
FIGS. 7A-7E illustrate the neurovascular data acquisition module and example associated data in accordance with one embodiment of the present invention.

FIG. 7A-7E illustrates an embodiment of the neurovascular data acquisition module 700 of the system configured in accordance with the present invention and is not intended to limit scope as one of ordinary skill would understand on review of this application that other configurations could be utilized without departing from the scope of the claimed invention. Referring to FIG. 7A, the same sensors 272 and 273 illustrated in FIG. 2G used for recording in-ear EEG are multiplexed to record at 80 kHz, well above EEG bandwidth, transcranial impedance from left to right ear during sleep. Transcranial impedance tracks fluid changes in the brain that arise during sleep, for example from sleep related changes in glymphatic flow and cerebral spinal fluid production, illustrated in module 710, and from cardiac pulsations, leading to a beat-to-beat measurable cerebral perfusion pulsation illustrated in module 730. With each heartbeat, a large fraction of the cardiac output is ejected into the internal carotid and vertebral arteries and delivered to the brain parenchyma. This change in brain blood volume lowers the transcranial impedance and is measurable by the sensors. The amplitude of the impedance waveform and the numerical integration of the impedance waveform pulse are proportional to the volume of blood that is ejected into the brain during that cardiac cycle. The moving average of the transcranial impedance during sleep drifts lower. This drift corresponds to a diurnal fluctuation in brain fluid volume with increased fluid volume during sleep from, for example increases in glymphatic flow and cerebral spinal fluid production, and is measurable by module 710. A larger drop between onset of sleep and the sleep nadir of the transcranial impedance correlates with a larger increase in total brain fluid composition that would be expected with greater glymphatic flow. The pulsations recorded by module 730 assist fluid flow through the brain interstitial spaces that promotes glymphatic flow during sleep and protein clearance. The larger magnitude of these pulsations, measured as either their amplitude or numerically integrated area measuring ejection volume, is expected to propel greater glymphatic flow leading to improved clearance. Photoplethysmography sensors located in the ear on the device illustrated in FIG. 1A and illustrated 264 in FIG. 2F, record heart rate variability during sleep in module 750, resting heart rate by module 770 and sinus arrythmia that can be used to estimate breathing rate also by module 770. Heart rate variability during sleep measures the sympathetic-parasympathetic tone of the autonomic nervous system, with lower heart rate variability indicating lower parasympathetic tone and higher sympathetic tone. During sleep, higher sympathetic tone activated by the locus coeruleus in the brain decreases brain interstitial fluid flow and protein biomarker clearance. Higher sleep heart rate variability is expected to lead to greater glymphatic flow and protein clearance. Lower sleep resting heart rate recorded by module 770 is compensated by higher cardiac stroke volume to maintain a tightly regulated cerebral blood flow. A higher cardiac stroke volume results in larger cerebral perfusion pulsations that are measurable by module 730 and increase the propelling forces of glymphatic flow. Conversely, diseases that harden arteries, in particular the arterioles that penetrate the brain parenchyma alongside which run the paravascular spaces containing cerebrospinal fluid that is propelled into the brain parenchyma to drive glymphatic flow, decrease the propelling forces. A decrease in the propelling force is measured by a decreases in the magnitude of the cerebral perfusion pulsation in module 730. Changes in respiratory rate recorded in module 770 also alters the blood volume pulsations in 730 by affecting venous return to the heart and thereby changing cardiac stroke volume.

One or more of the neurovascular data elements illustrated in FIG. 7A can be used in connection with the target prediction model. For example, the neurovascular data elements illustrated in FIG. 7A can be used to train the target prediction model. As another example, if the neurovascular data elements are data that is newly collected after the target prediction model is trained, the neurovascular data elements can be input into the target prediction model to predict new target markers of neurodegeneration.

Figure 2G:
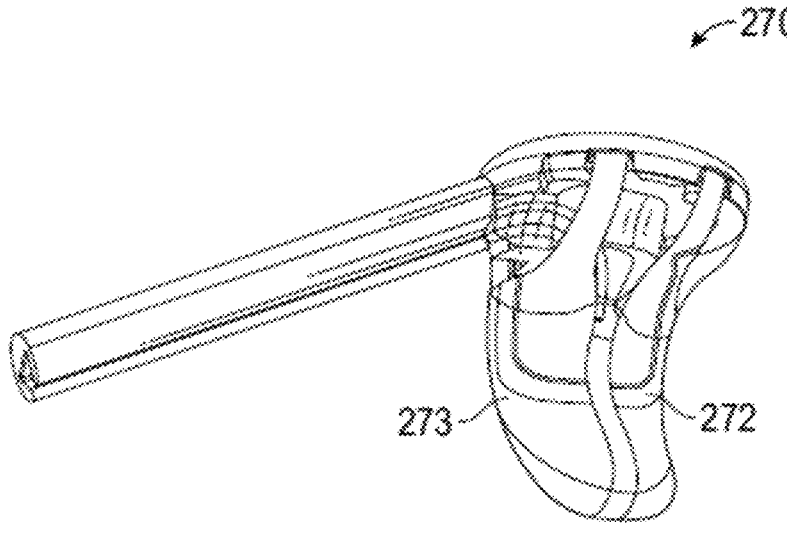
Figure 7B:
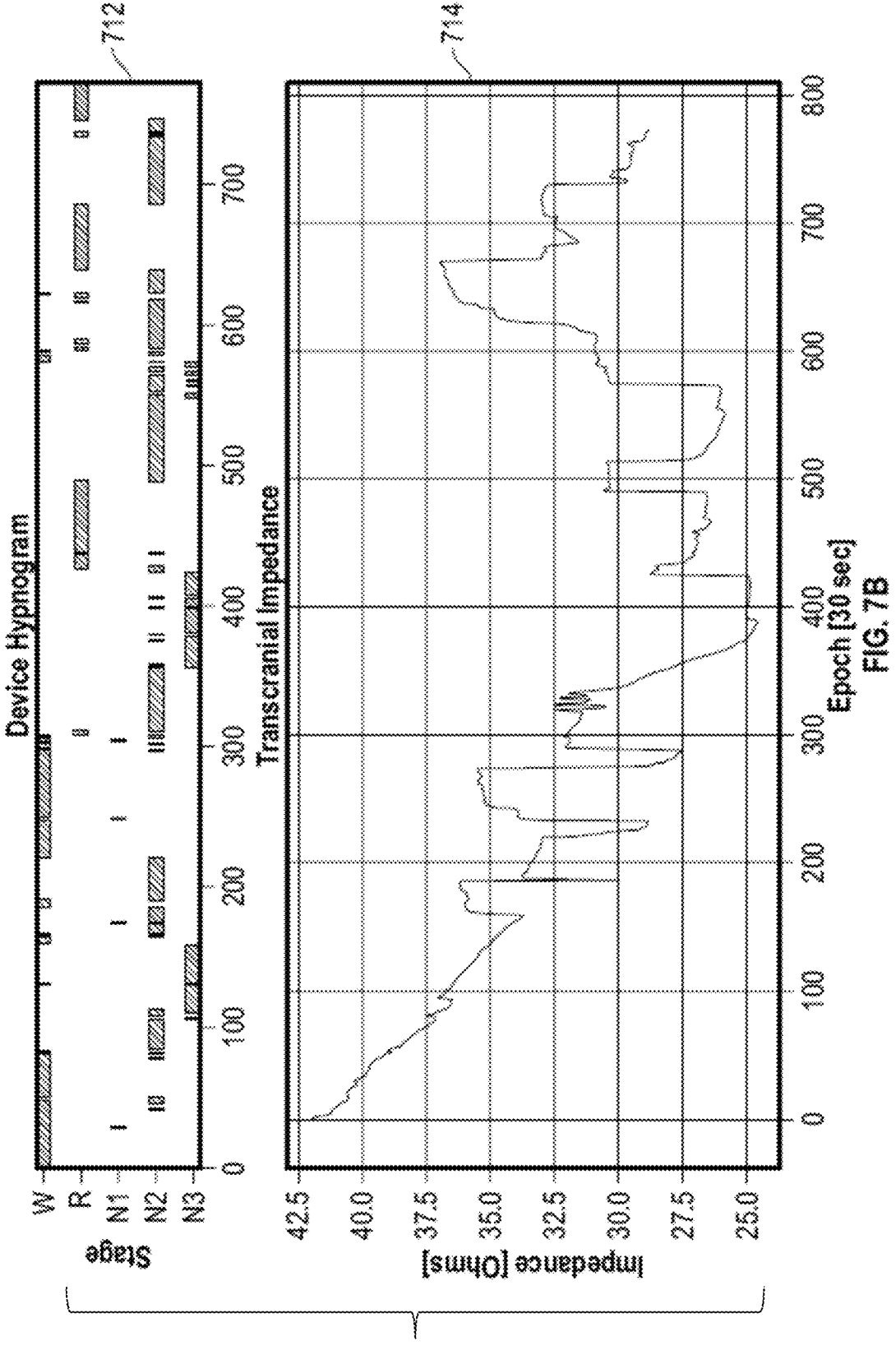
Figure 7B:
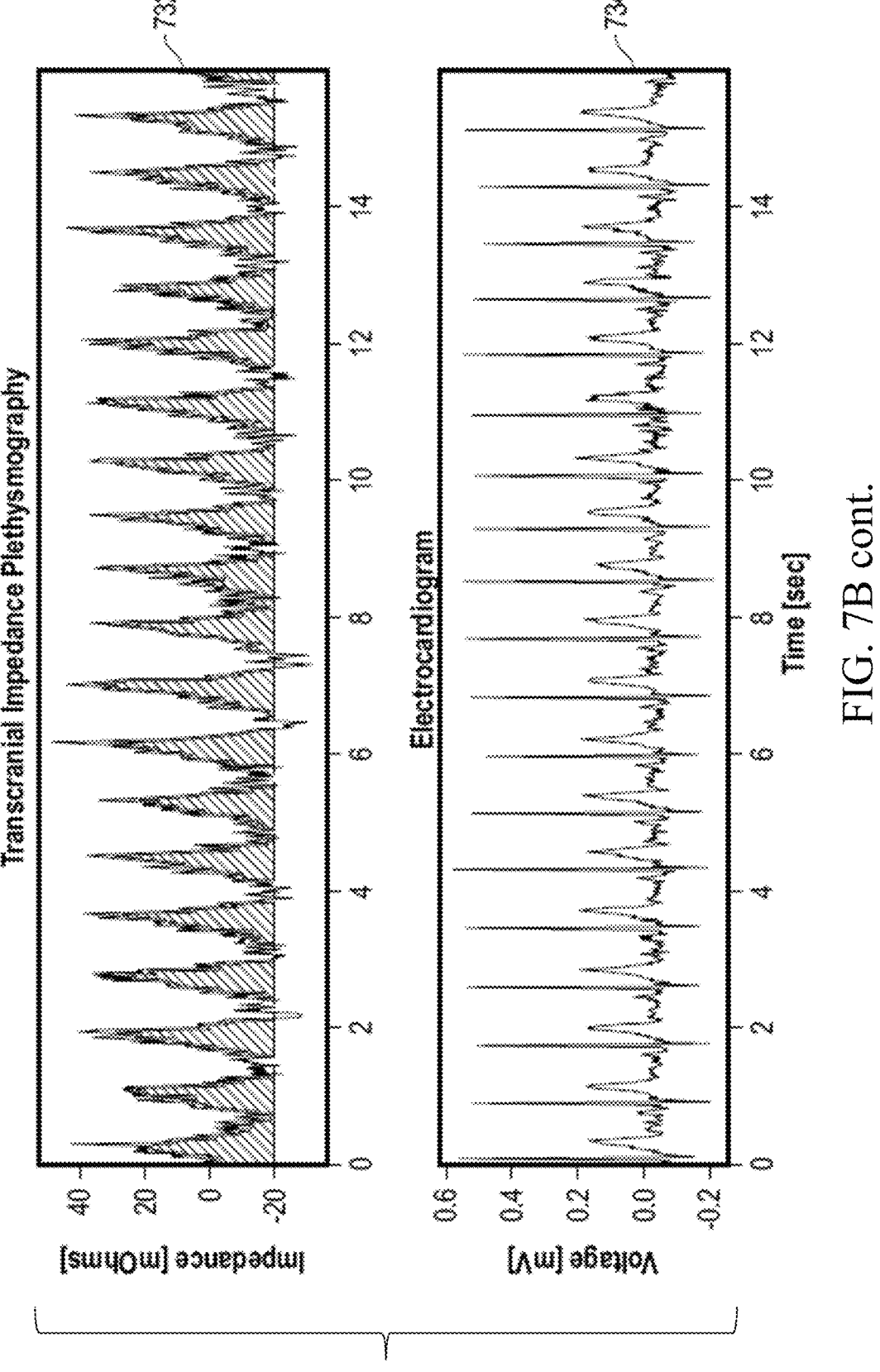

Referring to FIG. 7B, 714 shows a sleep recording of the cerebral fluid volume from the transcranial impedance sensors illustrated by 272 and 273 in FIG. 2G for the left in-ear device. The sleep hypnogram illustrated in 712 corresponds to the recorded impedance 714 and shows the decrease in impedance as the patient progresses to deep sleep in stage N2 and N3 (slow wave sleep). The drop in impedance corresponds to an increase in fluid (or water) composition in the brain that corresponds to increase in glymphatic flow through the brain tissue and an accompanying increase in the production of cerebrospinal fluid.

An interval of cerebral perfusion pulsation during sleep for this patient is illustrated in 732 and the corresponding ECG signal in 734. The cerebral perfusion stroke volume is the difference in impedance between the peak and the trough of a pulsation. A larger difference signifies a greater change in fluid, or water, composition resulting from the heart beat and correlates directly with cerebral stroke volume.

Figure 7C:
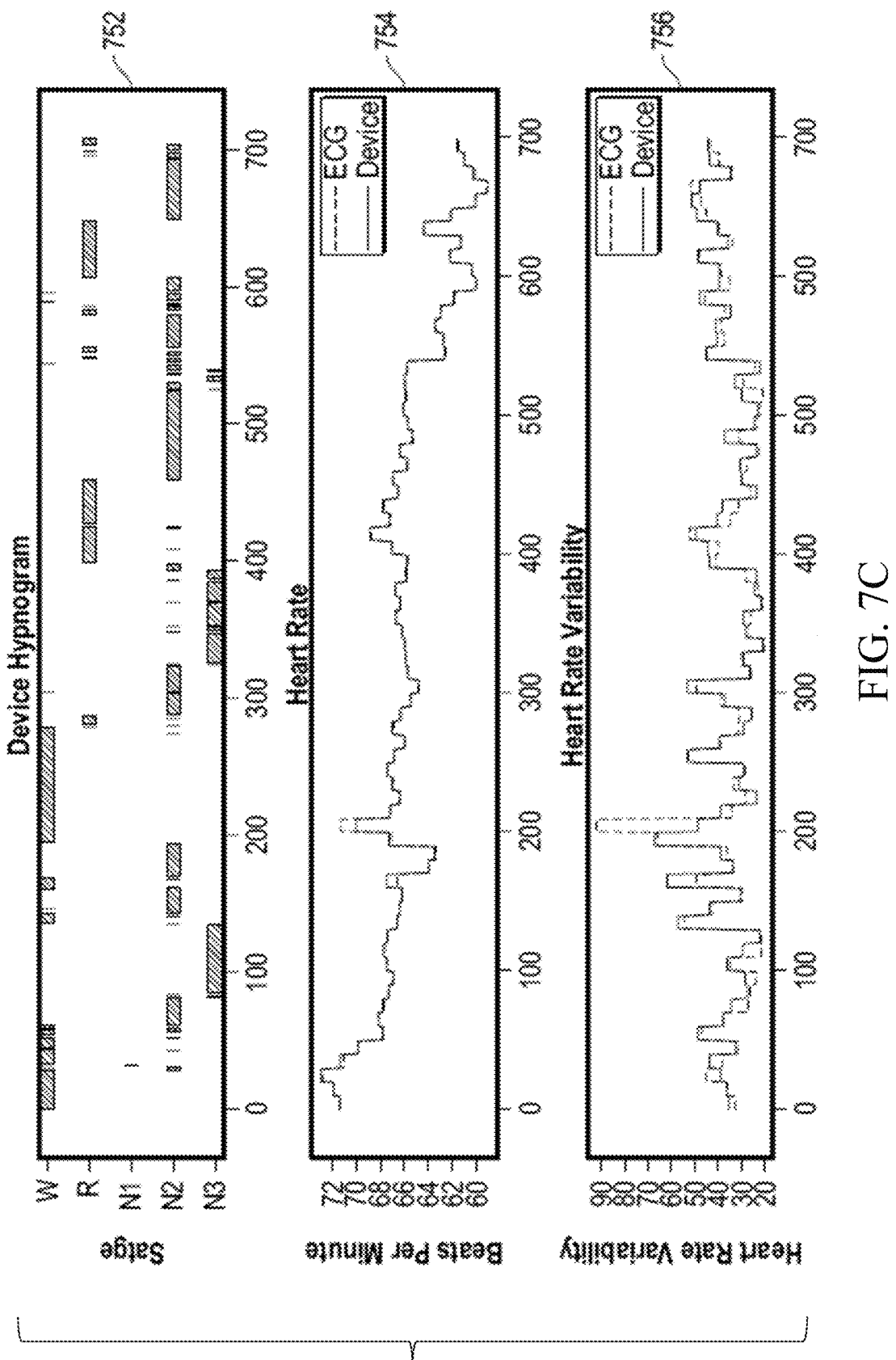

Referring to FIG. 7C, for each 500 second epoch during sleep, the sleep hypnogram is illustrated in 752, a recording of resting heart rate by module 770 is illustrated in 754 and a recording of resting heart rate variability by module 750 is illustrated in 756, where in both 754 and 756 are illustrated the recording from the sensors by the wearable device illustrated in FIG. 1A against gold-standard electrocardiogram (ECG) recordings.

Figure 7D:
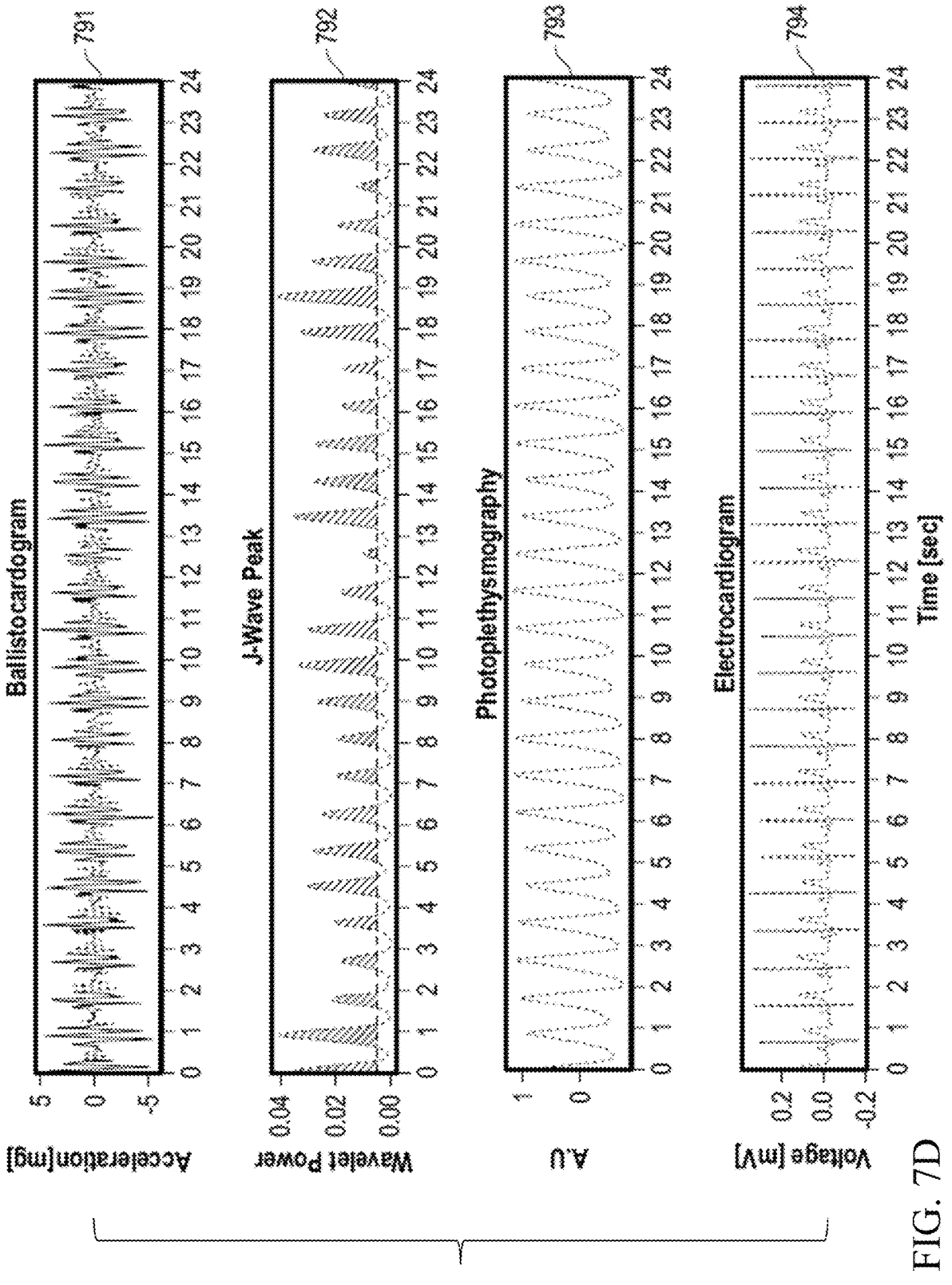

Referring to FIG. 7D, the pulse transit time module 790 records a ballistocardiogram (BCG) 791 from the in-ear inertial measurement unit (IMU) illustrated by 262 in FIG. 2F. The BCG I, J and K waveforms are highlighted in the recording 791. Using a wavelet analysis of the BCG recording, the power of the J waveform is illustrated in 792, with its peak aligning with the J waveform peak of the BCG. Illustrated in 793 is the PPG waveform recording from the in-ear sensor 264 illustrated in FIG. 2F and 794 illustrates the ECG recording. The IMU, PPG and ECG recordings are time-synchronized by module 790. A 2.5 second duration close-up of the data illustrated in 791-794 is illustrated in

Figure 7E:
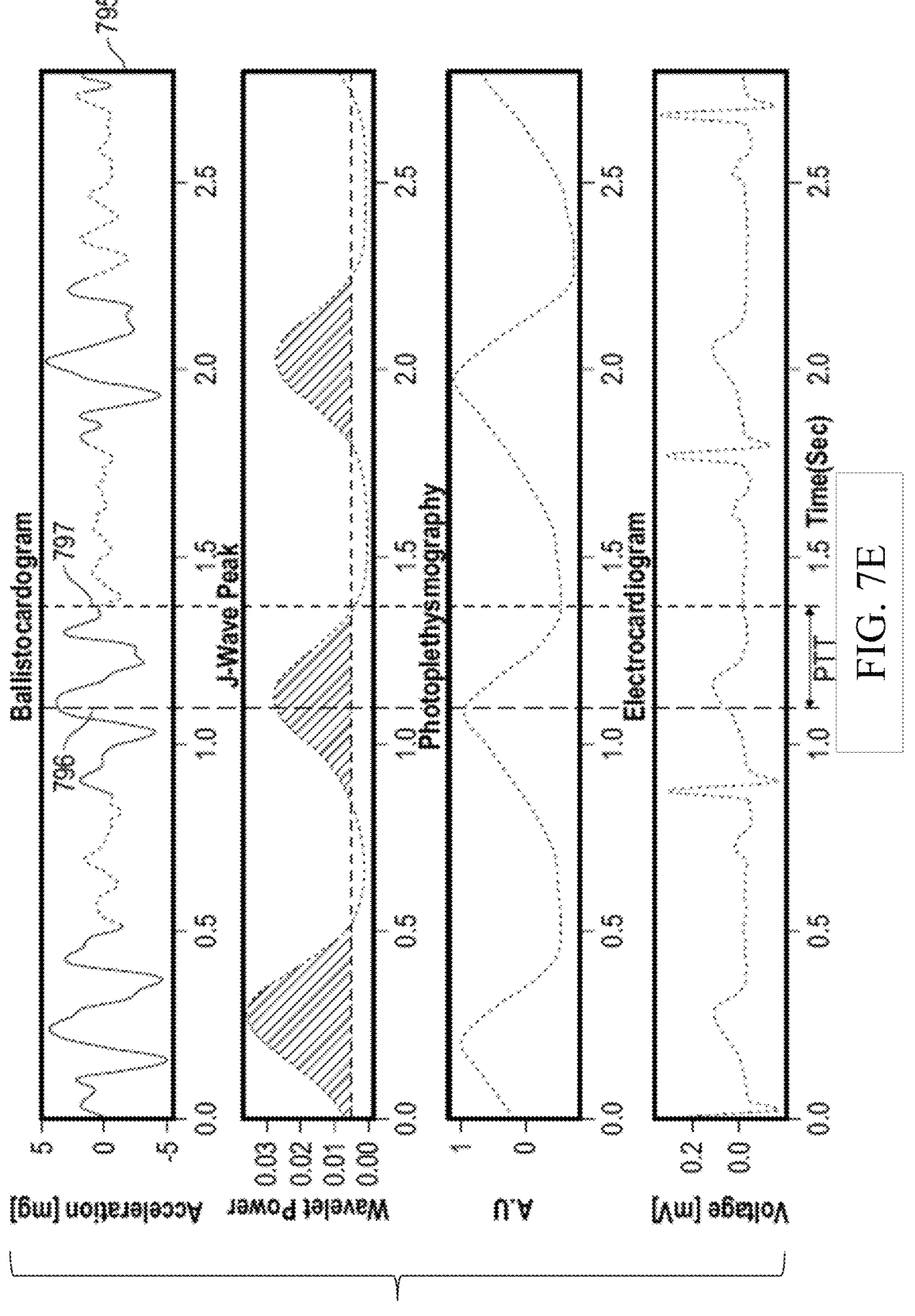

795 of FIG. 7E. Computation of the pulse-transit time of a cardiac ejection is illustrated in 795. The maximum blood acceleration is marked by the BCG J-wave 796 and trough of the PPG waveform 797 corresponds to the timing capillary blood engorgement in the ear resulting in a reduction in infrared scatter to the PPG collector. The difference between the timings illustrated in 797 and 796 for that one cardiac cycle is the pulse transit time from the aortic valve to the in-ear sensor. The pulse-wave velocity can be calculated as the vascular distance travelled by the blood from the aortic valve to the in-ear sensor divided by the pulse-transit time. In adults that distance stays fixed and changes in pulse-transit time are inversely related to changes in pulse-wave velocity.

Figure 8A:
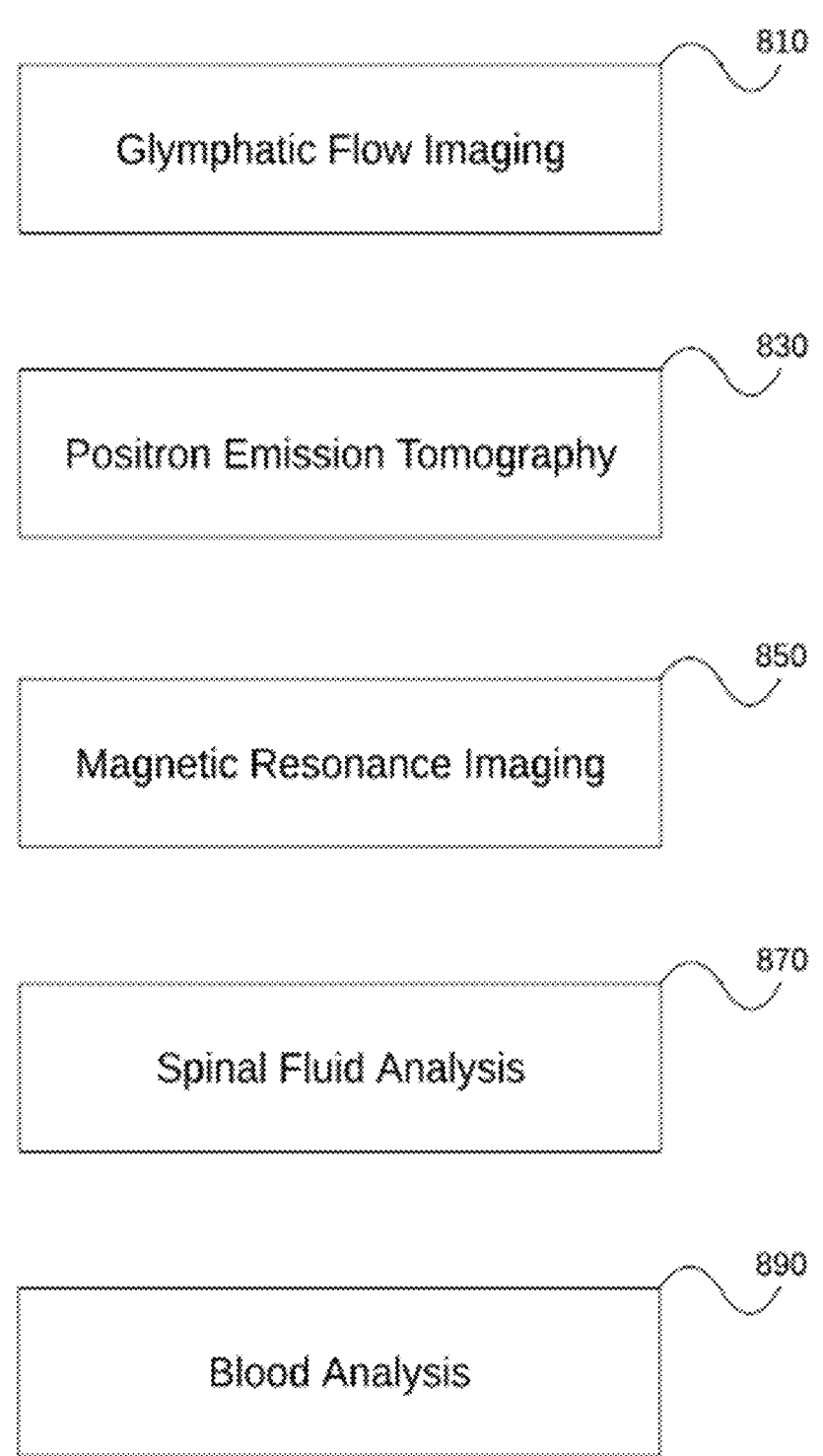
FIGS. 8A-8B illustrate the data acquisition module for a marker of glymphatic flow, a molecular analysis marker or a neuroimaging marker of neurodegeneration and associated images in accordance with an embodiment of the present invention.
Figure 8B:
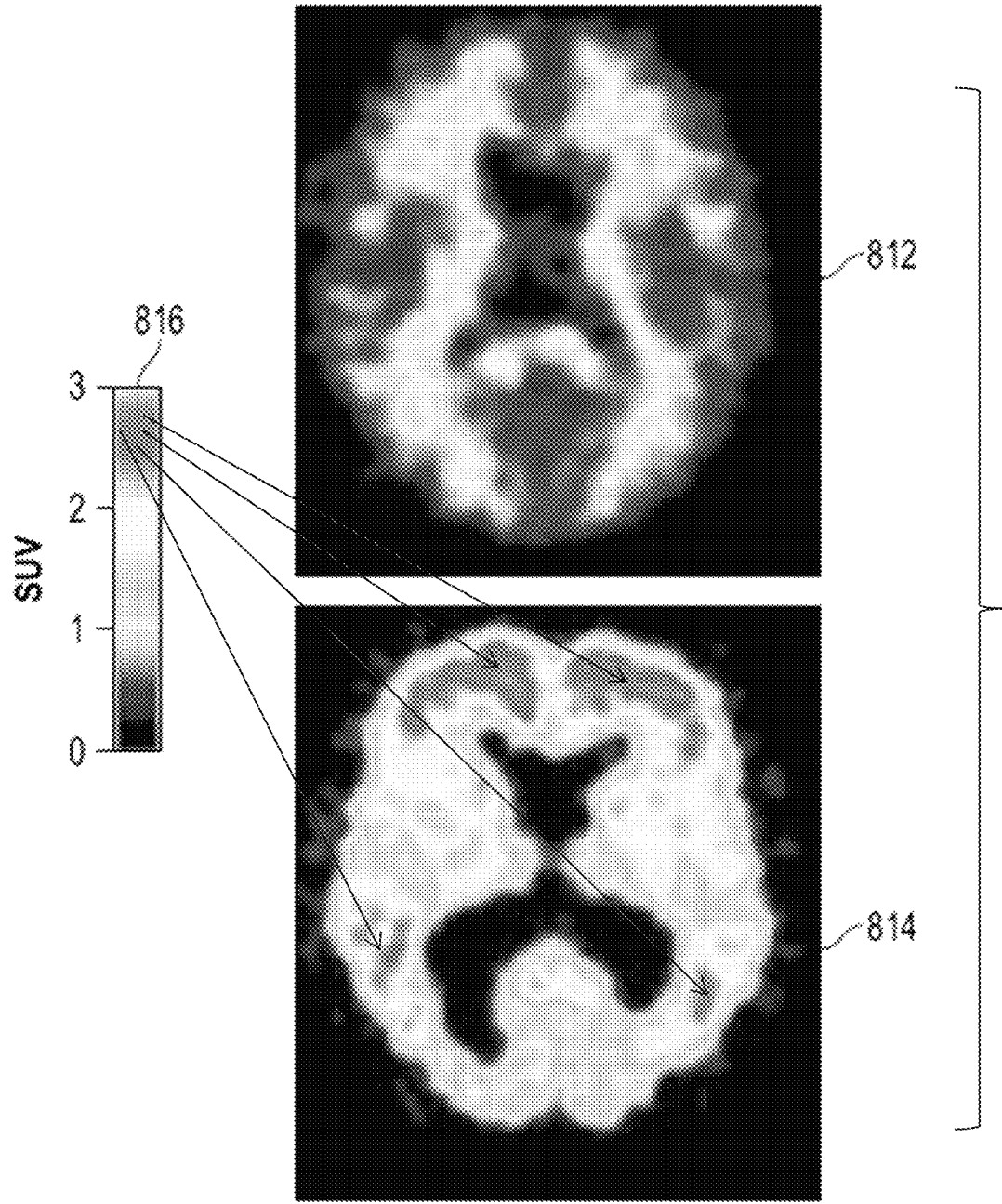

FIGS. 8A and 8B illustrate an embodiment of the glymphatic flow, brain proteinopathy and neurodegeneration target data acquisition module 800 of the system configured in accordance with the present invention and is not intended to limit scope as one of ordinary skill would understand on review of this application that other configurations could be utilized without departing from the scope of the claimed invention. Referring to FIG. 8A, in one embodiment 810, glymphatic flow imaging can be used with diffusion tensor MRI to measure the glymphatic flow of CSF in the perivascular spaces or can be used with a CSF tracer such as gadolinium that when injected intrathecally is cleared through the brain's extravascular, glymphatic flow, transport. Timing the injection just before the onset of sleep, an MRI scan can be done prior to sleep and once again at the end of sleep. The difference in the intensity of the contrast agent in key regions of interest provides a neuroimaging target of glymphatic system function that occurred during sleep.

In another embodiment 830, a PET scan can be used with a radiotracer specific for a particular protein of interest and relative standard uptake value (SUVr) that quantifies the proteinopathy build up in the brain. In another embodiment, the radiotracer binds to a soluble form of the proteinopathy protein and the PET scan SUVr quantifies the change in concentration of the soluble protein following sleep.

In another embodiment, MRI 850 can be used to measure changes in brain volume, or degree of neurodegeneration, in anatomical regions of interest such as the hippocampus, entorhinal cortex, thalamus, orbitofrontal, parietal, temporal, anterior, and posterior cingulate and the precuneus regions over two time points separated by several months to provide an target rate of neurodegeneration for an individual.

In another embodiment 870, spinal fluid concentration of a proteinopathy protein is assayed either in the morning or both before and after sleep. The absolute concentration levels normed to a population or the diurnal difference in concentration before and after sleep provide a target molecular marker for that protein that measures glymphatic flow as net clearance of the protein and also serves as a marker of brain proteinopathy and neurodegeneration.

In another embodiment 890, plasma concentration of a proteinopathy protein is assayed either in the morning or both before and after sleep. The absolute concentration levels normed to a population or the diurnal difference in concentration before and after sleep provide a target molecular marker for that protein that measures glymphatic clearance function as net glymphatic clearance of the protein and also serves as a marker of brain proteinopathy and neurodegeneration.

The target marker data acquisition module 800 can be implemented using one of embodiment 810, 830, 850, 870, or 890. Alternatively, the target marker data acquisition module 800 can be implemented using a plurality of the embodiments illustrated in FIG. 8 in combination.

Referring to FIG. 8B, 812 and 814 shows a PET scan and SUVr marker for amyloid protein in two distinct individuals. Illustrated in 816 is the SUVr scale with values near 0 signifying low tracer concentrations that occurs when there is low or no amyloid proteinopathy for the tracer to bind to. Values above 1.5 indicate high tracer concentrations that occur with high amyloid build up. The PET scan illustrated in 812 shows no buildup of amyloid in any of the brain region of interest seen in this coronal slice. In contrast, the scan illustrated in 814 shows significant buildup of amyloid in many regions (indicated by arrows) of interest including orbitofrontal and temporal. Important markers of a PET scan include the SUVr value by region of interest for the protein of interest that can be used in connection with the target prediction model. For example, the markers in the PET scans illustrated in FIG. 8B can be used as targets in training the target prediction model. Once the target prediction model is trained, new EEG features and neurovascular features can be input into the target prediction model to predict new target markers of neurodegeneration. The target marker data acquisition module 800 can be implemented using one of embodiment 810, 830, 850, 870, or 890. Alternatively, the target marker data acquisition module 800 can be implemented using a plurality of the embodiments illustrated in FIG. 8 in combination.

Figure 9:
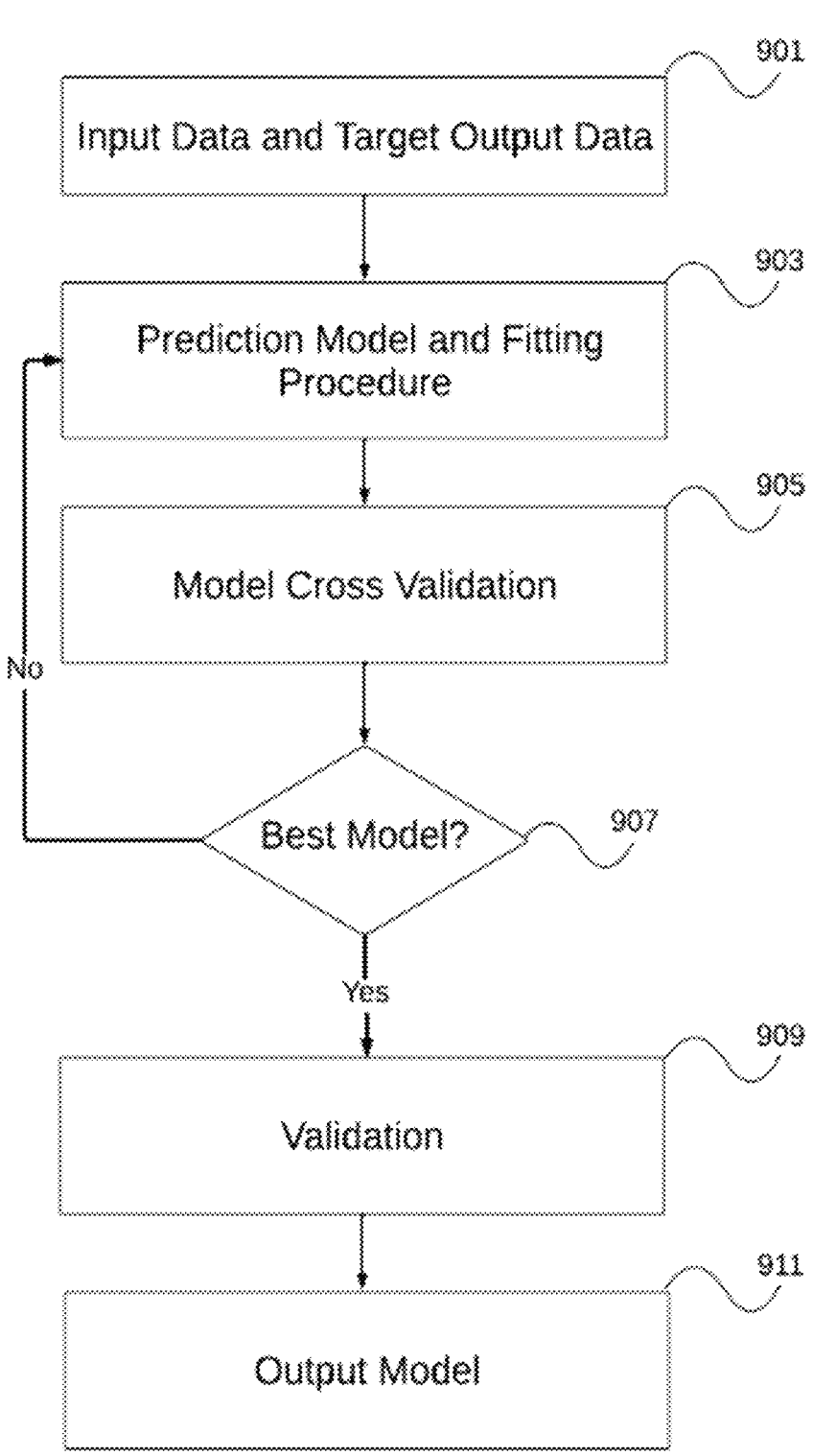
FIG. 9 is the learning module of the function mapping from non-invasive neurophysiology and neurovascular input data to target output measurements of glymphatic flow in accordance with one embodiment of the present invention, or is the learning module of the function mapping from input data for a marker of glymphatic flow to target output brain proteinopathy or neurodegeneration measurements from molecular analyses or neuroimaging, in accordance with another embodiment of the present invention.

FIG. 9 illustrates an embodiment of the biomarker learning module 900 of the system configured in accordance with the present invention and is not intended to limit scope as one of ordinary skill would understand on review of this application that other configurations could be utilized without departing from the scope of the claimed invention. Referring to FIG. 9, in one embodiment, 901 input data can be the neurophysiology feature data acquired by module 600, neurovascular feature data acquired by module 700, or a combination thereof, and glymphatic flow target data acquired by 810 of module 800. In another embodiment, 901 input data can be a marker of glymphatic flow acquired by 810 and molecular or neuroimaging target output data acquired by module 800 can be any one of the embodiments described by 830, 850, 870 or 890 in FIG. 8A or a combination thereof. The target marker data can be continuously valued, for example a pseudo-diffusion coefficient to measure glymphatic flow in mm²/sec using diffusion tensor MRI, SUVr in a PET scan or picomolar concentrations in spinal fluid molecular assays of protein, or can be categorical valued such as high or low based on thresholding the continuous valued measures using standardized levels for a disease stage. Target neuroimaging marker data can be whole brain values or values for specific regions of interest known to be primarily affected by the specific neurodegenerative disease process. The input training data 901 needs to be carefully collected on a population of 12 or more patients at varying levels of the disease process ranging from unaffected to very affected. Having data representative of patients at different extremes of the disease process gives a range of target marker data values, for example as was shown in in the amyloid PET scan SUVr values in FIG. 8B for an unaffected patient 812 and a patient with advanced amyloidosis in the brain 814. These extreme values enable the prediction model and fitting procedure 903 to learn the combination of feature patterns in the neurophysiology data 600 and neurovascular data 700 that correspond to unaffected patients and those that correspond to affected patients. Each patient data needs to be collected concurrently with neurophysiology data and neurovascular data collected together for one or more nights around the time of the target glymphatic flow, molecular or neuroimaging marker data. The device illustrated in FIG. 1 is designed to capture concurrent, time synchronized neurophysiology data and neurovascular data from a patient, and to ensure repeatability of the data acquisition by ensuring consistency of the positioning of all the sensors using the anatomically form-fitted ear device illustrated in FIG. 2G. Repeating acquisition of the neurophysiology data and neurovascular data over several nights yields additional features for training the prediction model in 903 that improves the bias-variance tradeoff of model fitting and improves predictions. The neurophysiology data and neurovascular data is preprocessed by performing feature extraction as is illustrated in FIGS. 6A-F and FIGS. 7A-E.

In 903, a model and fitting procedure are selected. The model can be one of many known machine learning and deep learning models, including those used in commercially available software packages and services, and the fitting procedure is selected based on the model selected. Random forest, a general-purpose machine learning model, works very well to identify the patterns and ranges of the neurophysiology and neurovascular feature values that best separate, or predict, the target glymphatic flow, molecular or neuroimaging markers. Acquiring the patient training data is expensive and requires an investigational review board approved clinical study. Random forest has the advantage over deep learning models in that it provides good results on a relatively small number of patient data examples. Once the model is learned on a population of patients representative of the target application, predictions of brain glymphatic flow, proteinopathy or neurodegeneration in new, unseen patients can be made from the neurophysiology and neurovascular sleep data acquired by the device illustrated in FIG. 1A without subjecting a patient to expensive and invasive clinical procedures such as brain MRI, cerebrospinal fluid molecular analysis or PET neuroimaging. This allows the device illustrated in FIG. 1A to both screen for markers of indicating out-of-range values of glymphatic flow, brain proteinopathy or neurodegeneration and to monitor progression of those markers over time for individuals that screen positive.

Once a model such as random forest is selected, the neurophysiology and neurovascular data are input features and the target marker data is the target output in the model cross validation 905. The patient data of 901 is first randomly split into a number of folds, such as five non-overlapping sets. The model in 903 is fit to the data of the first four folds and the fitted model is used to predict the target marker data of the patients in the $5^{th}$ fold. This procedure is repeated four more times, each time leaving out a new fold of patients and their data, resulting in model predictions of the complete target marker data from the input neurophysiology and neurovascular feature data. In 907 the model is evaluated using a goodness-of-fit metric that can be the root-mean-square between the prediction in 903 and the target marker data. Operations 901-907 can be repeated using several different models to determine which provides the most accurate prediction of the target marker data. The best target prediction model is promoted to 909 where holdout patients and their data, including target marker data that has never been seen by the model, is tested and the prediction model and its performance on the holdout data is outputted in 911.

Figure 10:
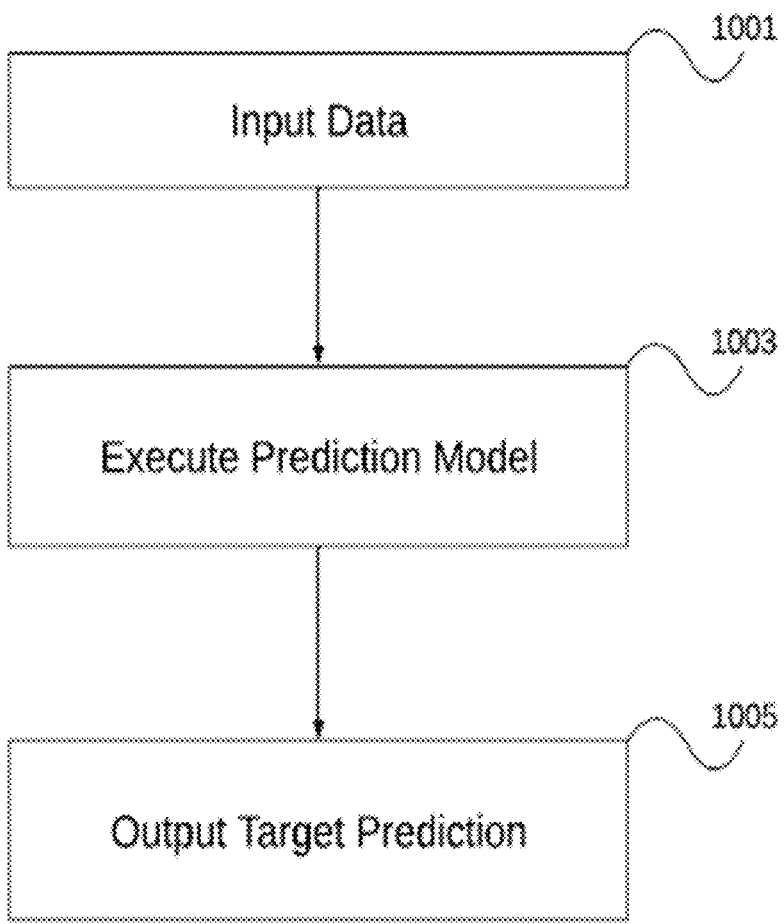
FIG. 10 is the prediction module of a target marker of glymphatic flow from non-invasive neurophysiology and neurovascular input data in accordance with one embodi-ment of the present invention, or is the prediction module of a target molecular analysis or neuroimaging of brain pro-teinopathy and neurodegeneration using input data that are markers of glymphatic flow in accordance with another embodiment of the present invention.

FIG. 10 illustrates an embodiment of the target prediction module 1000 of the system configured in accordance with the present invention and is not intended to limit scope as one of ordinary skill would understand on review of this application that other configurations could be utilized without departing from the scope of the claimed invention. Referring to FIG. 10, in one embodiment, 1001 is new neurophysiology and neurovascular data acquired by modules 600 and 700 from an individual and are inputted into the target prediction model output of 911. Features are extracted from the data as illustrated in FIG. 6A-F and FIG. 7A-E. The new neurophysiology and neurovascular data can be acquired from a new, unseen patient or from a patient that was part of the original training data but the new data is acquired several months or years later to evaluate progression of disease. In operation 1003, the module executes the target prediction model on the new input data of operation 1001 and outputs a marker of glymphatic flow 1005. In another embodiment, 1001 is the glymphatic flow output of the target prediction model 1005 and in operation 1003, the module executes the target prediction model on this new input data of operation 1001 and outputs a marker of brain proteinopathy or neurodegeneration 1005.

The target prediction can be a predicted value for glymphatic flow, a level of a protein accumulation such as those described previously or a degree of neurodegeneration measured as changes in whole-brain volume or regional volume using structural MRI. The predictions can be continuous values of marker values used to monitor for disease progression or response to intervention, or categorical values to determine the presence or absence of a disease stage. The target predictions of disease stage classification can be submitted for regulatory approval with the appropriate regulatory validation study and reporting of sensitivity, specificity, positive and negative predictive values compared to a gold-standard target such as a molecular analysis or neuroimaging test.

Figure 11A:
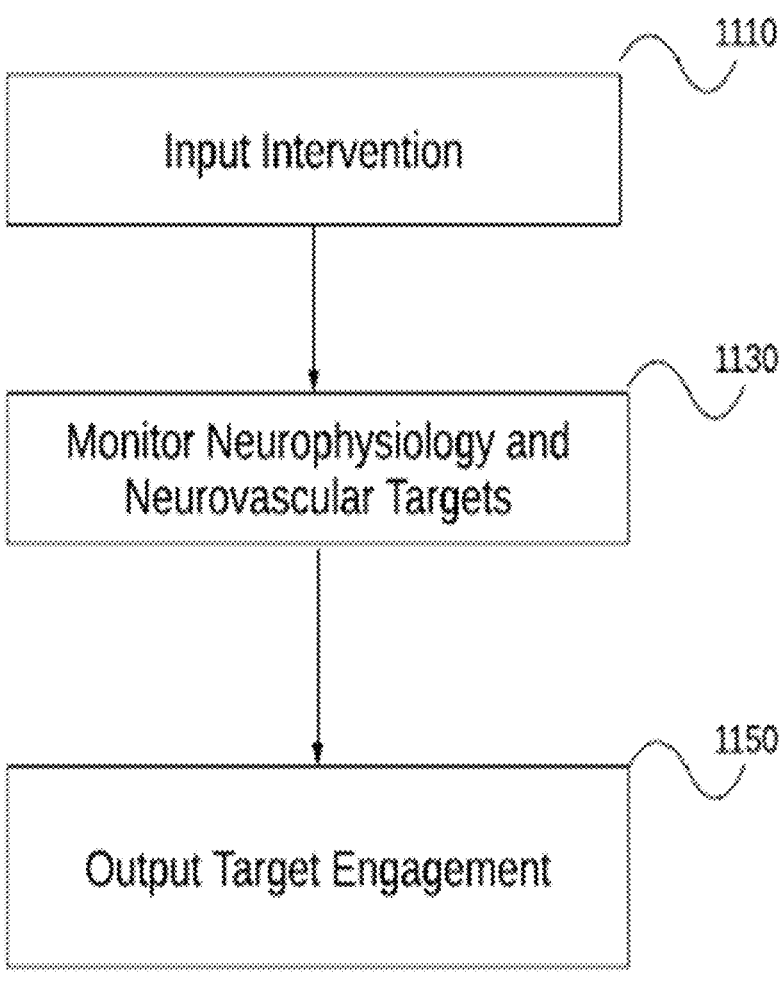
FIGS. 11A-11C illustrate the target engagement module and associated data in accordance with one embodiment of the present invention.
Figure 11B:
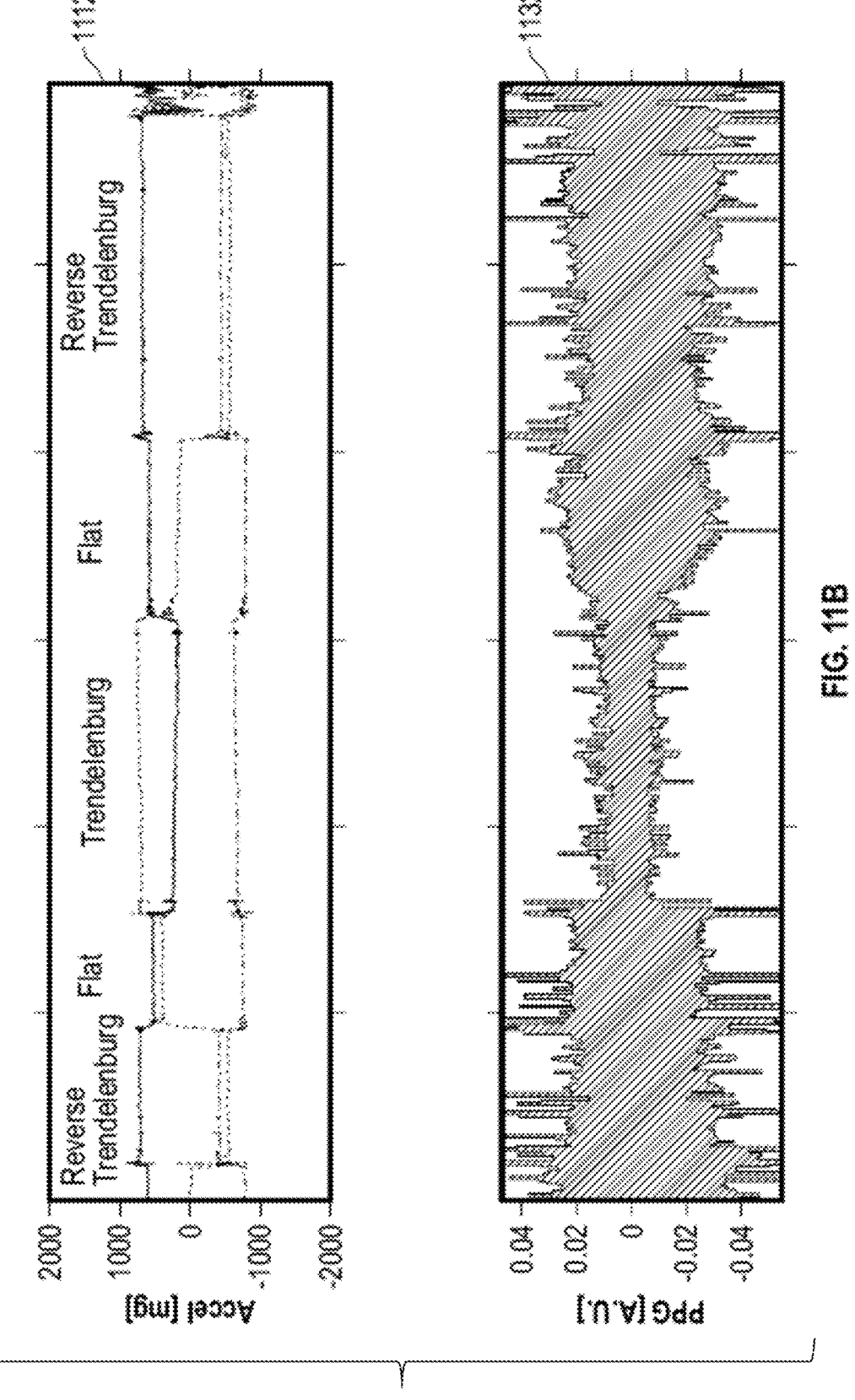
Figure 11B:
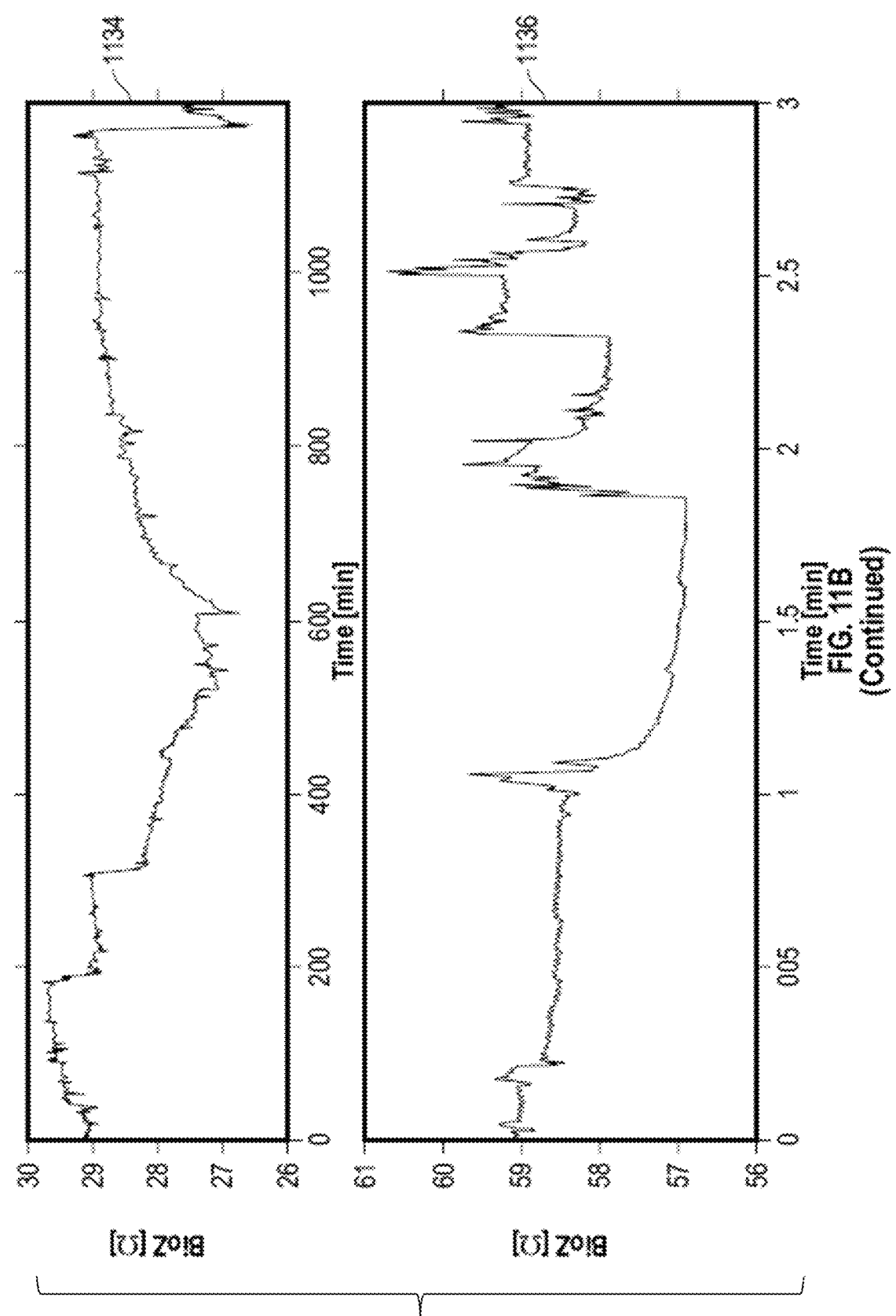
Figure 11B:
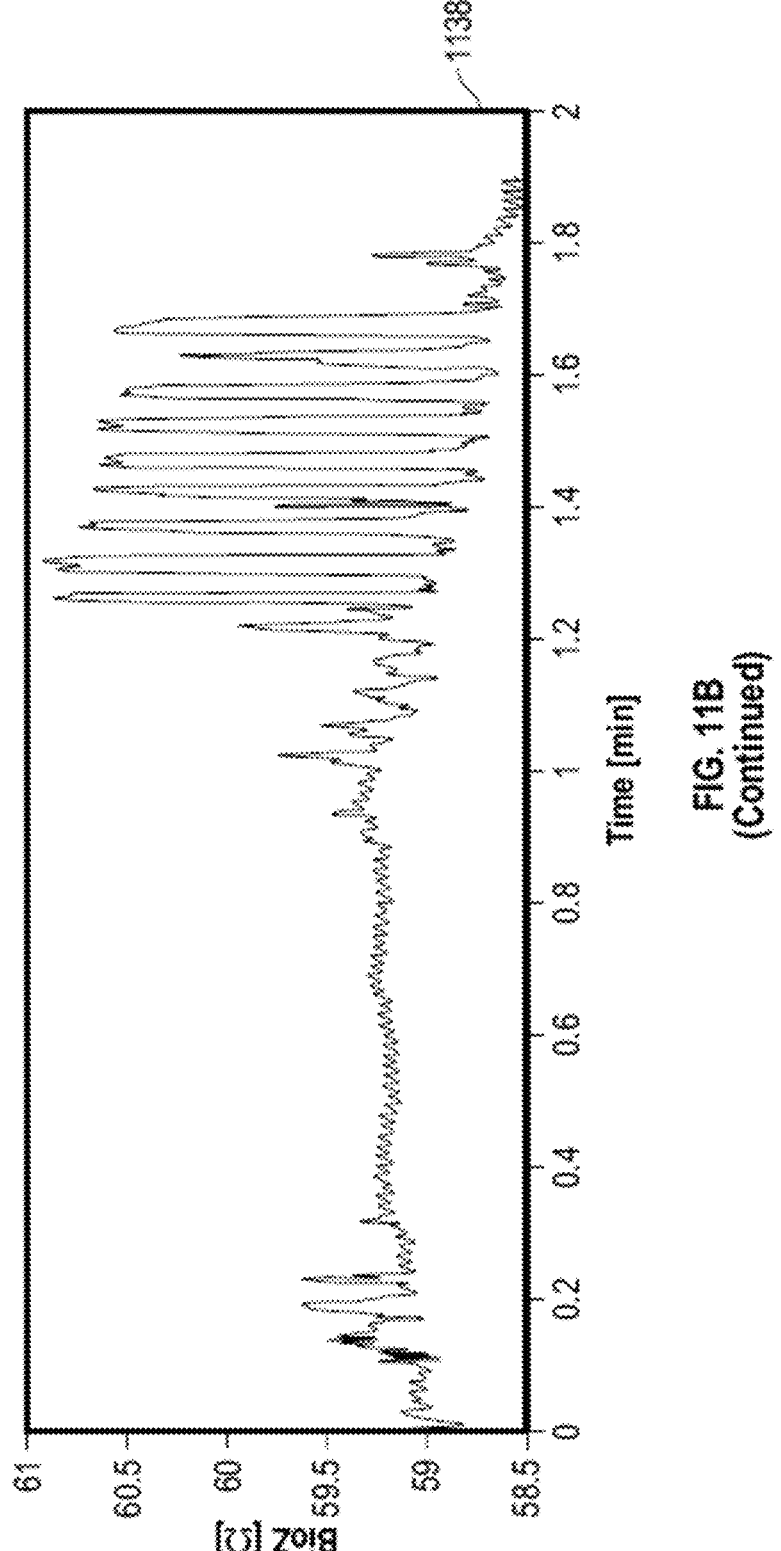
Figure 11C:
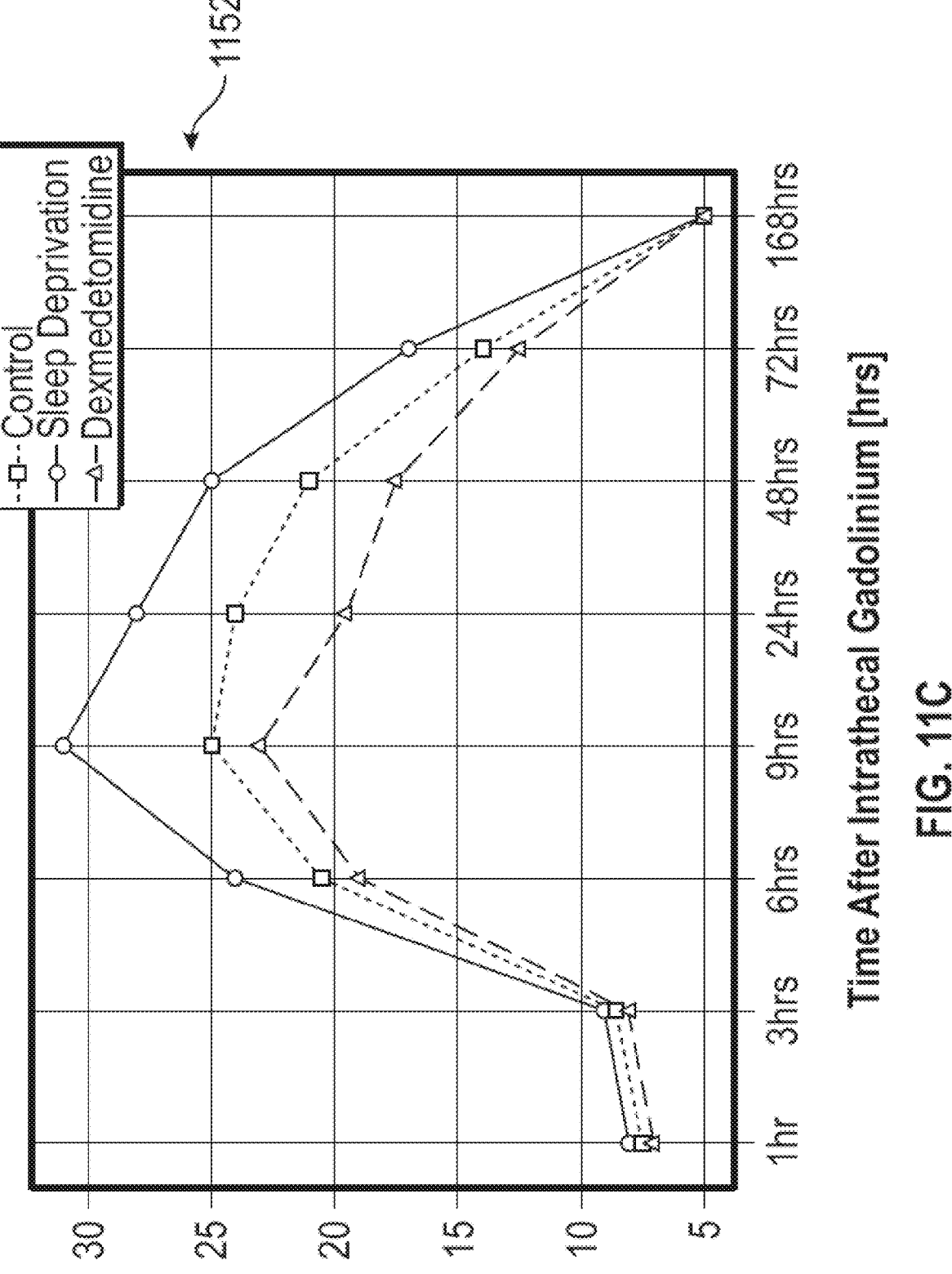

FIG. 11A-C illustrate an embodiment of the target engagement module 1100 of the system configured in accordance with the present invention and is not intended to limit scope as one of ordinary skill would understand on review of this application that other configurations could be utilized without departing from the scope of the claimed invention. Referring to FIG. 11A, in one embodiment, the target engagement module 1110 records data from an intervention before sleep or during sleep, module 1130 records the neurophysiology and neurovascular data during sleep and input data from the intervention in operation 1110. In module 1150, engagement of the intervention with one of a neurophysiology target or feature, illustrated in FIG. 6A, or one of a neurovascular target or feature, illustrated in FIG. 7A, or a combination of either, is computed as the change in the neurophysiology or neurovascular feature value from baseline. The process 1110, 1130 and 1150 can be repeated multiple times at different levels or dosing intensities of the therapeutic intervention to establish a target engagement response curve.

The prediction model 911 can be executed using data inputs 1110 and 1130 to output a prediction of the therapeutic intervention's expected impact on glymphatic flow, brain proteinopathy or neurodegeneration in the short term or if sustained in the long term. The glymphatic flow, brain proteinopathy or neurodegeneration prediction that is output can be used to show the effect of the intervention on the glymphatic flow, molecular or neuroimaging marker of neurodegeneration. In other embodiments, operation 1110 can record cardiovascular, diet, pharmaceutical or neuromodulation interventions, which data is then input into 1130 for execution computation of target engagement at operation

1150. As such, the effect of the interventions on the neurophysiology and neurovascular data can be ascertained and using the prediction model 911 the intervention's effect on a marker of neurodegeneration determined.

Referring to FIG. 11B, in one embodiment an input intervention can be raising (reverse Trendelenburg) or lowering (Trendelenburg) the head relative to the feet relative to a flat supine position as illustrated in 1112. Trendelenburg increases intracranial perfusion pressure. Monitoring the transcranial impedance in 1134 during the interventions of 1112 shows that the transcranial impedance decreased with Trendelenburg and returned to normal as the patient was returned to a flat supine position, demonstrating target engagement of this intervention with cerebral fluid volume. Monitoring the amplitude envelope of in-ear PPG tracing in 1132 shows the reverse occurring with Trendelenburg decreasing the amplitude, or blood volume, going to the ear and scalp and returning to normal when the patient is returned to a flat supine position.

In another embodiment, an input intervention can be a cardiopulmonary intervention such as a Valsalva maneuver or hyperventilation. The transcranial impedance tracing following these two cardiopulmonary interventions are illustrated in 1136 and 1138. In 1136 the patient performed a 45 second Valsalva maneuver starting at the 1-minute mark. The Valsalva maneuver increases intrathoracic pressure thereby decreasing venous return from the head. The decrease in venous return results in venous engorgement and increase in cerebral fluid volume. This is demonstrated by the decrease in the transcranial impedance during the Valsalva in tracing 1136. In 1138, the same patient started hyperventilating lightly at 1 minute and progressed to full hyperventilation at 1 minute and 15 seconds. Each inspiration decreases intrathoracic pressure and increases venous return, causing a decrease in cerebral fluid volume and an increase in transcranial impedance, as shown in tracing 1138. In both these interventions, monitoring a neurovascular tracing demonstrated target engagement of the intervention with the neurovascular measure, in this case cerebral fluid volume.

Referring to FIG. 11C, in another embodiment when target engagement of an intervention with one or more of the neurophysiology and neurovascular data has been determined, the prediction model 911 is used to determine the intervention's effect on a marker of glymphatic flow, brain proteinopathy or neurodegeneration. Illustration 1152 shows rates of clearance of intrathecal gadolinium from the brain measured by serial MRI under three different interventions. The first intervention is control, that is normal sleep with no intervention, the second intervention is sleep deprivation and the third intervention is dexmedetomidine that increases the duration of slow wave sleep. These three interventions engage sleep EEG measures, particularly slow wave sleep duration. Illustration 1152 shows corresponding slower clearance of the contrast agent with sleep deprivation (no slow wave sleep) compared to control, and control shows slower clearance than dexmedetomidine (increased slow wave sleep), as expected from prediction model 911 that is trained on sleep EEG data, neurovascular data and target brain proteinopathy and neurodegeneration data.

Embodiments Set Forth as Clauses

In addition to the forgoing, the various embodiments of the present disclosure include, but are not limited to, the embodiments set forth in the following clauses.

Clause 1. A method implemented with one or more computer processors, the method comprising:

a. accessing, by the one or more computer processors, neurophysiological data and neurovascular data recorded during sleep;

b. executing, by the one or more computer processors, a function mapping from said neurophysiological data and neurovascular data to a target that is a marker of glymphatic flow; and c. outputting, by the one or more computer processors, a target prediction model based on the function mapping.

Clause 2. The method of clause 1, further comprising:

a. executing, by the one or more computer processors, a second function mapping from the marker of glymphatic flow to a target that is one of a molecular analysis marker of neurodegeneration or a neuroimaging marker of neurodegeneration; and b. outputting, by the one or more computer processors, a target prediction model based on the second function mapping.

Clause 3. The method of clause 1, wherein the neurophysiological data are electroencephalogram recordings, and sleep macrostructure and sleep microstructure features are extracted from the electroencephalogram recordings.

Clause 4. The method of clause 1, wherein the neurovascular data comprise one or more of electrical impedance recordings taken from a patient's head, photoplethysmography measured at the patient's head, and inertial measurement unit acceleration measured in a patient's ear, wherein the neurovascular data are used to compute sleep cerebral fluid volume changes, cerebral perfusion pulsation, heart rate variability, resting heart rate, pulse transit time, pulse wave velocity and respiratory rate.

Clause 5. The method of clause 1, wherein the neurophysiological data and neurovascular data are acquired from a wearable device.

Clause 6. The method of clause 5, wherein sensors of the wearable device are inserted into an ear of a patient and measurements are taken from the ear or ear canal.

Clause 7. The method of clause 6, wherein the wearable device has a bladder that is pressurized inside the ear canal to increase the interfacial surface contact of the sensors to the canal a wall of the ear canal.

Clause 8. The method of clause 2, wherein the molecular analysis marker of neurodegeneration is a CSF or blood plasma assay of one of β-amyloid, tau, p-tau, α-synuclein, and neurofilament light.

Clause 9. The method of clause 2, wherein the neuroimaging marker of neurodegeneration is a PET scan with a radiotracer that binds to one of β-amyloid, tau, or glucose.

Clause 10. The method of clause 2, wherein the neuroimaging marker of neurodegeneration is an MRI scan.

Clause 11. The method of clause 1, further comprising: inputting new neurophysiological data and new neurovascular data into the target prediction model; and outputting a predicted marker of glymphatic flow.

Clause 12. The method of clause 1, further comprising: inputting intervention data into the target prediction model;

inputting new neurophysiological data and new neurovascular data into the target prediction model;

outputting a predicted target marker of glymphatic flow; and determining an effect of the intervention data on the predicted target marker of glymphatic flow.

Clause 13. A system comprising:

one or more computer processors;

a neurophysiological data acquisition module configured to measure neurophysiological data;

a neurovascular data acquisition module configured to measure neurovascular data; and a transmission module configured to transmit the electroencephalogram data and the neurovascular data to a second computing device.

Clause 14. The system of clause 13, wherein the one or more computer processors, the neurophysiological data acquisition module, the neurovascular data acquisition module, and the transmission module are disposed in a wearable device.

Clause 15. The system of clause 14, wherein the wearable device is configured to attach to an ear of a patient.

Clause 16. The system of clause 15, wherein sensors of the wearable device are inserted into the ear and measurements are taken from the ear or ear canal.

Clause 17. The system of clause 16, wherein the wearable device comprises a bladder that is pressurized inside the ear canal to increase interfacial surface contact of the sensors to a wall of the ear canal.

Clause 18. The system of clause 13, wherein the neurophysiological data are electroencephalogram recordings, and sleep macrostructure and sleep microstructure features are extracted from the electroencephalogram recordings.

Clause 19. The system of clause 13, wherein the neurovascular data comprise one or more of electrical impedance recordings taken from a patient's head, photoplethysmography measured at the patient's head, and inertial measurement unit acceleration measured in a patient's ear, wherein the neurovascular data are used to compute sleep cerebral fluid volume changes, cerebral perfusion pulsation, heart rate variability, resting heart rate, pulse transit time, pulse wave velocity and respiratory rate.

Clause 20. The system of clause 13, wherein the second computing device is one of a mobile telephone, a local computing device, and a remote computing device.

Clause 21. The system of clause 13, wherein the second computing device comprises a machine learning algorithm configured to input the neurophysiological data and the neurovascular data and configured to output a target prediction model.

Clause 22. The system of clause 21, wherein the target prediction model is configured to receive as input new neurophysiological data and new neurovascular data and configured to output a predicted marker of neurodegeneration.

Clause 23. The system of clause 21, wherein the target prediction model is configured to receive as input intervention data, new neurophysiological data, and new neurovascular data, and configured to output a predicted marker of brain proteinopathy or neurodegeneration, and a determination of an effect of the intervention data on the predicted marker of brain proteinopathy or neurodegeneration.

Clause 24. A method implemented with one or more computer processors, the method comprising:

a. accessing, by the one or more computer processors, neurophysiological data and neurovascular data recorded during sleep;

b. executing, by the one or more computer processors, a function mapping from said neurophysiological data and neurovascular data to a target, the target being one or more of a marker of glymphatic flow, a molecular analysis marker of neurodegeneration, or a neuroimaging marker of neurodegeneration;

c. outputting, by the one or more computer processors, a target prediction model based on the function mapping;

d. receiving, as an input, newly collected neurophysiological data and neurovascular data collected during sleep into the target prediction model;

e. receiving, as an input, data associated with a therapeutic intervention; and f. measuring an effect of the therapeutic intervention.

Clause 25. A method implemented with one or more computer processors, the method comprising:

a. activating a neurophysiological data sensor and a neurovascular data sensor of a wearable device;

b. gathering, by the sensors, neurophysiological data and a neurovascular data during sleep;

c. storing the neurophysiological data and the neurovascular data in a storage device of the wearable device;

d. process the neurophysiological data and the neurovascular data using a processor of the wearable device; and e. transmitting, by a transmission module of the wearable device, the neurophysiological data and the neurovascular data to a second computing device.

Clause 26. A non-transitory computer-readable medium comprising computer-executable instructions performing the operations recited in clause 1.

Clause 27. A non-transitory computer-readable medium comprising computer-executable instructions performing the operations recited in clause 24.

Clause 28. A non-transitory computer-readable medium comprising computer-executable instructions performing the operations recited in clause 25.

Additional Examples of Wearable Devices for Measuring Transcranial Impedance

The following description provides additional examples of head-mounted wearable devices that can be used to measure glymphatic flow for the purpose of assessing neurodegeneration. Similar to the examples described previously, the following examples of head-mounted wearable devices use electrodes to measure transcranial impedance. The electrodes can include an input electrode that introduces a small input current at the scalp of the subject wearing the device while sleeping. The wearable device includes additional electrodes that can measure electrical potential at various locations on the head in response to the input current introduced by the input electrode. The electrical potential measurements are used to identify surfaces of equipotential. The measurements of equipotential are collected over time while the subject sleeps and the time-dependent changes in equipotential provide a measure of glymphatic flow. The frequency of the input current introduced by the input electrode can also be varied to obtain a more complete set of impedance data.

Figure 12A:
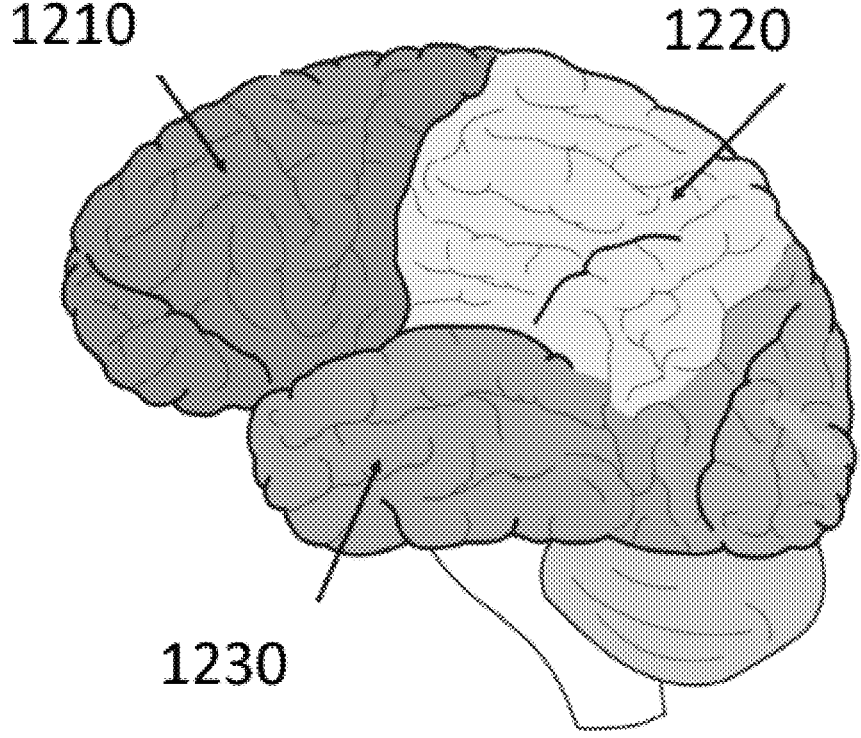
FIGS. 12A, 12B, and 12C illustrate an embodiment of the system for non-invasive measurement of glymphatic flow and neurodegeneration in an over-the-head formfactor that positions the data acquisition sensors used to acquire tran-scranial impedances over the left and right temporal and parietal brain lobes, configured in accordance with the present disclosure.
Figure 12B:
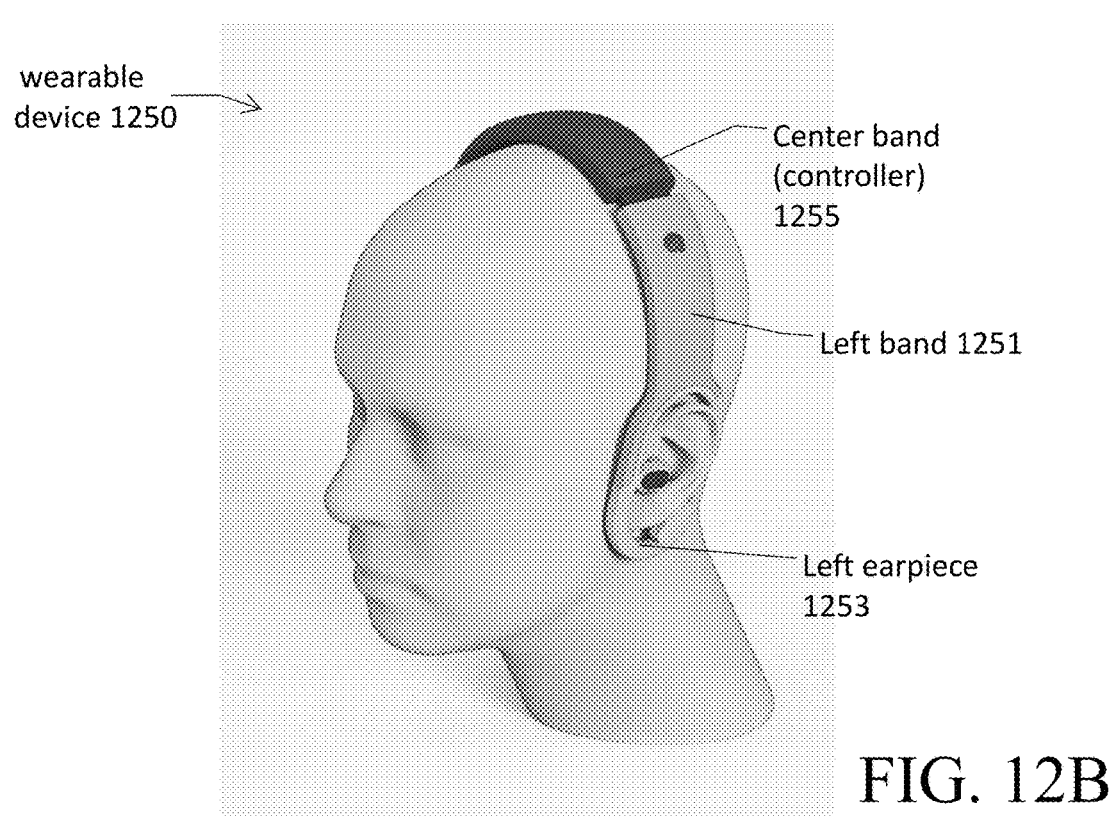
Figure 12C:
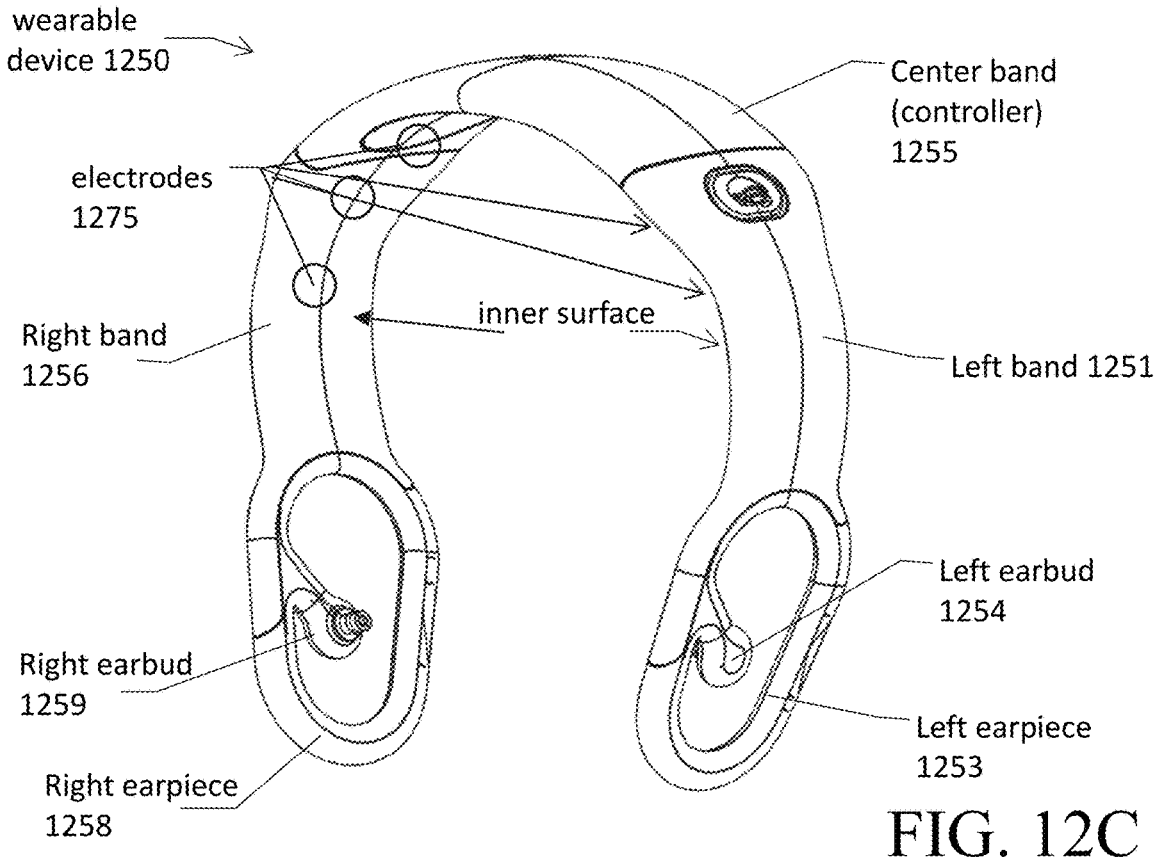

The details of the invention and various embodiments can be better understood by referring to the figures. FIGS. 12A, 12B and 12C illustrate an embodiment of the functional description of the system configured in accordance with the present invention and is not intended to limit scope as one of ordinary skill would understand on review of this application that other configurations could be utilized without departing from the scope of the disclosure. Referring to FIG. 12A, transcranial electrodes for acquiring continuous electrical impedance spectroscopy data can be positioned over different anatomical brain lobes, such as the left frontal lobe 1210 and corresponding right frontal lobe (not visible in FIG. 12A), the left parietal lobe 1220 and corresponding right parietal lobe (not visible in FIG. 12A), and the left temporal lobe 1230 and corresponding right temporal lobe (not visible in FIG. 12A). The system can comprise a wearable device that can be attached to a subject's head and that is designed to position the transcranial electrodes over different transcranial brain lobes. In one example illustrated in FIGS. 12B and 12C, the wearable device 1250 can go over the user's head, similar to headphones, and comprises a left band 1251 and a right band 1256 that are joined at their respective proximal ends by a center band 1255. The distal end of the left band 1251 comprises a left earpiece 1253 that can wrap around at least a portion of the subject's left ear and the distal end of the right band 1256 comprises a right earpiece 1259 that can wrap around at least a portion of the subject's right ear. Although not required, the left earpiece 1253 can include an optional left earbud 1254 that fits within the subject's left ear canal and the right earpiece 1258 can include an optional right earbud 1259 that fits within the subject's right ear canal. When included, the earbuds can be used for proper positioning of the wearable device and can include optional sensors. The center band 1255 can contain a controller for controlling operation of the wearable device. The controller can include a power source (e.g., a battery) for supplying the current to the input electrode. The controller also can include a processor and memory for controlling the power source and processing the electrical potential data measured by the electrodes. The controller can further include a transmission module for wired or wireless communication of data with a nearby computing device such as a mobile phone, tablet, or PC. The inner surfaces of the left band 1251 and the right band 1256 that contact the subject's scalp can include a plurality of impedance spectroscopy electrodes 1275. In some embodiments, the impedance spectroscopy electrodes can also be located along the inner surface of the center band 1255. The power source can supply an input current to one of the electrodes 1275, while other electrodes measure the electrical potential in response to the input current. While gathering impedance measurements during sleep, the controller can vary the electrode providing the input current among the multiple electrodes of the wearable device 1250 in order to gather a broader set of electrical potential measurements. The shape of the wearable device 1250 allows for gathering electrical impedance spectroscopy data across the left and right sides of the head and across the temporal or parietal lobes for non-invasive measurement.

Figure 12D:
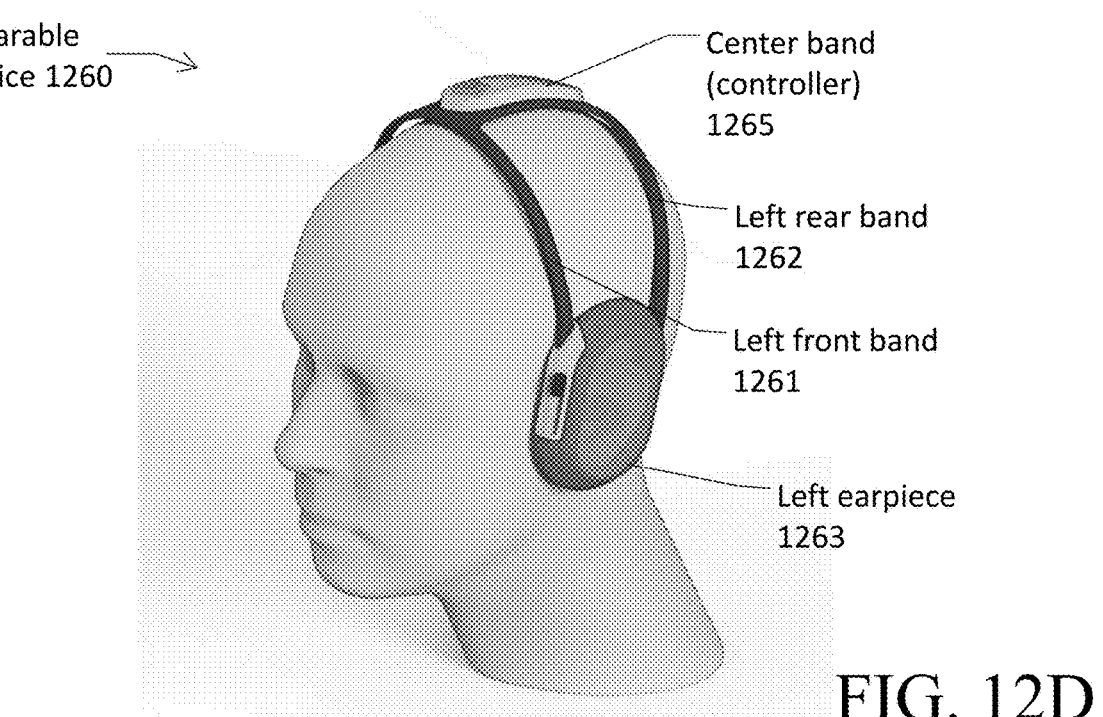
FIGS. 12D and 12E illustrate another embodiment of the system for non-invasive measurement of glymphatic flow and neurodegeneration in an over-the-head form factor that positions the data acquisition sensors used to acquire tran-scranial impedances in front and rear bands over the left and right temporal, parietal, and frontal brain lobes, configured in accordance with the present disclosure.
Figure 12E:
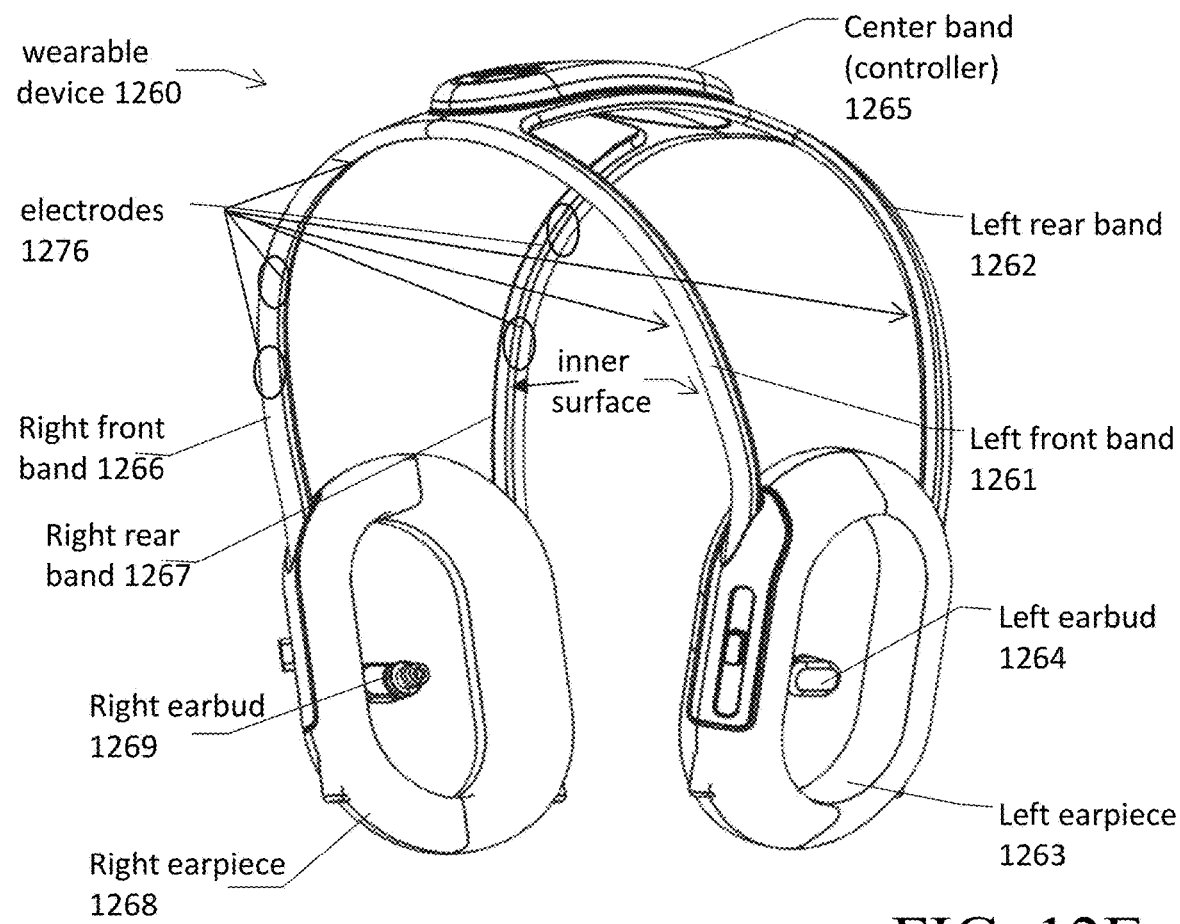

In a second example illustrated in FIGS. 12D and 12E, the wearable device 1260 comprises components similar to the previously described wearable device 1250. Briefly, wearable device 1260 comprises a left front band 1261, a left rear band 1262, a right front band 1266 and a right rear band 1267 that are joined at their proximal ends by a center band 1265. The distal end of the left front band 1261 and left rear band 1262 comprises a left earpiece 1263 that can wrap around at least a portion of the subject's left ear and the distal end of the right front band 1266 and right rear band 1267 comprises a right earpiece 1269 that can wrap around at least a portion of the subject's right ear. Although not required, the left earpiece 1263 can include an optional left earbud 1264 that fits within the subject's left ear canal and the right earpiece 1268 can include an optional right earbud 1269 that fits within the subject's right ear canal. When included, the earbuds can be used for proper positioning of the wearable device and can include optional sensors. The center band 1265 can contain a controller for controlling operation of the wearable device. The controller can include a power source (e.g., a battery) for supplying the current to the input electrode. The controller also can include a processor and memory for controlling the power source and processing the electrical potential data measured by the electrodes. The controller can further include a transmission module for wired or wireless communication of data with a nearby computing device such as a mobile phone, tablet, or PC. The inner surfaces of the left front and rear bands 1261 and 1262 and the inner surfaces of the right front and rear bands 1266 and 1267 can comprise a plurality of electrodes 1276 that contact the subject's scalp and that are used to make the impedance measurements along the subject's head. The controller can select one of the electrodes as the input electrode that provides the input current and other electrodes can measure electrical potential in response to the input current.

Wearable device 1260 differs from wearable device 1250 in that it comprises multiple bands on the left side and multiple bands on the right side that go over the user's head to extend the distribution of the electrodes over the subject's head. In the example illustrated in FIGS. 12D and 12E, two bands are shown on the left side and two bands are shown on the right side. However, other embodiments can include additional bands on each side to further distribute the electrodes over the subject's head. With the impedance spectroscopy electrodes 1276 situated along the inner facing surfaces of the wearable device's left front and rear bands 1261 and 1262 and the right front and rear bands 1266 and 1267, the electrodes contact the subject's head and can acquire impedance spectroscopy data across the temporal, parietal and frontal lobes for non-invasive measurement of glymphatic flow.

Figure 13:
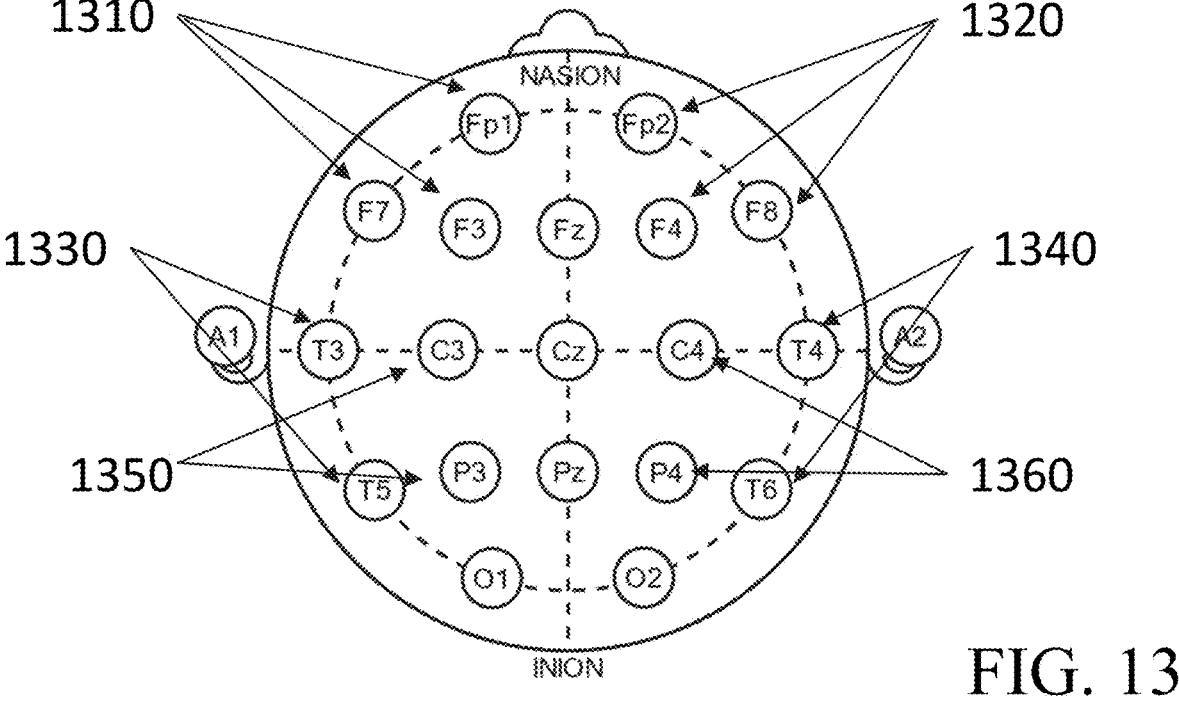
FIG. 13 illustrates an embodiment of the system for non-invasive measurement of glymphatic flow and neuro-degeneration in an over-the-head formfactor that positions the data acquisition sensors used to acquire transcranial impedances in a headcap that extends over the left and right temporal, parietal, and frontal brain lobes, configured in accordance with the present disclosure.

FIG. 13 illustrates an embodiment of the electrical impedance spectroscopy sensors of the system configured in accordance with the present invention in a headcap used for clinical electroencephalography (EEG) data acquisition. The illustration is not intended to limit scope as one of ordinary skill would understand on review of this application that other configurations could be utilized without departing from the scope of the disclosure. Referring to FIG. 13, electrodes 1310 are placed over the left frontal lobe, 1320 over the right frontal lobe, 1330 over the left temporal lobe, 1340 over the right temporal lobe, 1350 over the left parietal lobe and 1360 over the right parietal lobe. EEG signals have a unique frequency and are measured passively by the electrodes contacting the subject's head. However, the electrical impedance spectroscopy system multiplexes data acquisition through these electrodes during clinical EEG data acquisition. As explained previously, the electrical impedance measurements are an active, not a passive, technique in that the input current is provided at the input electrode and the responsive electrical potential is measured at other electrodes.

Figure 14A:
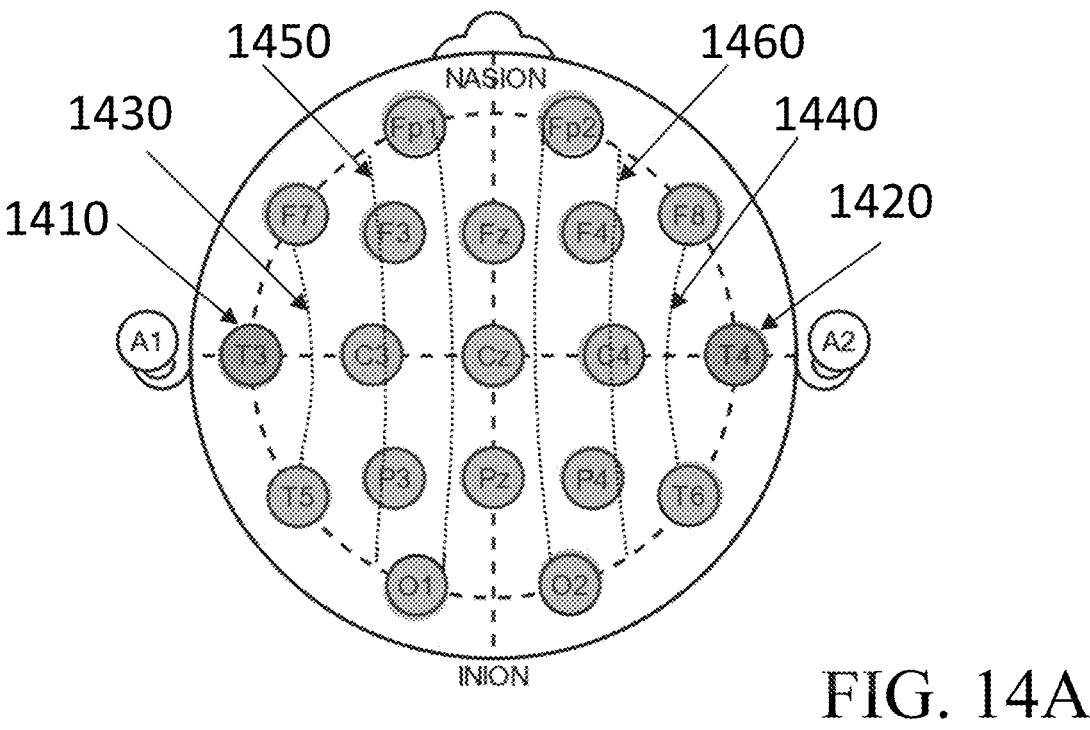
FIGS. 14A and 14B illustrate an embodiment of the system for non-invasive measurement of glymphatic flow and neurodegeneration in an over-the-head formfactor that positions the data acquisition sensors used to acquire transcranial impedances in a plurality of left and right locations around the brain, configured in accordance with the present disclosure.
Figure 14B:
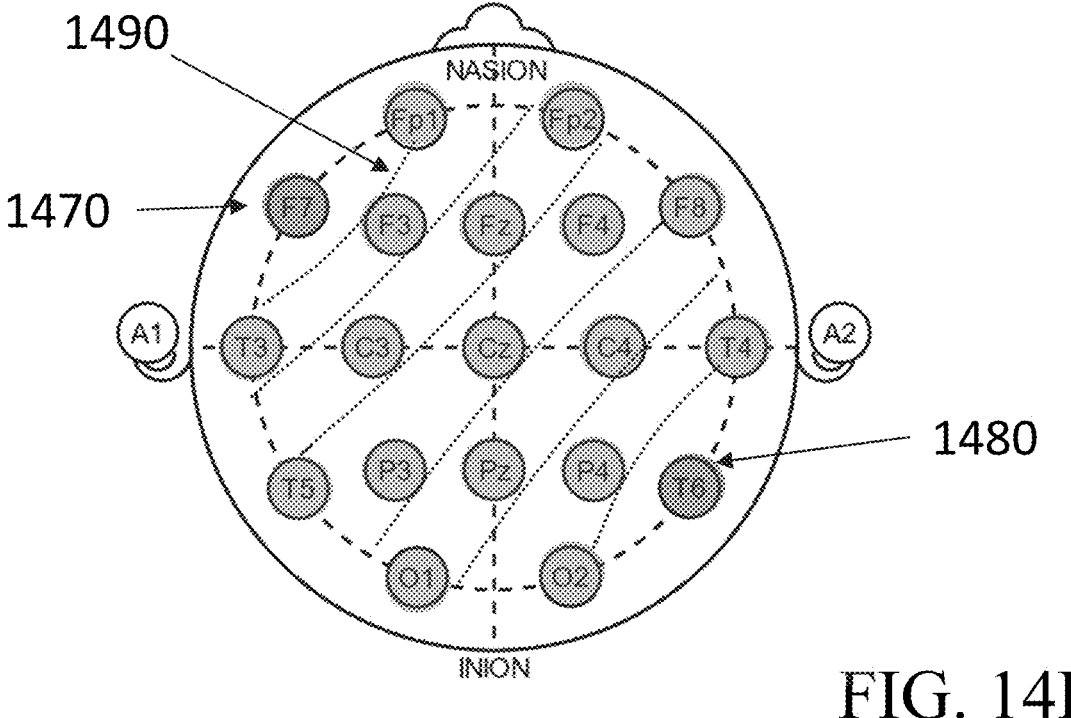

Continuing with the headcap embodiment of the wearable device illustrated in FIG. 13, FIGS. 14A and 14B illustrate an embodiment of techniques for measuring electrical impedance spectroscopy with a headcap used for clinical electroencephalography data acquisition. While not illustrated in FIGS. 13, 14A, and 14B, a controller similar to the controller previously described in FIGS. 12B-12E can be attached to the top or sides of the headcap and electrically coupled to the electrodes. Alternatively, the controller can be separated from the headcap, but electrically coupled to the headcap electrodes by one or more cables that transmit power and data signals between the controller and the electrodes. The illustrations are not intended to limit scope as one of ordinary skill would understand on review of this application that other configurations could be utilized without departing from the scope of the disclosure. Referring to FIG. 14A, the electrical impedance spectroscopy system inputs current over multiple frequencies into left temporal electrode 1410 and with sink right temporal electrode 1420. During current input, the system measures the electrical potential at the remaining electrodes shown in FIG. 14A. This process is repeated across all frequencies selected and throughout the night while the user sleeps to acquire a time-series of impedance spectroscopy data. From the potentials recorded at the sensing electrodes, a finite element model is used to solve for the equipotential surfaces illustrated by 1430 and 1450 overlying the left-brain hemisphere, and 1440 and 1460 overlying the right-brain hemisphere. Other equipotential surfaces can be derived from the electrodes and increasing the number of electrodes over the brain enables higher spatial resolution of the equipotential surfaces. The time-dependence during sleep of these equipotential surfaces is used to measure glymphatic flow and flow shunting across different anatomical areas of the brain.

As illustrated in FIG. 14B, the electrodes for current input and current sink can be rotated to new electrodes 1470 over the left frontal lobe and 1480 over the right posterior temporal lobe. Re-orienting the input and sink electrodes solves for new equipotential surfaces 1490. The input and sink electrodes can be rotated across all pairs of diametrically opposite electrodes, with each new orientation solving for new equipotential surfaces. The time-series changes recorded during a sleep episode in the equipotential surfaces from a specific pair of input-sink electrodes is a measure of brain compartment volume changes and glymphatic flow. Multiplexing electrical impedance spectroscopy with the rotation of input-sink electrodes during a sleep episode, and taking the union of the equipotential surfaces solved in each of the different orientations, gives topographic measures of brain compartment volume changes, glymphatic flow and flow shunting in the brain during sleep.

Referring now to FIGS. 15-19, further details are provided for an example embodiment of a wearable device in the form of a headcap. Similar to the previous example, the electrodes of the headcap described in connection with FIGS. 15-19 can be multiplexed to passively measure EEG signals and to actively measure electrical impedance for assessing glymphatic flow. The illustrations of FIGS. 15-19 are not intended to limit scope as one of ordinary skill would understand on review of this application that other configurations could be utilized without departing from the scope of the disclosure.

FIG. 15 provides further details of a controller 1500 for use with a headcap form of the wearable device of FIGS. 15-19. The controller 1500 also can be used with the previously described wearable devices for measuring transcranial electrical impedance. As explained previously, the controller 1500 can be attached directly to the headcap or can be a separate component that is coupled to the electrodes of the headcap by electrical wires. The controller 1500 comprises a primary module 1501 and a multiplexer module 1502. The primary module 1501 comprises a power source (battery) 1503, a microcontroller 1506, a bioimpedance circuit 1504, and a memory 1505. The battery 1503 supplies power to the components of the controller 1500, including the input current used for the impedance measurements. The microcontroller 1506 executes instructions for controlling the operation of the controller 1500 and the memory 1505 can store executable instructions and impedance data collected from the electrodes. The bioimpedance circuit 1504 is based on a 4-point or Kelvin configuration, with two electrodes/leads inputting a current (I+, I−), and two other electrodes/leads measuring the resulting potential difference (V+, V−). This measurement is performed at one or more frequencies between 100 Hz and 1 GHz. To provide tomographic capabilities, a multiplexer module 1502 expands the connectivity of the bioimpedance circuit 1504 by providing four multiplexers 1508 (8:1, though 16:1 is also possible) that are connected to each of the I+, I–, V+, V– leads to provide dynamic reconfigurability of the drive/sense configuration. These multiplexers are programmed on the fly by the microcontroller 1506. In the case of parallel-programming multiplexers, an Input/Output expander 1507 controlled by an I2C or SPI bus 1509 is used.

The addition of these multiplexers enables changing the current input points (see FIG. 16) while sensing of the scalp potential across most of the scalp surface with respect to a common reference (see FIG. 17). Together with measurement at multiple frequencies, such system provides sequential multifrequency electrical impedance tomography (MFEIT) capabilities.

Figure 16:
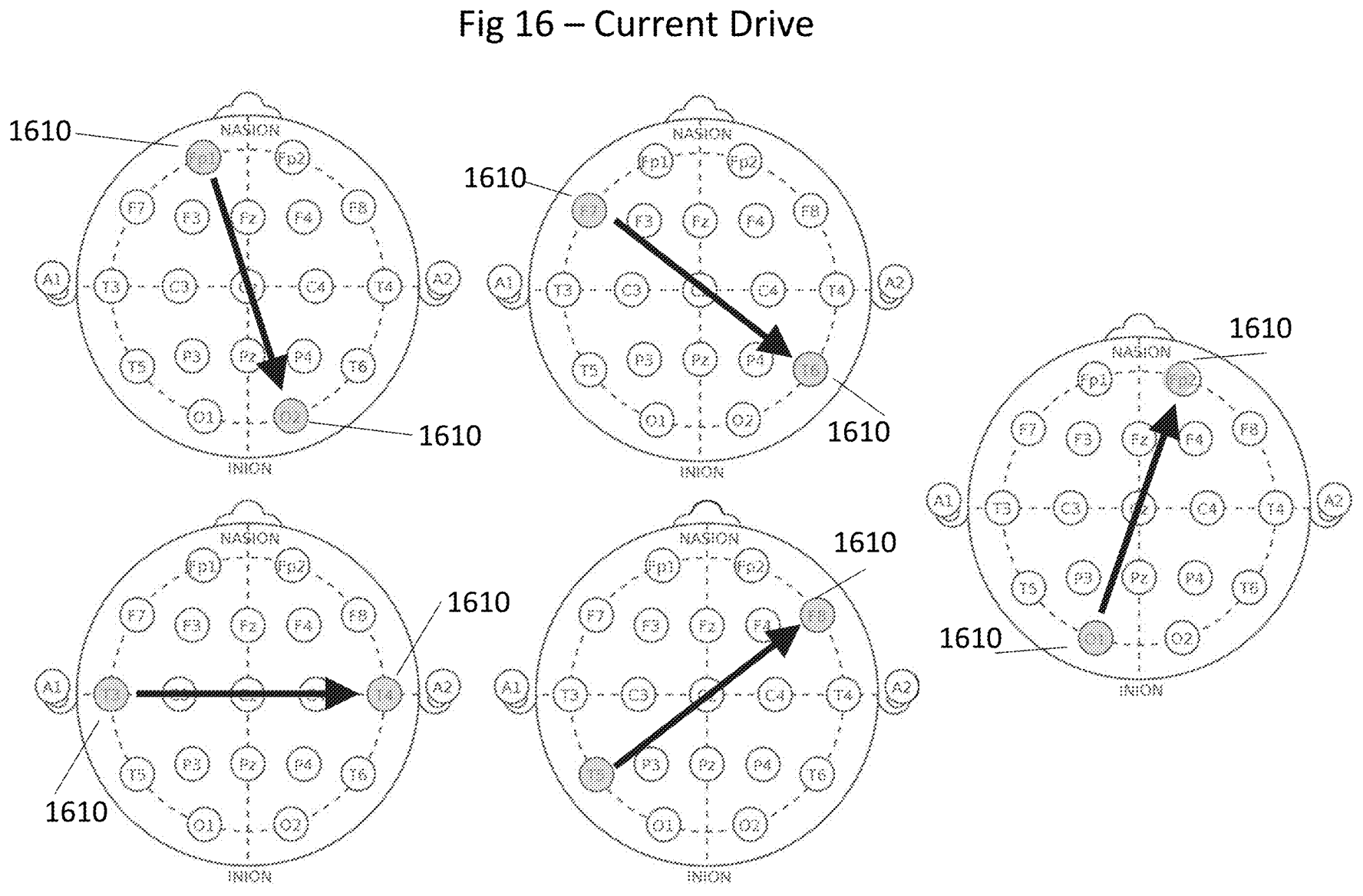

Referring to FIG. 16, an illustration is provided for collecting impedance measurements using the wearable device of FIG. 15. FIG. 16 illustrates the method of varying the input-sink electrodes. Two multiplexers redirect the input current from the current source leads (I+, I–) to two cap electrodes (1610) chosen from any of the cap electrodes to input the excitation at the subject's scalp current along different vectors, sequentially. The example of controller 1500 using 8:1 multiplexers allows five different vectors to be selected as illustrated in FIG. 16. However, in other embodiments fewer or more pairs of input-sink electrodes can be implemented.

FIG. 17 provides an illustration of the method for measuring electrical potential, from which impedance data can be derived. Two other multiplexers of controller 1500 sequentially connect one of the two sense inputs (V+, V–) of the bioimpedance circuit 1504 to any of the cap electrodes (1711) not used for current input, while the other input is chosen as common reference (1712). The common reference electrode can be a cap electrode or a forehead electrode. Note that a multichannel sensing system can also be used to sense all electrodes simultaneously without the need of multiplexing pairs of sensing electrodes. This would remove the need for the sensing multiplexers of multiplexer module 1502 coupled to the sense inputs (V+, V–).

The current implementation using 8:1 multiplexers allows 12 electrodes (other than the current input-sink electrodes), spread across the cap to be measured against the reference electrode, providing a homogeneous potential mapping across the head.

Combined with the five current input-sink configurations, this results in a total of 60 different electrical measurements for a given excitation frequency. These 60 different configurations are represented in the MUX State Machine illustrated in FIG. 19 using the logic schema illustrated in FIG. 18. Note that different mux state machines and logic schemas can be used depending on the underlying multichannel analog front end used.

Figure 20:
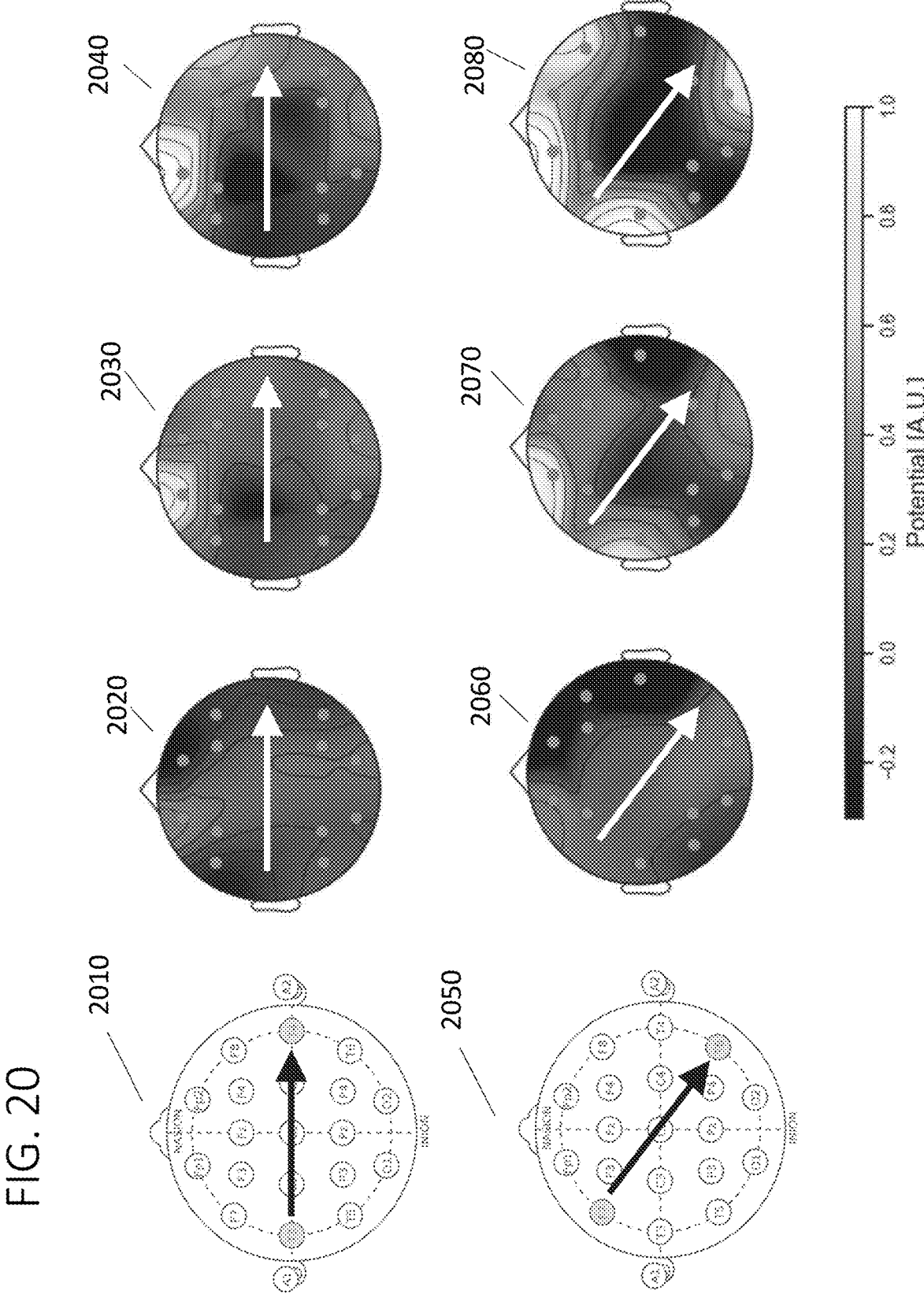
FIG. 20 illustrates example data from a headcap embodiment of a wearable device in accordance with the present disclosure in a subject sleeping with the device for 100 minutes.

Referring to FIG. 20, example data is shown from a headcap embodiment of a wearable device from a subject sleeping with the device for 100 minutes using the headcap illustrated in FIGS. 14A and 14B, in accordance with the present disclosure. Illustrated in 2010 and 2050 are two orientations of the input current through two pairs of electrodes on the headcap, marked T3 and T4 in 2010 and F7 and T6 in 2050. The input current orientation in 2010 corresponds to MUX State #s 25 through 36 in the MUX State Machine of FIG. 19. The sensing electrodes in these states are Fp1, F7, T5, O1, F3, P3, Fp2, F8, T6, O2, F4, P4 whose locations are shown in 2010. Illustrations 2020, 2030 and 2040 in FIG. 20 show the change in the measured electrical potentials in the sensing nodes from wake to sleep at 10 minutes, 45 minutes, and 90 minutes of sleep, respectively. Input current orientation 2010 reveals a progression of increasing potential in 2020, 2030 and 2040 that corresponds to an increased shift of fluid into the extracellular compartment from 10 minutes to 90 minutes of sleep that begins anteriorly in the left frontal lobe and spreads posterolateral. The input current orientation in 2050 corresponds to MUX State #s 13 through 24 in the MUX State Machine of FIG. 19. Input current orientation 2050 reveals a second progression of increasing potential in 2060 (10 minutes), 2070 (45 minutes), and 2080 (90 minutes) that corresponds to an increased shift of fluid into the extracellular compartment from 10 minutes to 90 minutes of sleep that begins over the left temporal lobe and spreads posteriorly. Shifts in fluid from the brain parenchymal intracellular compartment to the brain parenchymal extracellular compartment during sleep arise because of glymphatic flow. FIG. 20 illustrates that the present embodiment measures both the magnitude of the fluid shift, or glymphatic flow, and the topographic dynamic of the flow by brain region. Increasing the density of the electrodes in the headcap used increases the topographic resolution of the flow during sleep and is consistent with the present embodiment.

Signal Processing and Analysis of Transcranial Impedance Data

The following provides further description of signal processing and analysis of transcranial impedance data gathered using head-mounted wearable devices, such as the previously-described devices. The following description provides improved techniques for analyzing brain interstitial volume and glymphatic flow as well as assessing clearance of parenchymal waste products. Similar to the previous description, the following examples utilize head-mounted wearable devices that include electrodes for measuring transcranial impedance. Any of the previously described head-mounted wearable devices could be implemented in the following examples. The electrodes of the wearable device can include current input electrodes for introducing a small input current at the scalp of a subject and voltage sensing electrodes for measuring electrical potential at various locations on the head in response to the input current. The electrical potential can be measured over time and over varying frequencies of input current to provide a measure of intracranial fluid volume and flow.

Figure 21A:
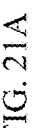
FIGS. 21A and 21B illustrate comparative resistance data collected during sleep and wake states of a subject in accordance with an example embodiment.
Figure 21B:

FIGS. 21A and B illustrates an embodiment of the method and system configured in accordance with the present invention in a headcap used on a person who was required to lay awake overnight (FIG. 21B) and on a subsequent second night monitored during normal sleep (FIG. 21A). The intervention of wake/sleep is not intended to limit scope as one of ordinary skill would understand on review of this application that other interventions affecting glymphatic flow could be utilized without departing from the scope of the disclosure. Illustrated in FIGS. 21A-B are the measured brain parenchymal resistance to glymphatic flow which is derived from transcranial impedance measurements (as described further below) that are measured repeatedly over the observation period of sleep/wake to determine the effect of the wake intervention on glymphatic flow as compared to normal sleep. Data collected during numerous intervals throughout the observation period are provided in FIGS. 21A and B. The electrical resistance during each measurement is derived from the electrical impedance over six alternating currents (corresponding to the six data points in each interval in FIGS. 21A and B) ranging from 1,600 Hz to 102,400 Hz. During normal sleep shown in FIG. 21A, at time 2110 we observe that early on in the observation period the spread between the low frequency and high frequency resistance is 3 ohms. In contrast, towards the end of the observation period at time 2120 the spread narrows to 1 ohm. The dynamic change to a lower resistance during the later intervals in the normal sleep data of FIG. 21A indicates greater glymphatic flow, and the longer the resistance remains low, the greater the glymphatic flow. Also observe the drift in the resistances at any frequency over the observation period. For example, at the beginning at time 2110 the low and high frequency resistances are 37 ohms and 34 ohms respectively. Near the end of the observation period at time 2120, they drift down to 31 ohms and 30 ohms respectively. Because of this drift, measuring at a single AC frequency is incapable of measuring changes in resistance. Furthermore, computing the resistance requires measurements at both the high and low ends of the frequency spectrum. The illustrated method and system differ from known approaches to compute a change in transcranial fluid dynamics by high-pass filtering a single frequency signal to measure the cerebral blood flow waveforms and measure changes in waveform amplitude or frequency that correlate to heartbeat.

Referring to FIG. 21B, during the onset of the wake intervention at time 2130 we observe that the spread between the low frequency and high frequency resistance is 3 ohms similar to the onset during normal sleep. In contrast to sleep data of FIG. 21A, however, towards the end of the wake observation period at time 2140 we observe that the spread has not narrowed but remains constant at 3 ohms suggesting no change in glymphatic flow or a suppression of glymphatic flow during wake compared to sleep.

The spread in resistance over frequency, for each period, can also be computed using non-linear least squares models to fit the curves and non-linear mixed effect models to generate a model fit as one of ordinary skill would understand on review of this application without departing from the scope of the disclosure. Importantly, the measured values are complex numbers but because of the Hilbert transform duality, or equivalently the linear Kramer-Kronig relation, only the real values or the imaginary values are necessary for computing the spread in the resistance. Thus, using the real values to predict the imaginary or vice versa enables a powerful out-of-sample validation of the resistances measured in each period. The linear Kramer-Kronig test can be used to dynamically reject measurements that were affected by motion, electrical interference or other artifacts.

Figure 22A:
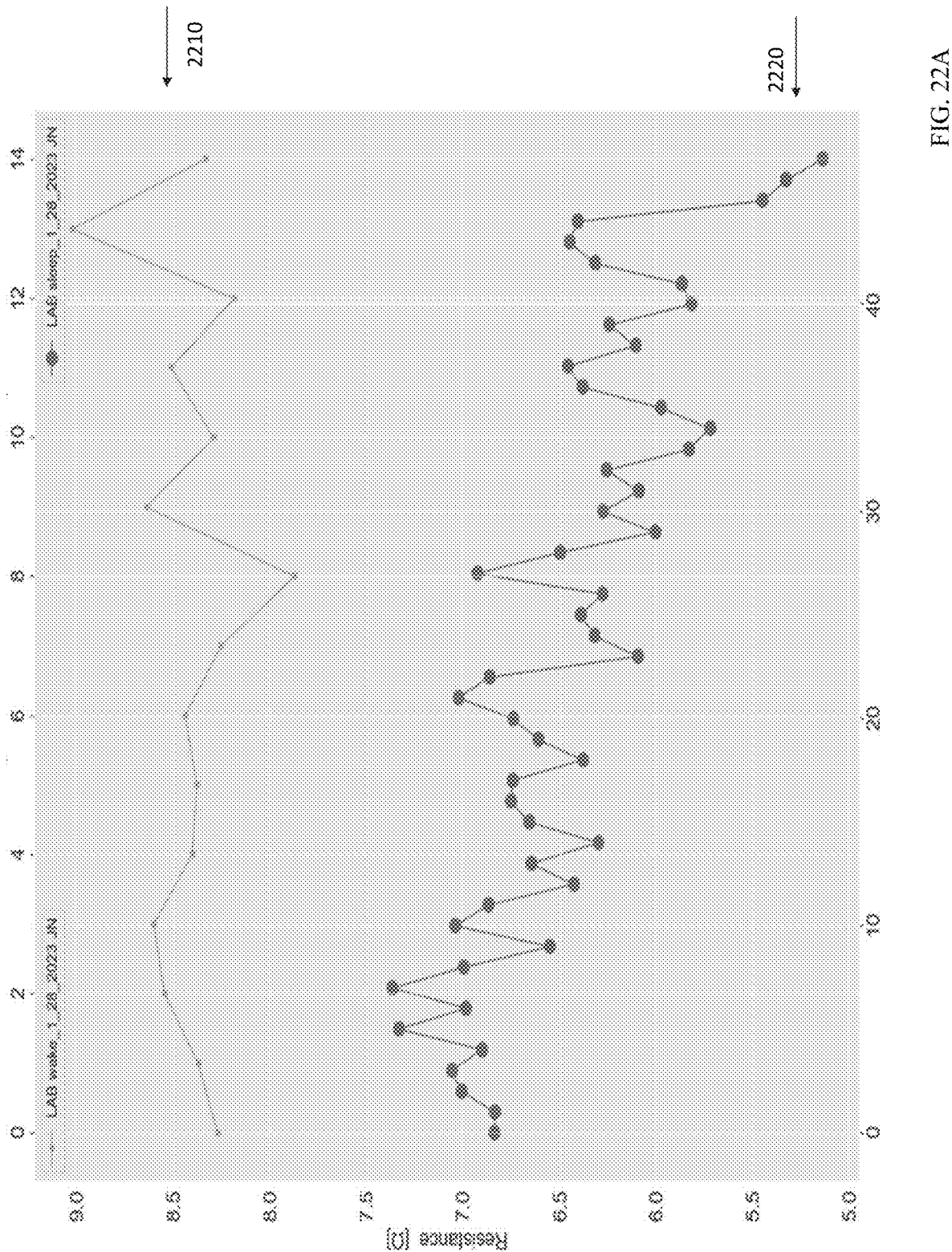
FIG. 22A illustrates another set of comparative resistance data collected during sleep and wake states of a subject in accordance with an example embodiment.
Figure 22B:
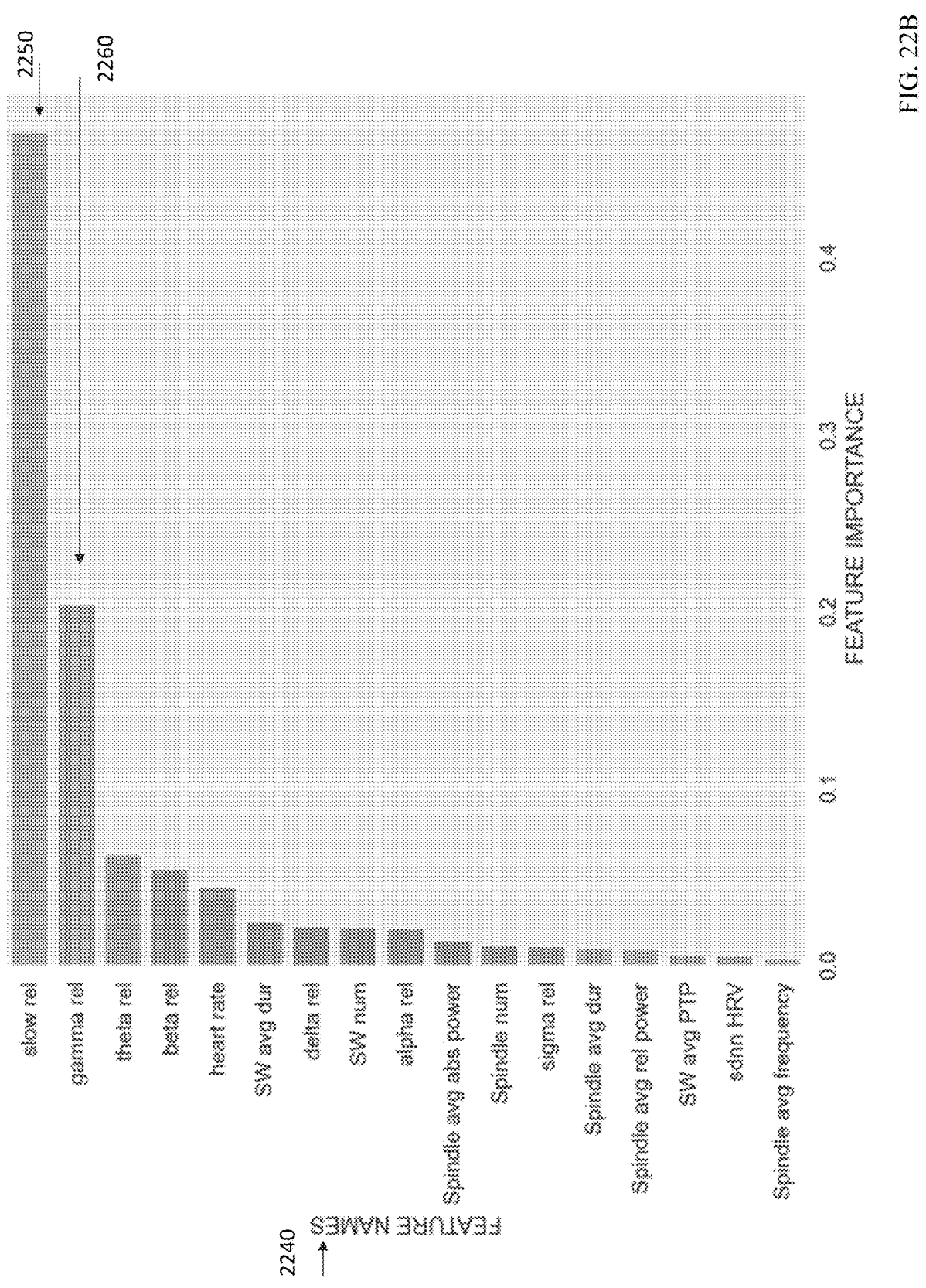
FIG. 22B illustrates features derived from EEG data and correlation to glymphatic fluid in accordance with an example embodiment.

FIG. 22A illustrates the spread or difference in glymphatic flow resistances over time computed from a model fit in an embodiment of the method and system configured in accordance with the present invention in a headcap used on a person who was required to lay awake overnight and on a subsequent second night was monitored during normal sleep. The intervention of wake/sleep is not intended to limit scope as one of ordinary skill would understand on review of this application that other interventions to glymphatic flow could be utilized without departing from the scope of the disclosure. Glymphatic flow resistances 2210 were measured during the overnight wake observation period and demonstrate no material change in resistance or glymphatic flow during that period as indicated by the generally constant resistances 2210 illustrated in FIG. 22A. In contrast, glymphatic flow resistances 2220 were measured during the overnight sleep observation period and show a significant decrease in resistance and corresponding increase in glymphatic flow with sleep. Using the method and system configured in accordance with the present invention in a headcap used on a person, in FIG. 22B the variability in glymphatic flow resistance in sleep, versus wake, is analyzed relative to the sleep physiology measures of the lower frequency EEG data that were contemporaneously recorded with the invention embodiment. FIG. 22B illustrates the variable importance output from a random forest regression of the glymphatic flow resistance 2220 on the sleep physiology measures 2240. Referring to FIG. 22B, 2250 and 2260 illustrate that for this user's sleep observation period, the spectral slow power band (between 0.4 Hz and 1 Hz) explained over 40% of the variability in the measured glymphatic flow resistance and gamma band power (above 30 Hz) accounted for another 20%.

Figure 23:
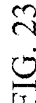
FIG. 23 illustrates comparative resistance data collected during sleep and wake states for a group of subjects in accordance with an example embodiment.

FIG. 23 illustrates the spread or difference in glymphatic flow resistances computed from a model fit in an embodiment of the method and system configured in accordance with the present invention in a headcap used by twelve persons who were randomized to sleep/wake on the first night and flipped to wake/sleep on a second night. Referring to FIG. 23, 2310 illustrates the average spread in resistances of the twelve individuals during the wake (sleep deprivation) observational period normalized to the resistance recorded at the beginning of that period. This average stays at or slightly above unity, the value measured at the beginning of the wake period. In FIG. 23 at 2330, the data illustrates the average spread in resistances of the twelve individuals during the sleep observation period, similarly normalized to the resistance recorded at the beginning of that period. In contrast to 2310, 2330 shows a steady continuous decline in the measured spread in resistances as the sleep observation period progresses during the night. The decrease in resistance spread leads to an increase in glymphatic flow during the night for these individuals.

Figure 24:
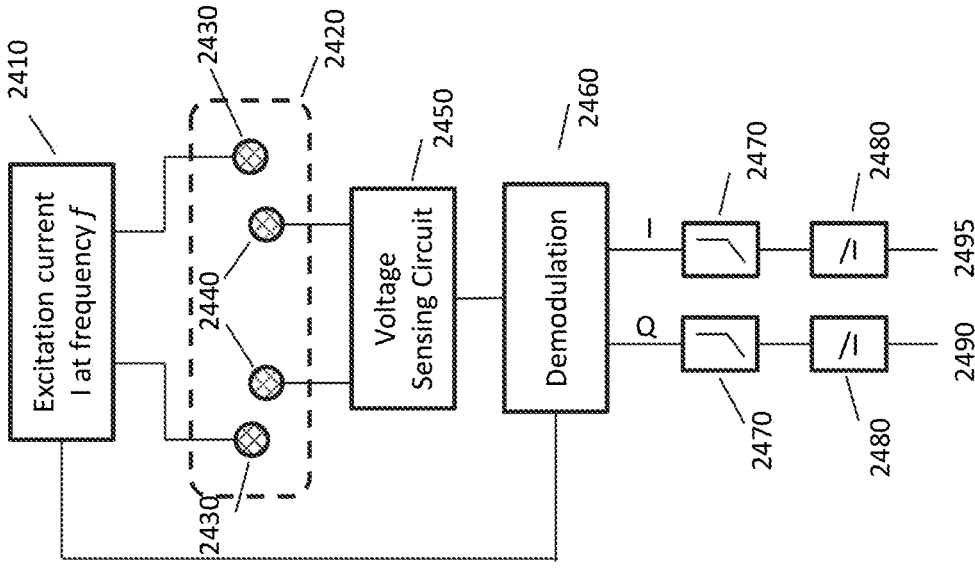
FIG. 24 illustrates a current injection and voltage sensing device in accordance with an example embodiment.

FIG. 24 illustrates an example of a current injection and sensing device 2400 that may be implemented in one of the previously-described head-mounted wearable devices. Alternatively, certain components of the device 2400, such as the demodulator and the filter, may be separated from a head-mounted wearable device and incorporated in a computing device that communicates with the device 2400. In this illustrated embodiment of the current injection and sensing device 2400, an impedance is measured using a 4-point measurement configuration, chosen to reduce the contribution of the electrodes to the measured impedance. As described in previous embodiments of the head-mounted wearable device, a current or voltage source 2410 can be implemented in a controller to generate the alternating input current. In source 2410, an alternating input current at the desired frequency is generated and injected into the tissue 2420 via a first pair of current input electrodes 2430. The resulting voltage from the input current is sensed by a second, separate pair voltage sensing electrodes 2440 and a voltage sensing circuit 2450. The current input electrodes and the voltage sensing electrodes can be placed at various locations on the head, including in the subject's ear, as described in the previous head-mounted wearable devices. The measured voltage is then demodulated by demodulator 2460 to provide both in-phase and out-of-phase components, which components are then low-pass filtered 2470 and converted into the real (resistance 2490) and imaginary (reactance 2495) parts of the impedance by division by the known excitation input current 2480 provided from input current source 2410. Calibration measurements are taken to reduce the effect of lead and parasitic capacitance, and increase absolute accuracy. Current is kept below levels admissible per safety standards (100 microampere, frequency-weighted). In an increase from the six alternating current measurements from the example of FIGS. 21A and B, this example uses fifteen input alternating current measurements at frequencies varying from 1 kHz and 100 kHz, which are then sequentially taken to generate an impedance spectrum characterizing the dispersion of the tissue. The acquisition time per frequencies is adjusted to provide the necessary resolution.

Figure 25:
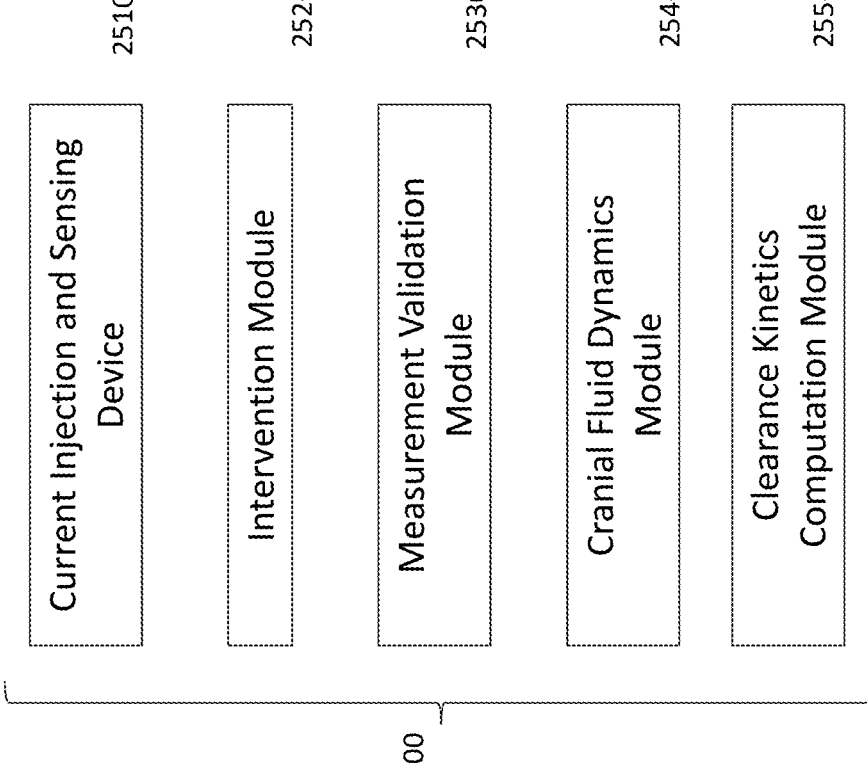
FIG. 25 illustrates components of a system for measuring glymphatic fluid in accordance with an example embodiment.

FIG. 25 illustrates components of a system 2500 of an embodiment configured in accordance with the present invention to measure glymphatic flow. Component 2510 is a current injection and sensing device, which can be similar to the device 2400 of FIG. 24, that acquires spectra either continuously or multiplexed in time with other electrical measurements (such as, but not limited to, electroencephalogram, electromyogram, electrooculogram, electrocardiogram) or electrical interventions (such as electrical stimulation).

Other embodiments of the current injection and sensing device make use of a larger number of frequencies to increase the resolution of the spectrum and to provide additional robustness to external interference. The frequency range can also be extended below 1 kHz and above 100 kHz to capture more of the dispersions found in brain tissues.

The excitation input alternating current may be generated by a current source or voltage source. In the case of a voltage source, the current is simultaneously measured so as to allow for the impedance to be computed. If the excitation input current is fixed, then the demodulated voltage can also be used directly to represent the impedance, without explicitly converting it into an impedance.

Multifrequency methods (measurement of multiple frequencies simultaneously), such as multi-sine or frequency-stacking methods, where the excitation is composed of multiple sine waves of different frequencies and amplitudes, or chirp-based and other FFT-based methods may also be used in some embodiments to reduce the measurement time.

The intervention module 2520 subjects the user to one or more programmed interventions during the operation of current injection and voltage sensing. Non-limiting examples of these interventions include sleep/sleep deprivation, a pharmaceutical intervention that manipulates a key target of glymphatic function, neurostimulation that manipulates a key target of glymphatic function, or a physiological intervention known to affect glymphatic function. As one example, the intervention module 2520 can comprise a set of computer-executable instructions that control delivery of a pharmaceutical to the subject or that control delivery of electrostimulation to the subject.

A measurement validation module 2530 can validate the input alternating current and sensing data and calculate an impedance spectra over the range of the input alternating currents. Specifically, each current injection and sensing data acquired following the programmed intervention is validated by measurement validation module 2530 using one of a Hilbert transform or Kramer-Kronig test as previously described. These tests leverage the analytical property that only the real or the imaginary part of the sense data is required to fit a complete model to one impedance spectra and the conjugate sense data (imaginary if real is used to fit the model) can be derived from the fit model. If the latter fails then that impedance spectra is rejected. By optimizing the hardware device 2510 to enable short time acquisitions of each impedance spectra, device 2510 can be operated repeatedly, time-multiplexed with other sensors if necessary, and multiple impedance spectra can be captured over the intervention period. Thus, the output of 2530 is a time-series of valid impedance spectra.

The validated time-series impedance spectra from 2530 is used in the cranial fluid dynamics module 2540 to compute the time-course of the resistance to glymphatic flow in the brain parenchyma during the intervention period of the programmed intervention(s). During that period, each recorded impedance spectra is fit to an electrical circuit model using a non-linear least squares fit model. Using the model fit for each recorded impedance spectra, the impedances can be extrapolated to low and high frequencies. The difference of impedances at these frequencies measures the resistance to glymphatic flow at that time point. The time-course of these resistances generated by the repeatedly recorded impedance spectra during the programmed interventions is outputted by the module 2540 as the dynamic glymphatic flow response to the intervention. Examples of a glymphatic flow response to a wake/sleep intervention are illustrated in FIGS. 22A and 23 as previously described.

The dynamic glymphatic flow response that is output from module 2540 is used in the clearance kinetics computation module 2550 to calculate the rate of elimination of parenchymal waste products residing in the interstitial fluid compartment of the brain based on the waste product's clearance kinetics. For example, for waste products that undergo zero order kinetics a constant amount of waste is cleared per unit of time, that amount being proportional to the instantaneous glymphatic flow determined by module 2540. The total amount of waste products cleared can be computed by numerically integrating the instantaneous glymphatic flow determined by module 2540 over the intervention period. The effect of a programmed intervention on the clearance rate will be directly proportional to its effect on the glymphatic flow rate for zero order kinetic waste. In contrast, waste that undergoes first order kinetics is cleared at a rate proportional to the amount of waste present, with that proportionality constant dependent on the glymphatic flow rate. Waste can display zero-order kinetic clearance at high concentrations in the parenchymal interstitial fluid and first-order kinetic clearance at low concentrations. When parenchymal interstitial fluid is waste saturated, clearance kinetics is flow limited and varies proportionally with flow similar to zero-order kinetic behavior. Module 2550 can be used to compute the level of saturation of the waste in the brain parenchymal fluid by sampling venous concentrations of the eliminated waste under a program of interventions that varies cranial fluid flow.

As previously described in connection with FIG. 3, the intervention module 2520, the measurement validation module 2530, the cranial fluid dynamics computation module 2540, and the clearance kinetics computation module 2550 can be implemented as computer-executable instructions and data that are stored on a head-mounted wearable device or a portion of which may be stored on a computing device that is separate from but in communication with the head-mounted wearable device.

Figure 26:
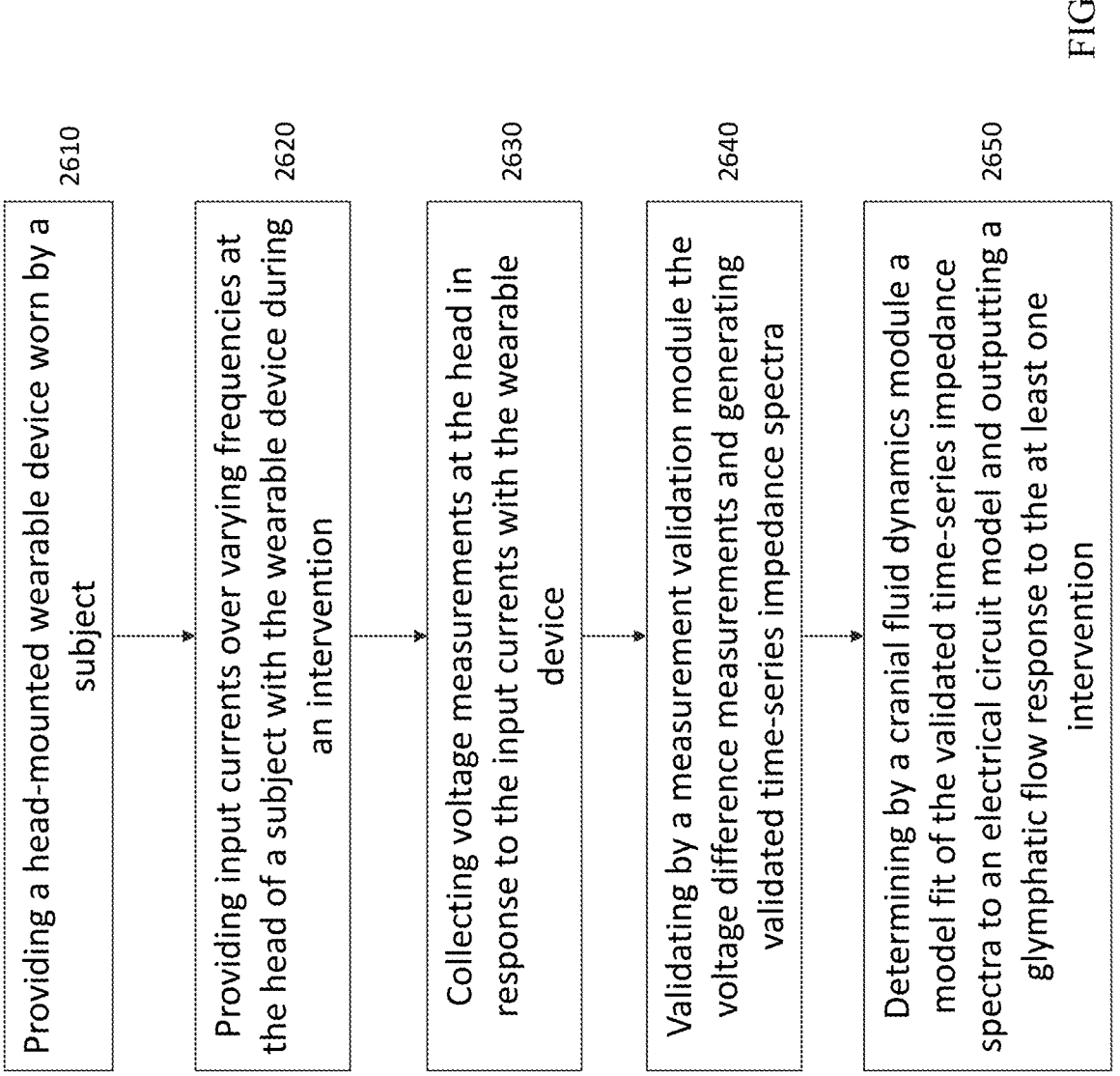
FIG. 26 illustrates a method for measuring glymphatic fluid in accordance with an example embodiment.

Referring now to FIG. 26, an example method 2600 is illustrated for determining a glymphatic flow response to at least one intervention performed on a subject. Example method 2600 is an illustrative embodiment and other embodiments implementing the head-mounted wearable devices described herein may modify or add to the operations of method 2600. In operation 2610, a head-mounted wearable device is provided and placed on a subject's head. The head-mounted wearable device can be any of the various examples provided in the previous description. In operation 2620, at least two current electrodes of the head-mounted wearable device provide input alternating currents over a range of frequencies to the subject's head. The input alternating currents can be provided to the subject at several intervals over an observation period. In operation 2630, sensing electrodes of the head-mounted wearable device collect voltage difference measurements across various regions of the subject's head. The voltage difference measurements are collected in response to the input alternating currents. In operation 2640, a measurement validation module receives the collected voltage difference measurements and the input alternating current values and validates the data to remove any erroneous measurements. The measurement validation module uses the validated data to generate validated time-series impedance spectra. In operation 2650, a cranial fluid dynamics module determines a model fit of the validated time-series impedance spectra to an electrical circuit model. The model fit provides a glymphatic flow response to the at least one intervention that is output by the cranial fluid dynamics module. The glymphatic flow response can be used for several purposes including assessments of brain interstitial volumes and flows as well as assessments of the subject's health or disease progression.

The invention claimed is:

1. A brain monitoring system comprising:
a head-mounted device that comprises a plurality of left electrodes and a plurality of right electrodes;
a microcontroller in communication with the plurality of left and right electrodes,
wherein the microcontroller generates an input alternating current during multiple iterations,
wherein, for each iteration of the multiple iterations, the microcontroller selects an input electrode and a sink electrode from among the plurality of left and right electrodes for providing the input alternating current to a subject wearing the head-mounted device,
wherein a remainder of the plurality of left and right electrodes after selecting the input and sink electrodes are sense electrodes that collect voltage difference measurements in response to the input alternating current;
a measurement validation module that:
filters invalid voltage difference measurements and generates, from validated voltage difference measurements, a time-series of validated impedance spectra for the multiple iterations,
wherein a change in the time-series of validated impedance spectra during the multiple iterations indicates a change in flow of cranial interstitial fluid; and
a cranial fluid dynamics module that:
determines a model fit of the time-series of validated impedance spectra, and outputs a glymphatic flow response during the multiple iterations based upon the model fit of the time-series of validated impedance spectra, and
responsive to receiving the glymphatic flow response, the microcontroller performs one or more of displaying the glymphatic flow response on a display and administering at least one therapeutic intervention.

2. The brain monitoring system of claim 1, wherein the microcontroller varies the input electrode and the sink electrode among the plurality of left and right electrodes during each iteration.

3. The brain monitoring system of claim 2, wherein the microcontroller varies the input alternating current over a range of frequencies during each iteration and includes at least one input alternating current having a frequency greater than zero but less than 10 kHz.

4. The brain monitoring system of claim 1, wherein the brain monitoring system administers at least one target engagement intervention during the multiple iterations.

5. The brain monitoring system of claim 1, wherein the at least one therapeutic intervention is one of drug administration, electrostimulation, and physiological stimulation.

6. The brain monitoring system of claim 5, further comprising an intervention module that controls one of the drug administration, the electrostimulation, or the physiological stimulation.

7. The brain monitoring system of claim 5, wherein the cranial fluid dynamics module compares the glymphatic flow response to the at least one therapeutic intervention to glymphatic flow responses gathered from the subject previously and provides an assessment of disease progression or response of the subject to the at least one therapeutic intervention.

8. The brain monitoring system of claim 5, wherein the cranial fluid dynamics module compares the glymphatic flow response to the at least one therapeutic intervention to a population distribution of glymphatic flow responses gathered from other subjects and provides an assessment of disease progression for the subject.

9. The brain monitoring system of claim 1, wherein the plurality of left electrodes are positioned to be located over the left frontal, temporal, and parietal lobes when the head-mounted device is placed on the subject, and wherein the plurality of right electrodes are positioned to be located over the right frontal, temporal, and parietal lobes when the head-mounted device is placed on the subject.

10. The brain monitoring system of claim 1, wherein the glymphatic flow response indicates a change in volume of the cranial interstitial fluid.

11. A method for measuring glymphatic flow using a brain monitoring system, the brain monitoring system comprising a microcontroller and a head-mounted device, the method comprising:
providing the head-mounted device worn by a subject, the head-mounted device comprising:
a plurality of left electrodes in communication with the microcontroller, and
a plurality of right electrodes in communication with the microcontroller;
generating, by the microcontroller, input alternating currents over a range of frequencies during multiple iterations;
providing, to the subject during each iteration of the multiple iterations, the input alternating currents over the range of frequencies via an input electrode and a sink electrode that the microcontroller selects from the plurality of left and right electrodes;
collecting, from the subject during the multiple iterations with a plurality of sense electrodes, voltage difference measurements in response to the input alternating currents, wherein the plurality of sense electrodes comprises the plurality of left and right electrodes remaining after the microcontroller selects the input and sink electrodes;
filtering, by a measurement validation module, invalid voltage difference measurements;
generating, by the measurement validation module from validated voltage difference measurements, a time-series of validated impedance spectra over the multiple iterations, wherein a change in the validated impedance spectra over the multiple iterations indicates a change in flow of cranial interstitial fluid;

determining, by a cranial fluid dynamics module, a model fit of the time-series of validated impedance spectra, outputting, by the cranial fluid dynamics module, a glymphatic flow response during the multiple iterations based upon the model fit of the time-series of validated impedance spectra, and responsive to receiving the glymphatic flow response, performing by the microcontroller one or more of displaying the glymphatic flow response on a display and administering at least one therapeutic intervention.

12. The method of claim 11, wherein the microcontroller varies the input electrode and the sink electrode among the plurality of left and right electrodes during the iteration.

13. The method of claim 12, wherein the range of frequencies includes at least one input alternating current having a frequency greater than zero and less than 10 KHz.

14. The method of claim 11, wherein the subject wearing the head-mounted device experiences at least one target engagement intervention during the multiple iterations.

15. The method of claim 11, wherein the at least one therapeutic intervention is one of drug administration, electrostimulation, and physiological stimulation.

16. The method of claim 15, further comprising controlling, by an intervention module, one of the drug administration, the electrostimulation, or the physiological stimulation.

17. The method of claim 15, further comprising:

comparing, by the cranial fluid dynamics module, the glymphatic flow response to the at least one therapeutic intervention to glymphatic flow responses gathered from the subject previously; and providing, by the cranial fluid dynamics module, an assessment of disease progression or response of the subject to the at least one therapeutic intervention.

18. The method of claim 15, further comprising:

comparing, by the cranial fluid dynamics module, the glymphatic flow response to the at least one therapeutic intervention to a population distribution of glymphatic flow responses gathered from other subjects; and providing, by the cranial fluid dynamics module, an assessment of disease progression for the subject.

19. The method of claim 11, wherein the measurement validation module and the cranial fluid dynamics module reside in a computing device that communicates with the head-mounted device.

20. The method of claim 11, wherein the plurality of left electrodes is positioned to be located over the left frontal, temporal, and parietal lobes when the head-mounted device is placed on the subject, and wherein the plurality of right electrodes is positioned to be located over the right frontal, temporal, and parietal lobes when the head-mounted device is placed on the subject.

* * * * *